United States Patent
Mainzer et al.

(10) Patent No.: US 10,413,871 B2
(45) Date of Patent: Sep. 17, 2019

(54) STABILIZATION OF BIOMIMETIC MEMBRANES

(71) Applicant: DANISCO US INC., Palo Alto, CA (US)

(72) Inventors: Stanley E. Mainzer, Burlingame, CA (US); Jakob Broberg Kristensen, Brabrand (DK); Maria Ines Plasencia Gil, Odense (DK)

(73) Assignee: DANISCO US INC, Palo Alto, CA (US)

( * ) Notice: Subject to any disclaimer, the term of this patent is extended or adjusted under 35 U.S.C. 154(b) by 0 days.

(21) Appl. No.: 16/216,103

(22) Filed: Dec. 11, 2018

(65) Prior Publication Data
US 2019/0099725 A1 Apr. 4, 2019

Related U.S. Application Data

(62) Division of application No. 14/436,216, filed as application No. PCT/US2013/065746 on Oct. 18, 2013.

(Continued)

(51) Int. Cl.
| | |
|---|---|
| *B01D 71/74* | (2006.01) |
| *C07K 14/37* | (2006.01) |
| *C02F 1/44* | (2006.01) |
| *B01D 61/00* | (2006.01) |
| *B01D 69/14* | (2006.01) |

(Continued)

(52) U.S. Cl.
CPC ......... *B01D 71/74* (2013.01); *B01D 61/002* (2013.01); *B01D 67/0011* (2013.01); *B01D 69/144* (2013.01); *B01D 71/06* (2013.01); *C02F 1/44* (2013.01); *C07K 14/245* (2013.01); *C07K 14/315* (2013.01); *C07K 14/37* (2013.01); *C07K 14/415* (2013.01); *C02F 2303/10* (2013.01); *Y02W 10/30* (2015.05)

(58) Field of Classification Search
CPC ...... B01D 71/74; B01D 71/06; B01D 69/144; B01D 61/002; B01D 67/0002; B01D 67/0009; B01D 67/0011; B01D 67/0016; C07K 14/415; C07K 14/245; C07K 14/315; C07K 14/37; C02F 1/44; C02F 2303/10; Y02W 10/30
See application file for complete search history.

(56) References Cited

U.S. PATENT DOCUMENTS

| | | |
|---|---|---|
| 5,205,290 A | 4/1993 | Unger |
| 7,338,779 B1 | 3/2008 | Nakari-Setala et al. |

(Continued)

FOREIGN PATENT DOCUMENTS

| | | |
|---|---|---|
| EP | 2042156 A | 11/2007 |
| WO | 2001/57066 A2 | 8/2001 |

(Continued)

OTHER PUBLICATIONS

Sanna Askolin et al., Interaction and Comparison of a Class I Hydrophobin from Schizophyllum commune and Class II Hydrophobins from Trichoderma reesei, Biomacromolecules, 2006, pp. 1295-1301, vol. 7.

(Continued)

*Primary Examiner* — David C Mellon

(57) ABSTRACT

The present disclosure provides methods, compositions, kits and apparatuses for stabilizing membranes, membrane proteins, and/or membranes containing membrane proteins using hydrophobin.

11 Claims, 13 Drawing Sheets

Specification includes a Sequence Listing.

Related U.S. Application Data

(60) Provisional application No. 61/716,351, filed on Oct. 19, 2012.

(51) Int. Cl.

| | | |
|---|---|---|
| B01D 71/06 | (2006.01) | |
| C07K 14/245 | (2006.01) | |
| C07K 14/315 | (2006.01) | |
| C07K 14/415 | (2006.01) | |
| B01D 67/00 | (2006.01) | |

(56) References Cited

U.S. PATENT DOCUMENTS

| | | |
|---|---|---|
| 9,821,278 B2 | 11/2017 | Montemagno et al. |
| 2004/0049230 A1 | 3/2004 | Montemagno et al. |
| 2006/0040098 A1 | 2/2006 | Imbalzano et al. |
| 2006/0040349 A1 | 2/2006 | Sweigard et al. |
| 2006/0228484 A1 | 10/2006 | de Vocht et al. |
| 2009/0120874 A1 | 5/2009 | Jensen et al. |
| 2010/0111840 A1 | 5/2010 | Bednarski et al. |
| 2017/0065762 A1 | 3/2017 | Larsen et al. |

FOREIGN PATENT DOCUMENTS

| | | | |
|---|---|---|---|
| WO | 2001/57528 | A1 | 8/2001 |
| WO | 2006/082253 | A2 | 8/2006 |
| WO | 2006/103225 | A1 | 10/2006 |
| WO | 2006/103230 | A1 | 10/2006 |
| WO | 2007/014897 | A1 | 2/2007 |
| WO | 2007/030966 | A2 | 3/2007 |
| WO | 2007/087967 | A1 | 8/2007 |
| WO | 2007/087968 | A1 | 8/2007 |
| WO | 2008/019965 | A1 | 2/2008 |
| WO | 2008/107439 | A1 | 9/2008 |
| WO | 2008/110456 | A2 | 9/2008 |
| WO | 2008/116715 | A1 | 10/2008 |
| WO | 2009/050000 | A1 | 4/2009 |
| WO | 2008/120310 | A1 | 10/2009 |

OTHER PUBLICATIONS

Yohann Corvis et al., Analytical Investigation of the Interactions between SC3 Hydrophobin and Lipid Layers: Elaborating of Nanostructured Matrixes for Immobilizing Redox Systems, Anal. Chem., 2006, pp. 4850-4864, vol. 78.

Andrew R. Cox et al., Surface Properties of Class II Hydrophobins from Trichoderma reesei and Influence on Bubble Stability, Langmuir, 2007, pp. 7995-8002, vol. 23.

Marcel L. de Vocht et al., Structural Characterization of the Hydrophobin SC3, as a Monomer and after Self-Assembly at Hydrophobic/Hydrophilic Interfaces, Biophysical Journal, Apr. 1998, pp. 2059-2068, vol. 74.

Johanna Hakanpää et al., Atomic Resolution Structure of the HFBII Hydrophobin, a Self-assembling Amphiphile, The Journal of Biological Chemistry, Jan. 2, 2004, pp. 534-539, vol. 279, No. 1.

Johanna Hakanpää et al., Hydrophobin HFBII in detail: ultrahigh-resolution structure at 0.75 Å, Acta Cryst., 2006, pp. 356-367, D62.

Harm J. Hektor et al., Hydrophobins: proteins with potential, Current Opinion in Biotechnology, 2005, pp. 434-439, vol. 16.

Johanna M. Kallio et al., Crystal Structures of Hydrophobin HFBII in the Presence of Detergent Implicate the Formation of Fibils and Monolayer Films, The Journal of Biological Chemistry, Sep. 28, 2007, pp. 28733-28739, vol. 282, No. 39.

Kaisa Kisko et al., Self Assembled Films of Hydrophobin Proteins HFBI and HFBII Studied in Situ at the Air/Water Interface, Langmuir, 2009, pp. 1612-1619, vol. 25.

Christian P. Kubicek et al., Purifying selection and birth-and-death evolution in the class II hydrophobin gene families of the ascomycete Trichoderma/Hypocrea, BMC Evolutionary Biology, 2008, 16 pages, vol. 8:4.

Ann H. Kwan et al., The Cys3-Cys4 Loop of the Hydrophobin EAS is Not Required for Rodlet Formation and Surface Activity, J. Mol. Biol., 2008, pp. 708-720, vol. 382.

Päivi Laaksonen et al., Selective Nanopatterning Using Citrate-Stabilized Au Nanoparticles and Cystein-Modified Amphiphilic Protein, Langmuir, 2009, pp. 5185-5192, vol. 25, No. 9.

Tomi Lahtinen et al., Hydrophobin (HFBI): A potential fusion partner for one-step purification of recombinant proteins from insect cells, Protein Expression & Purification, 2008, pp. 18-24, vol. 59.

Markus Linder et al., The Hydrophobins HFBI and HFBII from Trichoderma reesei Showing Efficient Interactions with Nonionic Surfactants in Aqueous Two-Phase Systems, Biomacromolecules, 2001, pp. 511-551, vol. 2.

Markus B. Linder et al. Hydrophobins: the protein-amphiphiles of filamentous fungi, FEMS Microbiology Reviews, 2005, pp. 877-896, vol. 29.

Simon O. Lumsdon et al., Adsorption of hydrophobin proteins at hydrophobic and hydrophilic interfaces, Colloids and Surfaces B: Biointerfaces, 2005, pp. 172-178, vol. 44.

Tiina Nakari-Setala et al., Differential expression of the vegetative and spore-bound hydrophobins of Tricoderma reesei—Cloning and characterization of the hfb2 gene, Eur. J. Biochem, 1997, pp. 415-423, vol. 248.

Jose M. Palomo et al., Solid-Phase Handling of Hydrophobins: Immobilized Hydrophobins as a New Tool to Study Lipases, Biomacromolecules, 2003, pp. 204-210, vol. 4.

K. Scholtmeijer et al., Fungal Hydrophobins in medical and technical applications, Appl Microbiol Biotechnol, 2001, pp. 1-8, vol. 45.

Karin Scholtmeijer et al., Surface Modifications Created by Using Engineered Hydrophobins, Applied and Environmental Microbiology, Mar. 2002, pp. 1367-1373, vol. 68, No. 3.

Margaret Sunde et al., Structural analysis of hydrophobins, Micron, 2008, pp. 773-784, vol. 39.

Geza R. Szilvay et al., Self-Assembled Hydrophobin Protein Films at the Air-Water Interface: Structural Analysis and Molecular Engineering, Biochemistry, 2007, pp. 2345-2354, vol. 46.

Geza R. Szilvay et al., The relation between solution association and surface activity of the hydrophobin HFBI from Trichoderma reesei, FEBS Letter, 2007, pp. 2721-2726, vol. 581.

Chuyang Y. Tang et al., Aquaporin based biomimetic membranes for water reuse and desalination, Abstracts-acs org chem, XP002719530, Mar. 29, 2012, 1 page.

X. Wang et al., Pore formation of hydrophobin SC3 on a phospholipid bilayer, XP002719529, Dissertation—Chapter 6, pp. 119-143.

Xioqin Wang et al., Oligomerization of hydrophobin SC3 in solution: From soluble state to self-assembly, Protein Science, 2004, pp. 810-821, vol. 13.

Wosten, Han A. B. et al, Interfacial self-assembly of a hydrophobin into an amphipathic protein membrane mediates fungal attachment to hydrophobic surfaces, The EMBO Journal, 1994, pp. 5848-4854, vol. 13, No. 24.

Wosten, Han A. B., Hydrophobins: Multipurpose Proteins, Annu. Rev. Microbiol, 2001, pp. 625-646, vol. 55.

Yang, Kuan et al., Identification of new members of hydrophobin family using primary structure analysis, BMC Bioinformatics, 2006, 16 pages, 7 (Suppl 4).

Lei Yu et al., Protein HGFI from the edible mushroom Grifola frondosa is a novel 8 kDa class I hydrophobin that forms rodlets in compressed monolayers, Microbiology, 2008, pp. 1677-1685, vol. 154.

Xiaoli L. Zhang et al., Adsorption Behavior of Hydrophobin and Hydrophobin/Surfactant Mixtures at the Solid-Solution Interface, Langmuir, 2011, pp. 10464-10474, vol. 27.

Xiaoli L. Zhang et al., Self-Assembly of Hydrophobin and Hydrophobin/Surfactant Mixtures in Aqueous Solution, Langmuir, 2011, pp. 10514-10522, vol. 27.

Xiaoli L. Zhang et al., Adsorption Behavior of Hydrophobin and Hydrophobin/Surfactant Mixtures at the Air-Water Interface, Langmuir, 2011, pp. 11316-11323, vol. 27.

International Search Report and Written Opinion—PCT/US2013/065746—dated Feb. 11, 2014.

SEQ ID 1

| | | | | | | |
|---|---|---|---|---|---|---|
| cacattcact | caactcctct | ttctcaactc | tccaaacaca | aacattcttt | gttgaatacc | 60 |
| aaccatcacc | acctttcaag | atgcagttct | tcgccgtcgc | cctcttcgcc | accagcgccc | 120 |
| tggctgctgt | ctgccctacc | ggcctcttct | ccaaccctct | gtgctgtgcc | accaacgtcc | 180 |
| tcgacctcat | tggcgttgac | tgcaagaccc | gtatgttgaa | ttccaatctc | tgggcatcct | 240 |
| gacattggac | gatacagttg | acttacacga | tgctttacag | ctaccatcgc | cgtcgacact | 300 |
| ggcgccatct | tccaggctca | ctgtgccagc | aagggctcca | agcctctttg | ctgcgttgct | 360 |
| cccgtggtaa | gtagtgctcg | caatgcaaa | gaagtaaaaa | gacatttggg | cctgggatcg | 420 |
| ctaactcttg | atatcaaggc | cgaccaggct | ctcctgtgcc | agaaggccat | cggcaccttc | 480 |
| taaagcaatg | gcttgcttta | ctgccggcag | tctttgagaa | ctctgggctc | acaaaagacg | 540 |
| acttgcatgt | atcatggggg | ctcgcaaatg | ggaggatttg | gaggggattg | aggctgggtt | 600 |
| tggcctatta | gaggattgca | taatggaaga | tttgcgagca | ggacatagac | gtatctagag | 660 |
| ttctagt | | | | | | 667 |

FIG. 5

SEQ ID 2

Met Gln Phe Phe Ala Val Ala Leu Phe Ala Thr Ser Ala Leu Ala Ala
1           5                    10                     15

Val Cys Pro Thr Gly Leu Phe Ser Asn Pro Leu Cys Cys Ala Thr Asn
            20                   25                    30

Val Leu Asp Leu Ile Gly Val Asp Cys Lys Thr Pro Thr Ile Ala Val
            35                   40                    45

Asp Thr Gly Ala Ile Phe Gln Ala His Cys Ala Ser Lys Gly Ser Lys
            50                   55                    60

Pro Leu Cys Cys Val Ala Pro Val Ala Asp Gln Ala Leu Leu Cys Gln
65                   70                    75                    80

Lys Ala Ile Gly Thr Phe
                      85

FIG. 6

SEQ ID 3

| | | | | | | |
|---|---|---|---|---|---|---|
| tttgtatggc | tggatctcga | aaggcccttg | tcatcgccaa | gcgtggctaa | tatcgaatga | 60 |
| gggacaccga | gttgcatatc | tcctgatcat | tcaaacgaca | agtgtgaggt | aggcaatcct | 120 |
| cgtatcccat | tgctgggctg | aaagcttcac | acgtatcgca | taagcgtctc | caaccagtgc | 180 |
| ttaggtgacc | cttaaggata | cttacagtaa | gactgtatta | agtcagtcac | tctttcactc | 240 |
| gggctttgaa | tacgatcctc | aatactcccg | ataacagtaa | gaggatgata | cagcctgcag | 300 |
| ttggcaaatg | taagcgtaat | taaactcagc | tgaacggccc | ttgttgaaag | tctctctcga | 360 |
| tcaaagcaaa | gctatccaca | gacaagggtt | aagcaggctc | actcttccta | cgccttggat | 420 |
| atgcagcttg | ccagcatcg | cgcatggcca | atgatgcacc | cttcacggcc | caacggatct | 480 |
| cccgttaaac | tccctgtaa | cttggcatca | ctcatctgtg | atcccaacag | actgagttgg | 540 |
| gggctgcggc | tggcggatgt | cggagcaaag | gatcacttca | agagcccaga | tccggttggt | 600 |
| ccattgccaa | tggatctaga | ttcggcacct | tgatctcgat | cactgagaca | tggtgagttg | 660 |
| cccggacgca | ccacaactcc | cctgtgtca | ttgagtcccc | atatgcgtct | tctcagcgtg | 720 |
| caactctgag | acggattagt | cctcacgatg | aaattaactt | ccagcttaag | ttcgtagcct | 780 |
| tgaatgagtg | aagaaatttc | aaaaacaaac | tgagtagagg | tcttgagcag | ctggggtggt | 840 |
| acgcccctcc | tcgactcttg | ggacatcgta | cggcagagaa | tcaacggatt | cacacctttg | 900 |
| ggtcgagatg | agctgatctc | gacagatacg | tgcttcacca | cagctgcagc | tacctttgcc | 960 |
| caaccattgc | gttccaggat | cttgatctac | atcaccgcag | cacccgagcc | aggacggaga | 1020 |
| gaacaatccg | gccacagagc | agcaccgcct | tccaactctg | ctcctggcaa | cgtcacacaa | 1080 |
| cctgatatta | gatatccacc | tgggtgattg | ccattgcaga | gaggtggcag | ttggtgatac | 1140 |
| cgactggcca | tgcaagacgc | ggccgggcta | gctgaaatgt | ccccgagagg | acaattggga | 1200 |
| gcgtctatga | cggcgtggag | acgacgggaa | aggactcagc | cgtcatgttg | tgttgccaat | 1260 |
| ttgagattgt | tgaccgggaa | agggggacg | aagaggatgg | ctgggtgagg | tggtattggg | 1320 |
| aggatgcatc | attcgactca | gtgagcgatg | tagagctcca | agaatataaa | tatcccttct | 1380 |
| ctgtcttctc | aaaatctcct | tccatcttgt | ccttcatcag | caccagagcc | agcctgaaca | 1440 |
| cctccagtca | acttccctta | ccagtacatc | tgaatcaaca | tccattcttt | gaaatctcac | 1500 |
| cacaaccacc | atcttcttca | aaatgaagtt | cttcgccatc | gccgctctct | tgccgccgc | 1560 |

*FIG. 7A*

```
tgccgttgcc cagcctctcg aggaccgcag caacggcaac ggcaatgttt gccctcccgg  1620
cctcttcagc aacccccagt gctgtgccac ccaagtcctt ggcctcatcg gccttgactg  1680
caaagtccgt aagttgagcc ataacataag aatcctcttg acggaaatat gccttctcac  1740
tcctttaccc ctgaacagcc tcccagaacg tttacgacgg caccgacttc cgcaacgtct  1800
gcgccaaaac cggcgcccag cctctctgct gcgtggcccc cgttgtaagt tgatgcccca  1860
gctcaagctc cagtctttgg caaacccatt ctgacaccca gactgcaggc cggccaggct  1920
cttctgtgcc agaccgccgt cggtgcttga gatgcccgcc cggggtcaag gtgtgcccgt  1980
gagaaagccc acaaagtgtt gatgaggacc atttccggta ctgggaaagt tggctccacg  2040
tgtttgggca ggtttgggca agttgtgtag atattccatt cgtacgccat tcttattctc  2100
caatatttca gtacactttt cttcataaat caaaaagact gctattctct ttgtgacatg  2160
ccggaaggga acaattgctc ttggtctctg ttatttgcaa gtaggagtgg gagattcgcc  2220
ttagagaaag tagagaagct gtgcttgacc gtggtgtgac tcgacgagga tggactgaga  2280
gtgttaggat taggtcgaac gttgaagtgt atacaggatc gtctggcaac ccacggatcc  2340
tatgacttga tgcaatggtg aagatgaatg acagtgtaag aggaaaagga aatgtccgcc  2400
ttcagctgat atccacgcca atgatacagc gatatacctc caatatctgt gggaacgaga  2460
catgacatat ttgtgggaac aacttcaaac agcgagccaa gacctcaata tgcacatcca  2520
aagccaaaca ttggcaagac gagagacagt cacattgtcg tcgaaagatg gcatcgtacc  2580
caaatcatca gctctcatta tcgcctaaac cacagattgt ttgccgtccc ccaactccaa  2640
aacgttacta caaaagacat gggcgaatgc aaagacctga agcaaacccc tttttgcgac  2700
tcaattccct cctttgtcct cggaatgatg atccttcacc aagtaaaaga aaaagaagat  2760
tgagataata catgaaaagc acaacggaaa cgaaagaacc aggaaaagaa taaatctatc  2820
acgcaccttg tccccacact aaaagcaaca gggggggtaa aatgaaat             2868
```

*FIG. 7B*

SEQ ID 4

| | | | | | | | | | | | | | | |
|---|---|---|---|---|---|---|---|---|---|---|---|---|---|---|
|Met|Lys|Phe|Phe|Ala|Ile|Ala|Ala|Leu|Phe|Ala|Ala|Ala|Val|Ala|
|1| | | |5| | | | |10| | | | |15|

Gln Pro Leu Glu Asp Arg Ser Asn Gly Asn Gly Asn Val Cys Pro Pro
20 25 30

Gly Leu Phe Ser Asn Pro Gln Cys Cys Ala Thr Gln Val Leu Gly Leu
35 40 45

Ile Gly Leu Asp Cys Lys Val Pro Ser Gln Asn Val Tyr Asp Gly Thr
50 55 60

Asp Phe Arg Asn Val Cys Ala Lys Thr Gly Ala Gln Pro Leu Cys Cys
65 70 75 80

Val Ala Pro Val Ala Gly Gln Ala Leu Leu Cys Gln Thr Ala Val Gly
85 90 95

Ala

*FIG. 8*

SEQ ID 5

```
agtcgaacac cccagttcaa ctaccccagc ccttccttcc ttcgctatcc ttccttacaa    60
cctgctcgcc atgttcgccc gtctcccgt cgtgttcctc tacgccttcg tcgcgttcgg   120
cgccctcgtc gctgccctcc caggtggcca cccgggcacg acgtacgtcg acctctcacc   180
gtcctctaat gtcttgctga tgaagcccg tatagcacgc cgccggttac gacgacggtg   240
acggtgacca cggtgagtag ctttctcgcc gtcgacgact cgaacgcatt ggctaatttt   300
tgctcatagc cgccctcgac gacgaccatc gccgccggtg gcacgtgtac tacggggtcg   360
ctctcttgct gcaaccaggt tcaatcggta cgtacatcaa agcggcacga ccaggcatct   420
cagctgacgg ccacatcgta caggcgagca gcagccctgt taccgccctc ctcggcctgc   480
tcggcattgt cctcagcgac ctcaacgttc tgttggcat cagctgctct cccctcactg   540
tgagatcttt ttgttcactg tcccaattac tgcgcactga cagactttgc caggtcatcg   600
gtgtcggagg cagcggctgt tcggcgcaga ccgtctgctg cgaaaacacc caattcgtat   660
gtatactttc catgcgtgtc cctttctccg ctaatcatct gtagaacggg ctgatcaaca   720
tcggttgcac ccccatcaac atcctctgag caggtgaacg cgcctgtcgg tgggatattc   780
gggcgacggg agcctcgggc aatctgagcc tcgttactgc ctagcaaatt cggaatccct   840
tcgatgtcat agggtcgcgg acaagtgatc gtcttgctac atactccaag gtgttgactc   900
attccctcag ataatgaaca ttgttgttgt tgttgtttgt tctct               945
```

*FIG. 9*

SEQ ID 6

| | | | | | | | | | | | | | | |
|---|---|---|---|---|---|---|---|---|---|---|---|---|---|---|
| Met | Phe | Ala | Arg | Leu | Pro | Val | Val | Phe | Leu | Tyr | Ala | Phe | Val | Ala | Phe |
| 1 | | | | 5 | | | | | 10 | | | | | 15 |
| Gly | Ala | Leu | Val | Ala | Ala | Leu | Pro | Gly | Gly | His | Pro | Gly | Thr | Thr | Thr |
| | | | 20 | | | | | 25 | | | | | 30 | | |
| Pro | Pro | Val | Thr | Thr | Thr | Val | Thr | Val | Thr | Thr | Pro | Pro | Ser | Thr | Thr |
| | | 35 | | | | | 40 | | | | | 45 | | | |
| Thr | Ile | Ala | Ala | Gly | Gly | Thr | Cys | Thr | Thr | Gly | Ser | Leu | Ser | Cys | Cys |
| | 50 | | | | | 55 | | | | | 60 | | | | |
| Asn | Gln | Val | Gln | Ser | Ala | Ser | Ser | Ser | Pro | Val | Thr | Ala | Leu | Leu | Gly |
| 65 | | | | | 70 | | | | | 75 | | | | | 80 |
| Leu | Leu | Gly | Ile | Val | Leu | Ser | Asp | Leu | Asn | Val | Leu | Val | Gly | Ile | Ser |
| | | | | 85 | | | | | 90 | | | | | 95 | |
| Cys | Ser | Pro | Leu | Thr | Val | Ile | Gly | Val | Gly | Gly | Ser | Gly | Cys | Ser | Ala |
| | | | 100 | | | | | 105 | | | | | 110 | | |
| Gln | Thr | Val | Cys | Cys | Glu | Asn | Thr | Gln | Phe | Asn | Gly | Leu | Ile | Asn | Ile |
| | | 115 | | | | | 120 | | | | | 125 | | | |
| Gly | Cys | Thr | Pro | Ile | Asn | Ile | Leu | | | | | | | | |
| | 130 | | | | | 135 | | | | | | | | | |

FIG. 10

SEQ ID 7

```
atcatcagca tcaacatctt cacttcacaa catcttctca accttccaac tcaccttcca      60
aaccaccttc aaaaccaact cccagcttct ttcagcaaac ccccaaccgc aaaatgcag       120
ttcaccagcg tcttcaccat cctcgccatt gccatgaccg ccgctgcggc ccggctgag       180
gttgttcccc gcgccaccac catcggcccc aacacctgct ccatcgacga ctacaagcct      240
tactgctgcc agtctatgtc cggccccgcc ggctcccctg gtctcctcaa cctcatcccc      300
gtcgacctca gcgcctcgct cggctgcgtt gtcggtgtca tcggctccca atgtggtgcc      360
agcgtcaagt gctgcaagga cgatgttacc aacaccggca actccttcct catcatcaac      420
gctgccaact gcgttgccta agtgtttacg cggcaacagc gcaaagtcta ggcaatgcct      480
tgttctcaac gctgctgcca gtccagcacc ccccttctgc agcaaggagc cccttctgc       540
tggactggca gcacaacgag ctgctactac aacacaagca tcatgcctgg acgcaacaga      600
agccgataat cttggggttt ggttttgggg gatgaaggtg atgagttgat ggattggatc      660
gatatcttac aatgcgtgtc tcttcctgtt aagatctgct ttactatttt cctatttct       720
tttacacata gctatgtatc actaaggcct ggtgattaat acactctctt aaccct          776
```

FIG. 11

SEQ ID 8

Met Gln Phe Thr Ser Val Phe Thr Ile Leu Ala Ile Ala Met Thr Ala
1               5                   10                  15

Ala Ala Ala Pro Ala Glu Val Val Pro Arg Ala Thr Thr Ile Gly Pro
                20                  25                  30

Asn Thr Cys Ser Ile Asp Asp Tyr Lys Pro Tyr Cys Cys Gln Ser Met
            35                  40                  45

Ser Gly Pro Ala Gly Ser Pro Gly Leu Leu Asn Leu Ile Pro Val Asp
        50                  55                  60

Leu Ser Ala Ser Leu Gly Cys Val Val Gly Val Ile Gly Ser Gln Cys
65                  70                  75                  80

Gly Ala Ser Val Lys Cys Cys Lys Asp Asp Val Thr Asn Thr Gly Asn
                85                  90                  95

Ser Phe Leu Ile Ile Asn Ala Ala Asn Cys Val Ala
            100                 105

FIG. 12

SEQ ID 9

| atgaagttcg | ccggtgtctt | gcttgctgtc | gccgctgcgg | cgactgccct | gccaaacgtc | 60 |
| ggtcccagtg | ggaagacggc | tcacaagccg | caccaggagc | ctttctggcc | tgtgcagcag | 120 |
| gacgtgaccg | tggaacaggc | caaggctatc | tgtggtgaag | caaccaggt | cgcttgctg | 180 |
| aacgaggtca | gctacgcggg | cgacaccacc | gaaatcgcga | ccggcccct | ggctggcacc | 240 |
| ctcaaggacc | tgctcggcgg | caagaacggc | gccaagggcc | tgggtctctt | cgacaagtgc | 300 |
| tcgcgtctca | atgtcgatct | cctgcttggc | ctgtcgagcc | tcatcaacca | agaatgcaag | 360 |
| cagcacattg | cctgctgcca | gggcaacgag | gccgattcct | ccaacgacct | catcggtctc | 420 |
| aacattcctt | gcattgccct | tggctcgctg | ctg |  |  | 453 |

FIG. 13

SEQ ID 10

| | | | | | | | | | | | | | | |
|---|---|---|---|---|---|---|---|---|---|---|---|---|---|---|
|Met|Lys|Phe|Ala|Gly|Val|Leu|Leu|Ala|Val|Ala|Ala|Ala|Thr|Ala|
|1| | | |5| | | | |10| | | | |15|

| | | | | | | | | | | | | | | |
|---|---|---|---|---|---|---|---|---|---|---|---|---|---|---|
|Leu|Pro|Asn|Val|Gly|Pro|Ser|Gly|Lys|Thr|Ala|His|Lys|Pro|His|Gln|
| | | |20| | | |25| | | | |30| | |

| | | | | | | | | | | | | |
|---|---|---|---|---|---|---|---|---|---|---|---|---|
|Glu|Pro|Phe|Trp|Pro|Val|Gln|Gln|Asp|Val|Thr|Val|Glu|Gln|Ala|Lys|
| | |35| | | | |40| | | | |45| | |

| | | | | | | | | | | | | |
|---|---|---|---|---|---|---|---|---|---|---|---|---|
|Ala|Ile|Cys|Gly|Glu|Gly|Asn|Gln|Val|Ala|Cys|Cys|Asn|Glu|Val|Ser|
| |50| | | | |55| | | | |60| | | |

|Tyr|Ala|Gly|Asp|Thr|Thr|Glu|Ile|Ala|Thr|Gly|Pro|Leu|Ala|Gly|Thr|
|---|---|---|---|---|---|---|---|---|---|---|---|---|---|---|---|
|65| | | | |70| | | | |75| | | | |80|

|Leu|Lys|Asp|Leu|Leu|Gly|Gly|Lys|Asn|Gly|Ala|Lys|Gly|Leu|Gly|Leu|
|---|---|---|---|---|---|---|---|---|---|---|---|---|---|---|---|
| | | | |85| | | | |90| | | | |95| |

|Phe|Asp|Lys|Cys|Ser|Arg|Leu|Asn|Val|Asp|Leu|Leu|Leu|Gly|Leu|Ser|
|---|---|---|---|---|---|---|---|---|---|---|---|---|---|---|---|
| | | |100| | | | |105| | | | |110| | |

|Ser|Leu|Ile|Asn|Gln|Glu|Cys|Lys|Gln|His|Ile|Ala|Cys|Cys|Gln|Gly|
|---|---|---|---|---|---|---|---|---|---|---|---|---|---|---|---|
| | |115| | | | |120| | | | |125| | | |

|Asn|Glu|Ala|Asp|Ser|Ser|Asn|Asp|Leu|Ile|Gly|Leu|Asn|Ile|Pro|Cys|
|---|---|---|---|---|---|---|---|---|---|---|---|---|---|---|---|
| |130| | | | |135| | | | |140| | | | |

|Ile|Ala|Leu|Gly|Ser|Leu|Leu|
|---|---|---|---|---|---|---|
|145| | | | |150| |

FIG. 14

SEQUENCE LISTING

<160> NUMBER OF SEQ ID NOS: 10

<210> SEQ ID NO 1
<211> LENGTH: 667
<212> TYPE: DNA
<213> ORGANISM: Trichoderma reesei

<400> SEQUENCE: 1

```
cacattcact caactcctct ttctcaactc tccaaacaca aacattcttt gttgaatacc        60
aaccatcacc acctttcaag atgcagttct tcgccgtcgc cctcttcgcc accagcgccc       120
tggctgctgt ctgccctacc ggcctcttct ccaaccctct gtgctgtgcc accaacgtcc       180
tcgacctcat tggcgttgac tgcaagaccc gtatgttgaa ttccaatctc tgggcatcct       240
gacattggac gatacagttg acttacacga tgctttacag ctaccatcgc cgtcgacact       300
ggcgccatct tccaggctca ctgtgccagc aagggctcca agcctctttg ctgcgttgct       360
cccgtggtaa gtagtgctcg caatggcaaa gaagtaaaaa gacatttggg cctgggatcg       420
ctaactcttg atatcaaggc cgaccaggct ctcctgtgcc agaaggccat cggcaccttc       480
taaagcaatg gcttgcttta ctgccggcag tctttgagaa ctctgggctc acaaaagacg       540
acttgcatgt atcatggggg ctcgcaaatg ggaggatttg gaggggattg aggctgggtt       600
tggcctatta gaggattgca taatggaaga tttgcgagca ggacatagac gtatctagag       660
ttctagt                                                                 667
```

<210> SEQ ID NO 2
<211> LENGTH: 86
<212> TYPE: PRT
<213> ORGANISM: Trichoderma reesei

<400> SEQUENCE: 2

Met Gln Phe Phe Ala Val Ala Leu Phe Ala Thr Ser Ala Leu Ala Ala
1               5                   10                  15

Val Cys Pro Thr Gly Leu Phe Ser Asn Pro Leu Cys Cys Ala Thr Asn
            20                  25                  30

Val Leu Asp Leu Ile Gly Val Asp Cys Lys Thr Pro Thr Ile Ala Val
        35                  40                  45

Asp Thr Gly Ala Ile Phe Gln Ala His Cys Ala Ser Lys Gly Ser Lys
    50                  55                  60

Pro Leu Cys Cys Val Ala Pro Val Ala Asp Gln Ala Leu Leu Cys Gln
65                  70                  75                  80

Lys Ala Ile Gly Thr Phe
                85

<210> SEQ ID NO 3
<211> LENGTH: 2868
<212> TYPE: DNA
<213> ORGANISM: Trichoderma reesei

<400> SEQUENCE: 3
tttgtatggc tggatctcga aaggcccttg tcatcgccaa gcgtggctaa tatcgaatga      60
gggacaccga gttgcatatc tcctgatcat tcaaacgaca agtgtgaggt aggcaatcct     120
cgtatcccat tgctgggctg aaagcttcac acgtatcgca taagcgtctc caaccagtgc     180
ttaggtgacc cttaaggata cttacagtaa gactgtatta agtcagtcac tctttcactc     240
gggctttgaa tacgatcctc aatactcccg ataacagtaa gaggatgata cagcctgcag     300
ttggcaaatg taagcgtaat taaactcagc tgaacggccc ttgttgaaag tctctctcga     360
tcaaagcaaa gctatccaca gacaagggtt aagcaggctc actcttccta cgccttggat     420
atgcagcttg ccagcatcg cgcatggcca atgatgcacc cttcacggcc caacggatct     480
cccgttaaac tcccctgtaa cttggcatca ctcatctgtg atcccaacag actgagttgg     540
gggctgcggc tggcggatgt cggagcaaag gatcacttca agagcccaga tccggttggt     600
ccattgccaa tggatctaga ttcggcacct tgatctcgat cactgagaca tggtgagttg     660
cccggacgca ccacaactcc ccctgtgtca ttgagtcccc atatgcgtct tctcagcgtg     720
caactctgag acggattagt cctcacgatg aaattaactt ccagcttaag ttcgtagcct     780
tgaatgagtg aagaaatttc aaaaacaaac tgagtagagg tcttgagcag ctggggtggt     840
acgcccctcc tcgactcttg ggacatcgta cggcagagaa tcaacggatt cacacctttg     900
ggtcgagatg agctgatctc gacagatacg tgcttcacca gctgcagc taccttttgcc     960
caaccattgc gttccaggat cttgatctac atcaccgcag cacccgagcc aggacggaga    1020
gaacaatccg gccacagagc agcaccgcct tccaactctg ctcctggcaa cgtcacacaa    1080
cctgatatta gatatccacc tgggtgattg ccattgcaga gaggtggcag ttggtgatac    1140
cgactggcca tgcaagacgc ggccgggcta gctgaaatgt ccccgagagg acaattggga    1200
gcgtctatga cggcgtggag acgacgggaa aggactcagc cgtcatgttg tgttgccaat    1260
ttgagattgt tgaccgggaa agggggggacg aagaggatgg ctgggtgagg tggtattggg    1320
aggatgcatc attcgactca gtgagcgatg tagagctcca agaatataaa tatccctttct    1380

```
ctgtcttctc aaaatctcct tccatcttgt ccttcatcag caccagagcc agcctgaaca    1440
cctccagtca acttcccta ccagtacatc tgaatcaaca tccattcttt gaaatctcac    1500
cacaaccacc atcttcttca aaatgaagtt cttcgccatc gccgctctct ttgccgccgc    1560
tgccgttgcc cagcctctcg aggaccgcag caacggcaac ggcaatgttt gccctccgg    1620
cctcttcagc aaccccagt gctgtgccac ccaagtcctt ggcctcatcg gccttgactg    1680
caaagtccgt aagttgagcc ataacataag aatcctcttg acggaaatat gccttctcac    1740
tcctttaccc ctgaacagcc tcccagaacg tttacgacgg caccgacttc cgcaacgtct    1800
gcgccaaaac cggcgcccag cctctctgct gcgtggcccc cgttgtaagt tgatgcccca    1860
gctcaagctc cagtctttgg caaacccatt ctgacaccca gactgcaggc cggccaggct    1920
cttctgtgcc agaccgccgt cggtgcttga atgcccgcc cggggtcaag gtgtgcccgt    1980
gagaaagccc acaaagtgtt gatgaggacc atttccggta ctgggaaagt tggctccacg    2040
tgtttgggca ggtttgggca agttgtgtag atattccatt cgtacgccat tcttattctc    2100
caatatttca gtacactttt cttcataaat caaaaagact gctattctct ttgtgacatg    2160
ccggaaggga acaattgctc ttggtctctg ttatttgcaa gtaggagtgg gagattcgcc    2220
ttagagaaag tagagaagct gtgcttgacc gtggtgtgac tcgacgagga tggactgaga    2280
gtgttaggat taggtcgaac gttgaagtgt atacaggatc gtctggcaac ccacggatcc    2340
tatgacttga tgcaatggtg aagatgaatg acagtgtaag aggaaaagga aatgtccgcc    2400
ttcagctgat atccacgcca atgatacagc gatatacctc caatatctgt gggaacgaga    2460
catgacatat ttgtgggaac aacttcaaac agcgagccaa gacctcaata tgcacatcca    2520
aagccaaaca ttggcaagac gagagacagt cacattgtcg tcgaaagatg gcatcgtacc    2580
caaatcatca gctctcatta tcgcctaaac cacagattgt ttgccgtccc ccaactccaa    2640
aacgttacta caaagacat gggcgaatgc aaagacctga agcaaaccc ttttgcgac    2700
tcaattccct cctttgtcct cggaatgatg atccttcacc aagtaaaaga aaagaagat    2760
tgagataata catgaaaagc acaacggaaa cgaaagaacc aggaaaagaa taaatctatc    2820
acgcaccttg tccccacact aaaagcaaca ggggggtaa atgaaat    2868
```

<210> SEQ ID NO 4
<211> LENGTH: 97
<212> TYPE: PRT
<213> ORGANISM: Trichoderma reesei

<400> SEQUENCE: 4

```
Met Lys Phe Phe Ala Ile Ala Ala Leu Phe Ala Ala Ala Val Ala
1               5                   10                  15

Gln Pro Leu Glu Asp Arg Ser Asn Gly Asn Gly Asn Val Cys Pro Pro
            20                  25                  30

Gly Leu Phe Ser Asn Pro Gln Cys Cys Ala Thr Gln Val Leu Gly Leu
        35                  40                  45

Ile Gly Leu Asp Cys Lys Val Pro Ser Gln Asn Val Tyr Asp Gly Thr
    50                  55                  60

Asp Phe Arg Asn Val Cys Ala Lys Thr Gly Ala Gln Pro Leu Cys Cys
65                  70                  75                  80

Val Ala Pro Val Ala Gly Gln Ala Leu Leu Cys Gln Thr Ala Val Gly
                85                  90                  95

Ala
```

<210> SEQ ID NO 5
<211> LENGTH: 945
<212> TYPE: DNA
<213> ORGANISM: Schizophyllum commune

<400> SEQUENCE: 5

```
agtcgaacac cccagttcaa ctaccccagc ccttccttcc ttcgctatcc ttccttacaa       60
cctgctcgcc atgttcgccc gtctcccccgt cgtgttcctc tacgccttcg tcgcgttcgg      120
cgccctcgtc gctgccctcc caggtggcca cccgggcacg acgtacgtcg acctctcacc      180
gtcctctaat gtcttgctga tgaagccccg tatagcacgc cgccggttac gacgacggtg      240
acggtgacca cggtgagtag ctttctcgcc gtcgacgact cgaacgcatt ggctaatttt      300
tgctcatagc cgccctcgac gacgaccatc gccgccggtg gcacgtgtac tacggggtcg      360
ctctcttgct gcaaccaggt tcaatcggta cgtacatcaa agcggcacga ccaggcatct      420
cagctgacgg ccacatcgta caggcgagca gcagccctgt taccgccctc ctcggcctgc      480
tcggcattgt cctcagcgac ctcaacgttc tcgttggcat cagctgctct cccctcactg      540
tgagatcttt ttgttcactg tcccaattac tgcgcactga cagactttgc caggtcatcg      600
gtgtcggagg cagcggctgt tcggcgcaga ccgtctgctg cgaaaacacc caattcgtat      660
gtatactttc catgcgtgtc cctttctccg ctaatcatct gtagaacggg ctgatcaaca      720
tcggttgcac cccatcaac atcctctgag caggtgaacg cgcctgtcgg tgggatattc       780
gggcgacggg agcctcgggc aatctgagcc tcgttactgc ctagcaaatt cggaatccct      840
tcgatgtcat agggtcgcgg acaagtgatc gtcttgctac atactccaag gtgttgactc      900
attccctcag ataatgaaca ttgttgttgt tgttgtttgt tctct                     945
```

<210> SEQ ID NO 6
<211> LENGTH: 136
<212> TYPE: PRT
<213> ORGANISM: Schizophyllum commune

<400> SEQUENCE: 6

```
Met Phe Ala Arg Leu Pro Val Val Phe Leu Tyr Ala Phe Val Ala Phe
1               5                   10                  15

Gly Ala Leu Val Ala Ala Leu Pro Gly Gly His Pro Gly Thr Thr Thr
            20                  25                  30

Pro Pro Val Thr Thr Val Thr Val Thr Thr Pro Pro Ser Thr Thr
        35                  40                  45

Thr Ile Ala Ala Gly Gly Thr Cys Thr Thr Gly Ser Leu Ser Cys Cys
    50                  55                  60

Asn Gln Val Gln Ser Ala Ser Ser Ser Pro Val Thr Ala Leu Leu Gly
65                  70                  75                  80

Leu Leu Gly Ile Val Leu Ser Asp Leu Asn Val Leu Val Gly Ile Ser
                85                  90                  95

Cys Ser Pro Leu Thr Val Ile Gly Val Gly Ser Gly Cys Ser Ala
            100                 105                 110

Gln Thr Val Cys Cys Glu Asn Thr Gln Phe Asn Gly Leu Ile Asn Ile
        115                 120                 125

Gly Cys Thr Pro Ile Asn Ile Leu
            130                 135
```

<210> SEQ ID NO 7
<211> LENGTH: 776
<212> TYPE: DNA

<213> ORGANISM: Neurospora crassa

<400> SEQUENCE: 7

| | | | | |
|---|---|---|---|---|
| atcatcagca tcaacatctt cacttcacaa catcttctca accttccaac tcaccttcca | 60 |
| aaccaccttc aaaaccaact cccagcttct ttcagcaaac ccccaaccgc caaaatgcag | 120 |
| ttcaccagcg tcttcaccat cctcgccatt gccatgaccg ccgctgcggc cccggctgag | 180 |
| gttgttcccc gcgccaccac catcggcccc aacacctgct ccatcgacga ctacaagcct | 240 |
| tactgctgcc agtctatgtc cggccccgcc ggctcccctg gtctcctcaa cctcatcccc | 300 |
| gtcgacctca gcgcctcgct cggctgcgtt gtcggtgtca tcggctccca atgtggtgcc | 360 |
| agcgtcaagt gctgcaagga cgatgttacc aacaccggca actccttcct catcatcaac | 420 |
| gctgccaact cgttgccta agtgtttacg cggcaacagc gcaaagtcta ggcaatgcct | 480 |
| tgttctcaac gctgctgcca gtccagcacc cccttctgc agcaaggagc cccttctgc | 540 |
| tggactggca gcacaacgag ctgctactac aacacaagca tcatgcctgg acgcaacaga | 600 |
| agccgataat cttggggttt ggttttgggg gatgaaggtg atgagttgat ggattggatc | 660 |
| gatatcttac aatgcgtgtc tcttcctgtt aagatctgct ttactatttt cctatttcct | 720 |
| tttacacata gctatgtatc actaaggcct ggtgattaat acactctctt aaccct | 776 |

<210> SEQ ID NO 8
<211> LENGTH: 108
<212> TYPE: PRT
<213> ORGANISM: Neurospora crassa

<400> SEQUENCE: 8

Met Gln Phe Thr Ser Val Phe Thr Ile Leu Ala Ile Ala Met Thr Ala
1               5                   10                  15

Ala Ala Ala Pro Ala Glu Val Val Pro Arg Ala Thr Thr Ile Gly Pro
            20                  25                  30

Asn Thr Cys Ser Ile Asp Asp Tyr Lys Pro Tyr Cys Cys Gln Ser Met
        35                  40                  45

Ser Gly Pro Ala Gly Ser Pro Gly Leu Leu Asn Leu Ile Pro Val Asp
    50                  55                  60

Leu Ser Ala Ser Leu Gly Cys Val Val Gly Val Ile Gly Ser Gln Cys
65                  70                  75                  80

Gly Ala Ser Val Lys Cys Cys Lys Asp Asp Val Thr Asn Thr Gly Asn
                85                  90                  95

Ser Phe Leu Ile Ile Asn Ala Ala Asn Cys Val Ala
            100                 105

<210> SEQ ID NO 9
<211> LENGTH: 453
<212> TYPE: DNA
<213> ORGANISM: Talaromyces thermophilus

<400> SEQUENCE: 9

| | | | | |
|---|---|---|---|---|
| atgaagttcg ccggtgtctt gcttgctgtc gccgctgcgg cgactgccct gccaaacgtc | 60 |
| ggtcccagtg ggaagacggc tcacaagccg caccaggagc ctttctggcc tgtgcagcag | 120 |
| gacgtgaccg tggaacaggc caaggctatc tgtggtgaag caaccaggt cgcttgctgc | 180 |
| aacgaggtca gctacgcggg cgacaccacc gaaatcgcga ccggccccct ggctggcacc | 240 |
| ctcaaggacc tgctcggcgg caagaacggg gccaagggcc tgggtctctt cgacaagtgc | 300 |
| tcgcgtctca atgtcgatct cctgcttggc ctgtcgagcc tcatcaacca agaatgcaag | 360 |

```
cagcacattg cctgctgcca gggcaacgag gccgattcct ccaacgacct catcggtctc    420
aacattcctt gcattgccct tggctcgctg ctg                                 453

<210> SEQ ID NO 10
<211> LENGTH: 151
<212> TYPE: PRT
<213> ORGANISM: Talaromyces thermophilus

<400> SEQUENCE: 10

Met Lys Phe Ala Gly Val Leu Leu Ala Val Ala Ala Ala Thr Ala
1               5                   10                  15

Leu Pro Asn Val Gly Pro Ser Gly Lys Thr Ala His Lys Pro His Gln
            20                  25                  30

Glu Pro Phe Trp Pro Val Gln Gln Asp Val Thr Val Glu Gln Ala Lys
        35                  40                  45

Ala Ile Cys Gly Glu Gly Asn Gln Val Ala Cys Cys Asn Glu Val Ser
    50                  55                  60

Tyr Ala Gly Asp Thr Thr Glu Ile Ala Thr Gly Pro Leu Ala Gly Thr
65                  70                  75                  80

Leu Lys Asp Leu Leu Gly Gly Lys Asn Gly Ala Lys Gly Leu Gly Leu
                85                  90                  95

Phe Asp Lys Cys Ser Arg Leu Asn Val Asp Leu Leu Leu Gly Leu Ser
            100                 105                 110

Ser Leu Ile Asn Gln Glu Cys Lys Gln His Ile Ala Cys Cys Gln Gly
        115                 120                 125

Asn Glu Ala Asp Ser Ser Asn Asp Leu Ile Gly Leu Asn Ile Pro Cys
    130                 135                 140

Ile Ala Leu Gly Ser Leu Leu
145                 150
```

STABILIZATION OF BIOMIMETIC MEMBRANES

CROSS REFERENCE TO RELATED APPLICATIONS

This application is a divisional of U.S. patent application Ser. No. 14/436,216 filed Apr. 16, 2015, now pending, which is a national stage filing of PCT Application No. PCT/US13/65746 filed Oct. 18, 2013, which claims the benefit of U.S. provisional application No. 61/716,351, filed Oct. 19, 2012, which are each hereby incorporated herein by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named 20181210_NB40357USPCD_SequenceListing.txt created on Dec. 10, 2018 and having a size of 14 kilobytes and is filed concurrently with the specification. The sequence listing contained in this ASCII formatted document is part of the specification and is herein incorporated by reference in its entirety.

BACKGROUND

Biological membrane proteins have a large variety of functions, including acting as pumps, channels, valves, energy transducers, and mechanical, thermal, and electrical sensors, among many others. Membrane proteins play a role in many important cellular activities including energy conversion, cell signaling, cell-cell interactions, cell adhesion, cell migration, protein trafficking, viral fusion, neural synaptic activities and ion and metabolite transport. Membrane proteins are embedded in the lipid bilayer of the cell membrane and are comprised of both hydrophobic and hydrophilic moieties. Membranes comprising an artificial lipid bilayer with incorporated functional membrane proteins, such as ion channel peptides and transmembrane proteins are useful in a diverse range of technical applications. Since these proteins are nanometers in size and highly efficient, they are highly attractive for use in artificial devices. However, their natural lipid membrane environment suffers from shortcomings such as low strength, necessity of an aqueous environment, and susceptibility to chemical or bacterial degradation. Another common problem for such membranes is the need for stability of the membranes over time and against mechanical, electrical and chemical impacts.

Because membrane proteins possess both hydrophobic and hydrophilic regions, they are difficult to solubilize, extract and purify. One of the challenges posed by membrane proteins is that they are subject to rapid denaturation and/or aggregation in solution. Despite the availability of a wide range of surfactants, few provide increased and/or prolonged stability of membrane proteins in solution and/or in the membranes. Therefore, there remains a need in the art for surfactants capable of increasing the stability of membrane proteins. The present disclosure provides methods, compositions, kits and apparatuses to address these problems.

SUMMARY OF THE INVENTION

The present invention provides methods, compositions, kits and apparatuses for stabilizing membranes and membrane proteins using hydrophobin.

In some embodiments, the invention provides methods of stabilizing a biomimetic membrane by adding one or more hydrophobins to the biomimetic membrane. In some embodiments, the invention provides compositions comprising a biomimetic membrane and one or more hydrophobins. In some embodiments, the biomimetic membrane further comprises a membrane protein.

In some embodiments, the hydrophobin is a hydrophobin having the general formula (I):

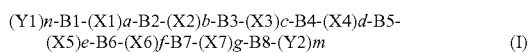

where:
m and n are independently 0 to 2000; B1, B2, B3, B4, B5, B6, B7 and B8 are each independently amino acids selected from Cys, Leu, Ala, Pro, Ser, Thr, Met or Gly, at least 6 of the residues B1 through B8 being Cys; X1, X2, X3, X4, X5, X6, X7, Y1 and Y2 independently represent any amino acid; a is 1 to 50; b is 0 to 5; c is 1 to 100; d is 1 to 100; e is 1 to 50; f is 0 to 5; and g is 1 to 100.

In some embodiments, the biomimetic membrane further comprises a membrane protein. In some embodiments, the membrane protein is an aquaporin. In some embodiments, the aquaporin is AQP1. In some embodiments, the aquaporin is of plant origin. In some embodiments, the aquaporin is selected from the group consisting of a Tonoplast Intrinsic Protein, a Plasma Membrane Intrinsic Protein, and a Nodulin-26 like Intrinsic Protein aquaporin, and mixtures and hybrids thereof. In some embodiments, the aquaporin is an aquaglyceroporin (GLpF). In some embodiments, the GLpF is selected from the group consisting of a GLPA channel, a GLPB1 channel, a GLPB2 channel, a GLPB3 channel, and a GLPY2 channel, and mixtures and hybrids thereof. In some embodiments, the aquaporin water channel is aquaporin Z (AqpZ), which is derived from *E. Coli*. In some embodiments, the aquaporin comprises a modified sequence.

In some embodiments, the hydrophobin has a sequence of between 40 and 120 amino acids in the hydrophobin core. In some embodiments, the hydrophobin has the general formula (II):

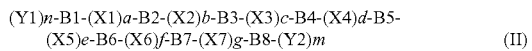

where:
m and n are independently 0 to 20; B1, B2, B3, B4, B5, B6, B7 and B8 are each independently amino acids selected from Cys, Leu, Ala, Pro, Ser, Thr, Met or Gly, at least 7 of the residues B1 through B8 being Cys; a is 3 to 25; b is 0 to 2; c is 5 to 50; d is 2 to 35; e is 2 to 15; f is 0 to 2; and g is 3 to 35.

In some embodiments, the hydrophobin has the general formula (III):

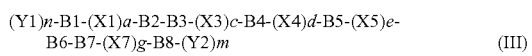

where:
m and n are independently 0 to 20; B1, B2, B3, B4, B5, B6, B7 and B8 are each independently amino acids selected from Cys, Leu, Ala, Pro, Ser, Thr, Met or Gly, at least 7 of the residues B1 through B8 being Cys; a is 5 to 15; c is 5 to 40; d is 4 to 23; e is 5 to 12; and g is 6 to 21.

In some embodiments, all 8 of the residues B1 through B8 are Cys.

In some embodiments, the hydrophobin is a hydrophobin fusion protein.

In some embodiments, the hydrophobin is obtained or obtainable from a filamentous fungus. In some embodiments, the hydrophobin is obtained or obtainable from a fungus of genus selected from the group consisting of *Cladosporium, Ophistoma, Cryphonectria, Trichoderma, Gibberella, Neurospora, Maganaporthe, Hypocrea, Xanthoria, Emericella, Aspergillus, Paracoccioides, Metarhizium, Pleurotus, Coprinus, Dicotyonema, Flammulina, Schizophyllum, Agaricus, Pisolithus, Tricholoma, Pholioka, Talaromyces* and *Agrocybe.*

In some embodiments, the hydrophobin is generated in situ in the composition.

In some embodiments, the hydrophobin causes the equilibrium surface tension at a water/air interface to reduce to below 70 mN/m, below 50 mN/m or below 40 mN/m. In some embodiments, the hydrophobin causes the surface shear elasticity at a water/air interface to increase to 0.3-0.6 N/m or higher.

In some embodiments, the hydrophobin causes at least 1.2 fold increase in stability of the biomimetic membrane compared to the stability in the absence of the hydrophobin. In some embodiments, the hydrophobin provides a decrease in an equilibrium surface tension at the biomimetic membrane below 50 mN/m. In some embodiments, the hydrophobin causes the surface shear elasticity at the biomimetic membrane to increase to 0.3-0.6 N/m or higher.

In some embodiments, the hydrophobin is a Class II hydrophobin. In some embodiments, the hydrophobin is a Class II hydrophobin having the general formula (IV):

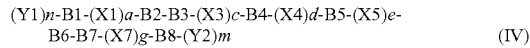
(Y1)n-B1-(X1)a-B2-B3-(X3)c-B4-(X4)d-B5-(X5)e-B6-B7-(X7)g-B8-(Y2)m     (IV)

where:
m and n are independently 0 to 200; B1, B2, B3, B4, B5, B6, B7 and B8 are each independently amino acids selected from Cys, Leu, Ala, Ser, Thr, Met or Gly, at least 6 of the residues B1 through B8 being Cys; a is 6 to 12; c is 8 to 16; d is 2 to 20; e is 4 to 12; and g is 5 to 15.

In some embodiments, the hydrophobin is a Class II hydrophobin having the general formula (V):

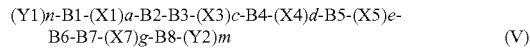
(Y1)n-B1-(X1)a-B2-B3-(X3)c-B4-(X4)d-B5-(X5)e-B6-B7-(X7)g-B8-(Y2)m     (V)

where:
m and n are independently 0 to 10; B1, B2, B3, B4, B5, B6, B7 and B8 are each independently amino acids selected from Cys, Leu or Ser, at least 7 of the residues B1 through B8 being Cys; a is 7 to 11; c is 11; d is 4 to 18; e is 6 to 10; and g is 7 to 10.

In some embodiments, all 8 of the residues B1 through B8 are Cys. In some embodiments, the group (X3)c comprises the sequence motif ZZXZ, where Z is an aliphatic amino acid; and X is any amino acid.

In some embodiments, the hydrophobin is present in a concentration of 0.1 μM-50 mM. In some embodiments, the hydrophobin is present in a concentration of 0.1-20% by weight of the total weight of the composition.

In some embodiments, the hydrophobin is selected from the groups consisting of HFBII (SEQ ID NO: 2), HFBI (SEQ ID NO: 4), SC3 (SEQ ID NO: 6), EAS (SEQ ID NO: 8) and TT1 (SEQ ID NO: 10), or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any thereof. In some embodiments, the hydrophobin is "HFBII" (SEQ ID NO: 2), or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core thereof.

In some embodiments, the invention provides methods for preparing a water filtrate. In some embodiments, the invention provides methods for preparing a water filtrate comprising filtering an aqueous solution through a biomimetic membrane comprising hydrophobin. In some embodiments, the invention provides methods for preparing a water filtrate comprising filtering an aqueous solution through a membrane comprising a sandwich construction having at least two permeable support layers separated by at least one lipid bilayer comprising functional aquaporin water channels and one or more hydrophobins.

In some embodiments, the invention provides methods for preparing a water filtrate comprising filtering an aqueous solution through a membrane comprising one or more vesicles (e.g. lipid and/or polymer vesicles) comprising functional aquaporin water channels and one or more hydrophobins. In some embodiments, the one or more vesicles are supported in a substrate (e.g. a microporous substrate). In some embodiments, the membrane comprises one or more vesicles (e.g. lipid and/or polymer vesicles) comprising functional aquaporin water channels and one or more hydrophobins, wherein the vesicles are incorporated into a thin film layer (e.g. amine functional layer) and are supported in a microporous substrate.

In some embodiments, the invention provides membranes capable of filtering water, comprising aquaporin water transport proteins and one or more hydrophobins.

In some embodiments, the invention provides methods of preparing a pure water filtrate, comprising filtering an aqueous solution through a membrane comprising aquaporin water transport proteins and one or more hydrophobins.

In some embodiments, the invention provides methods for the production of salinity power using pressure retarded osmosis, the method comprising utilizing a biomimetic membrane comprising one or more hydrophobins and aquaporin water channels to increase hydrostatic pressure, and using the increase in hydrostatic pressure as a source of salinity power.

BRIEF DESCRIPTION OF THE DRAWINGS

The features of the invention are set forth with particularity below. A better understanding of the features and advantages of the present invention will be obtained by reference to the following detailed description that sets forth illustrative embodiments, in which the principles of the invention are utilized, and the accompanying drawings of which:

FIGS. 5, 6, 7A-7B, 8, 9, 10, 11, 12, 13 and 14 show SEQ IDs 1-10, respectively.

DETAILED DESCRIPTION OF THE INVENTION

Figure 1:
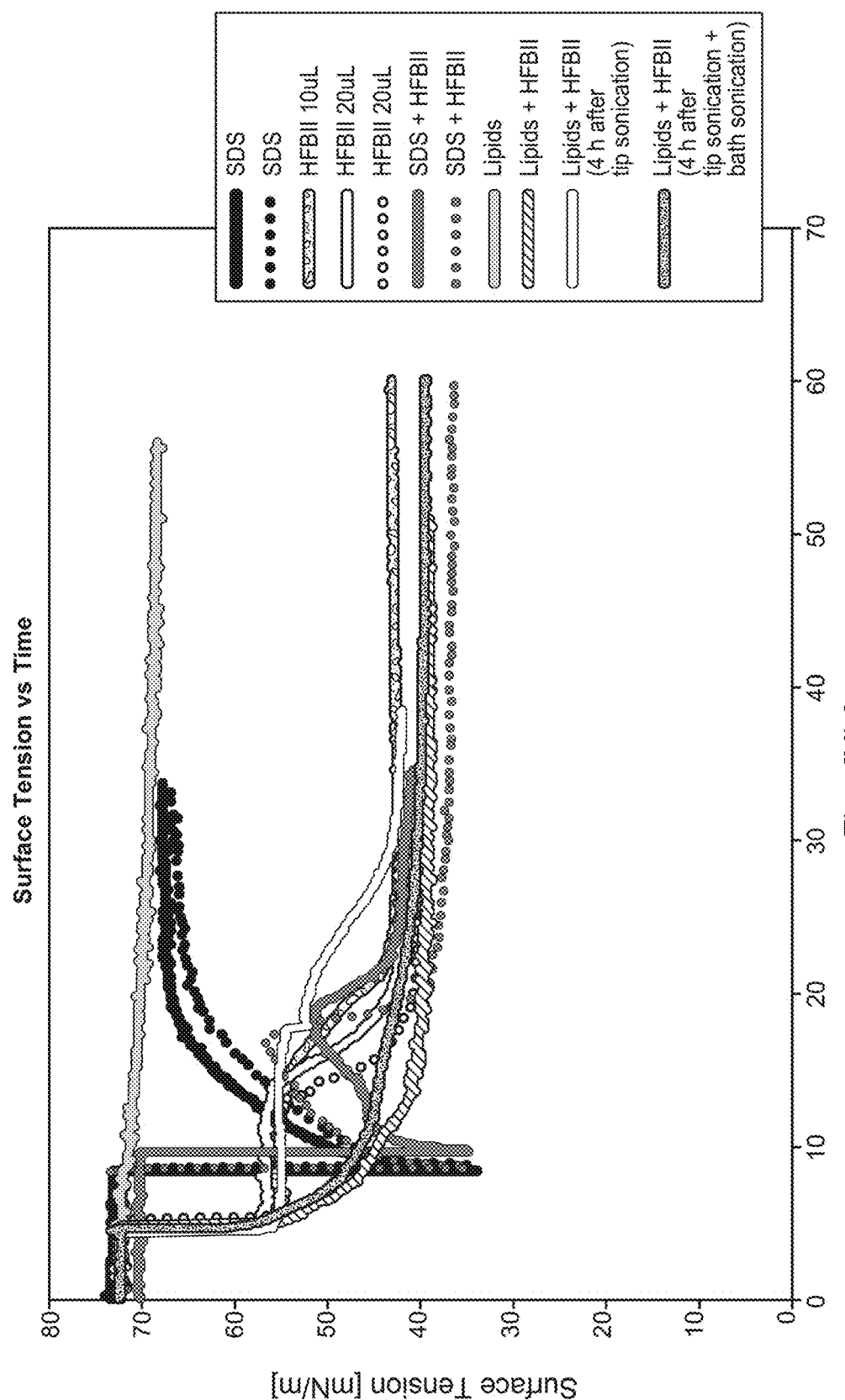
FIG. 1 depicts a graph showing surface tension vs. time of different tested samples.

The present disclosure provides methods, compositions, kits and apparatuses for stabilizing a membrane protein, a membrane (e.g. a biomimetic membrane), and/or a membrane comprising a membrane protein using one or more hydrophobins. In some embodiments, the present invention provides methods, compositions, kits and apparatuses for stabilizing a biomimetic membrane using one or more hydrophobins In some embodiments, the present invention provides methods, compositions, kits and apparatuses for stabilizing membrane protein using one or more hydrophobins. In some embodiments, the present invention provides methods, compositions, kits and apparatuses for stabilizing a biomimetic membrane containing a membrane protein using one or more hydrophobins.

Unless otherwise explained, all technical and scientific terms used herein have the same meaning as commonly understood by one of ordinary skill in the art to which this disclosure belongs. All references cited herein are all incorporated by reference herein in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below.

Hydrophobins

In this specification the term "hydrophobin" is defined as meaning a polypeptide capable of self-assembly at a hydrophilic/hydrophobic interface, and having the general formula (I):

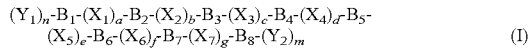

(I)

wherein: m and n are independently 0 to 2000; $B_1$, $B_2$, $B_3$, $B_4$, $B_5$, $B_6$, $B_7$ and $B_8$ are each independently amino acids selected from Cys, Leu, Ala, Pro, Ser, Thr, Met or Gly, at least 6 of the residues $B_1$ through $B_8$ being Cys; $X_1$, $X_2$, $X_3$, $X_4$, $X_5$, $X_6$, $X_7$, $Y_1$ and $Y_2$ independently represent any amino acid; a is 1 to 50; b is 0 to 5; c is 1 to 100; d is 1 to 100; e is 1 to 50; f is 0 to 5; and g is 1 to 100.

In some embodiments, the hydrophobin has a sequence of between 40 and 120 amino acids in the hydrophobin core. In some embodiments, the hydrophobin has a sequence of between 45 and 100 amino acids in the hydrophobin core. In some embodiments, the hydrophobin has a sequence of between 50 and 90, preferably 50 to 75, or 55 to 65 amino acids in the hydrophobin core. The term "the hydrophobin core" means the sequence beginning with the residue $B_1$ and terminating with the residue $B_8$.

In the formula (I), at least 6, or at least 7, or all 8 of the residues $B_1$ through $B_8$ are Cys.

In the formula (I), in some embodiments m is suitably 0 to 500, or 0 to 200, or 0 to 100, or 0 to 20, or 0 to 10, or 0 to 5, or 0.

In the formula (I), in some embodiments n is suitably 0 to 500, or 0 to 200, or 0 to 100, or 0 to 20, or 0 to 10, or 0 to 3.

In the formula (I), in some embodiments, a is 3 to 25, or 5 to 15. In one embodiment, a is 5 to 9.

In the formula (I), in some embodiments, b is 0 to 2, or preferably 0.

In the formula (I), in some embodiments, c is 5 to 50, or 5 to 40. In some embodiments, c is 11 to 39.

In the formula (I), in some embodiments, d is 2 to 35, or 4 to 23. In some embodiments, d is 8 to 23.

In the formula (I), in some embodiments, e is 2 to 15, or 5 to 12. In some embodiments, e is 5 to 9.

In the formula (I), in some embodiments, f is 0 to 2, or 0.

In the formula (I), in some embodiments, g is 3 to 35, or 6 to 21. In one embodiment, g is 6 to 18.

In some embodiments, the hydrophobins used in the present invention have the general formula (II):

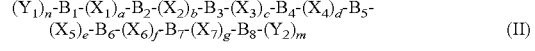

(II)

wherein: m and n are independently 0 to 20; $B_1$, $B_2$, $B_3$, $B_4$, $B_5$, $B_6$, $B_7$ and $B_8$ are each independently amino acids selected from Cys, Leu, Ala, Pro, Ser, Thr, Met or Gly, at least 7 of the residues $B_1$ through $B_8$ being Cys; a is 3 to 25; b is 0 to 2; c is 5 to 50; d is 2 to 35; e is 2 to 15; f is 0 to 2; and g is 3 to 35.

In the formula (II), at least 7, or all 8 of the residues $B_1$ through $B_8$ are Cys.

In some embodiments, the hydrophobins used in the present invention have the general formula (III):

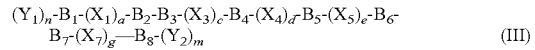

(III)

wherein: m and n are independently 0 to 20; $B_1$, $B_2$, $B_3$, $B_4$, $B_5$, $B_6$, $B_7$ and $B_8$ are each independently amino acids selected from Cys, Leu, Ala, Pro, Ser, Thr, Met or Gly, at least 7 of the residues $B_1$ through $B_8$ being Cys; a is 5 to 15; c is 5 to 40; d is 4 to 23; e is 5 to 12; and g is 6 to 21.

In the formula (III), at least 7, or 8 of the residues $B_1$ through $B_8$ are Cys.

In the formulae (I), (II) and (III), when 6 or 7 of the residues $B_1$ through $B_8$ are Cys, it is preferred that the residues $B_3$ through $B_7$ are Cys.

In the formulae (I), (II) and (III), when 7 of the residues $B_1$ through $B_8$ are Cys, in some embodiments: (a) $B_1$ and $B_3$ through $B_8$ are Cys and $B_2$ is other than Cys; (b) $B_1$ through $B_7$ are Cys and $B_8$ is other than Cys, (c) $B_1$ is other than Cys and $B_2$ through $B_8$ are Cys. When 7 of the residues $B_1$ through $B_8$ are Cys, it is preferred that the other residue is Ser, Pro or Leu. In some embodiments, $B_1$ and $B_3$ through $B_8$ are Cys and $B_2$ is Ser. In some embodiments, $B_1$ through $B_7$ are Cys and $B_8$ is Leu. In further embodiments, $B_1$ is Pro and $B_2$ through $B_8$ are Cys.

The cysteine residues of the hydrophobins used in the present invention may be present in reduced form or form disulfide (—S—S—) bridges with one another in any possible combination. In some embodiments, when all 8 of the residues $B_1$ through $B_8$ are Cys, disulfide bridges may be formed between one or more (preferably at least 2, more preferably at least 3, most preferably all 4) of the following pairs of cysteine residues: $B_1$ and $B_6$; $B_2$ and $B_5$; $B_3$ and $B_4$; $B_7$ and $B_8$. In some embodiments, when all 8 of the residues $B_1$ through $B_8$ are Cys, disulfide bridges may be formed between one or more (at least 2, or at least 3, or all 4) of the following pairs of cysteine residues: $B_1$ and $B_2$; $B_3$ and $B_4$; $B_5$ and $B_6$; $B_7$ and $B_8$.

Examples of specific hydrophobins useful in the present invention include those described and exemplified in the following publications: Linder et al., *FEMS Microbiology Rev.* 2005, 29, 877-896; Kubicek et al., *BMC Evolutionary Biology*, 2008, 8, 4; Sunde et al., *Micron*, 2008, 39, 773-784; Wessels, *Adv. Micr. Physiol.* 1997, 38, 1-45; Wösten, *Annu. Rev. Microbiol.* 2001, 55, 625-646; Hektor and Scholtmeijer, *Curr. Opin. Biotech.* 2005, 16, 434-439; Szilvay et al., *Biochemistry*, 2007, 46, 2345-2354; Kisko et al. *Langmuir,* 2009, 25, 1612-1619; Blijdenstein, *Soft Matter,* 2010, 6, 1799-1808; Wösten et al., *EMBO J.* 1994, 13, 5848-5854; Hakanpää et al., *J. Biol. Chem.,* 2004, 279, 534-539; Wang et al.; *Protein Sci.,* 2004, 13, 810-821; De Vocht et al., *Biophys. J.* 1998, 74, 2059-2068; Askolin et al., *Biomacromolecules* 2006, 7, 1295-1301; Cox et al.; *Langmuir,* 2007, 23, 7995-8002; Linder et al., *Biomacromolecules* 2001, 2, 511-517; Kallio et al. *J. Biol. Chem.,* 2007, 282, 28733-28739; Scholtmeijer et al., *Appl. Microbiol. Biotechnol.,* 2001, 56, 1-8; Lumsdon et al., *Colloids & Surfaces B: Biointerfaces,* 2005, 44, 172-178; Palomo et al., *Biomacromolecules* 2003, 4, 204-210; Kirkland and Keyhani, *J. Ind. Microbiol. Biotechnol.*, Jul. 17 2010 (e-publication); Stübner et al., *Int. J. Food Microbiol.,* 30 Jun. 2010 (e-publication); Laaksonen et al. *Langmuir,* 2009, 25, 5185-5192; Kwan et al. *J. Mol. Biol.* 2008, 382, 708-720; Yu et al. *Microbiology,* 2008, 154, 1677-1685; Lahtinen et al. *Protein Expr. Purif.,* 2008, 59, 18-24; Szilvay et al., *FEBS Lett.,* 2007, 5811, 2721-2726; Hakanpää et al., *Acta Crystallogr. D. Biol. Crystallogr.* 2006, 62, 356-367; Scholtmeijer et al., *Appl. Environ. Microbiol.,* 2002, 68, 1367-1373; Yang et al, *BMC Bioinformatics,* 2006, 7 Supp. 4, S16; WO 01/57066; WO 01/57528; WO 2006/082253; WO 2006/103225; WO 2006/103230; WO 2007/014897; WO 2007/087967; WO 2007/087968; WO 2007/030966; WO 2008/019965; WO 2008/107439; WO 2008/110456; WO 2008/116715; WO 2008/120310; WO 2009/050000; US 2006/0228484; and EP 2042156A; the contents of which are incorporated herein by reference.

In some embodiments, the hydrophobin is a polypeptide selected from SEQ ID NOs: 2, 4, 6 8 or 10, or a polypeptide having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any thereof and retaining the above-described self-assembly property of hydrophobins.

a. Sources of Hydrophobin

In one embodiment, the hydrophobin is obtained or obtainable from a microorganism. In some embodiments, the microorganism is a bacteria or a fungus, more preferably a fungus. In some embodiments, the hydrophobin is obtained or obtainable from a filamentous fungus.

In some embodiments, the hydrophobin is obtained or obtainable from fungi of the genera *Cladosporium* (particularly *C. fulvum* or *C. herbarum*), *Ophistoma* (particularly *O. ulmi*), *Cryphonectria* (particularly *C. parasitica*), *Trichoderma* (particularly *T. harzianum, T. longibrichiatum, T. asperellum, T. Koningiopsis, T. aggressivum, T. sfromaticum* or *T. reesei*), *Gibberella* (particularly *G. moniliformis*), *Neurospora* (particularly *N. crassa*), *Maganaporthe* (particularly *M. grisea*), *Hypocrea* (particularly *H. jecorina, H. afroviridis, H. vixens* or *H lixii*), *Xanthoria* (particularly *X. ectanoides* and *X. parietina*), *Emericella* (particularly *E. nidulans*), *Aspergillus* (particularly *A. fumigatus, A. oryzae*), *Paracoccioides* (particularly *P. brasiliensis*), *Metarhizium* (particularly *M. anisoplaie*), *Pleurotus* (particularly *P. ostreatus*), *Coprinus* (particularly *C. cinereus*), *Dicotyonema* (particularly *D. glabratum*), *Flammulina* (particularly *F. velutipes*), *Schizophyllum* (particularly *S. commune*), *Agaricus* (particularly *A. bisporus*), *Pisolithus* (particularly *P. tinctorius*), *Tricholoma* (particularly *T. terreum*), *Pholioka* (particularly *P. nameko*), *Talaromyces* (particularly *T. thermophilus*) or *Agrocybe* (particularly *A. aegerita*).

b. Class I and II Hydrophobias

In the art, hydrophobins are divided into Classes I and II. It is known in the art that hydrophobins of Classes I and II can be distinguished on a number of grounds, including solubility. As described herein, hydrophobins self-assemble at an interface (e.g., a water/air interface) into amphipatic interfacial films. The assembled amphipathic films of Class I hydrophobins are generally re-solubilised only in strong acids (typically those having a $pK_a$ of lower than 4, such as formic acid or trifluoroacetic acid), whereas those of Class II are soluble in a wider range of solvents.

In some embodiments, the hydrophobin is a Class II hydrophobin. In some embodiments, the hydrophobin is a Class I hydrophobin.

In some embodiments, the term "Class II hydrophobin" includes a hydrophobin (as defined and exemplified herein) having the above-described self-assembly property at a water/air interface, the assembled amphipathic films being capable of redissolving to a concentration of at least 0.1% (w/w) in an aqueous ethanol solution (60% v/v) at room temperature. In some embodiments, the term "Class I hydrophobin" includes a hydrophobin (as defined and exemplified herein) having the above-described self-assembly property but which does not have this specified redissolution property.

In some embodiments, the term "Class II hydrophobin" includes a hydrophobin (as defined and exemplified herein) having the above-described self-assembly property at a water/air interface and the assembled amphipathic films being capable of redissolving to a concentration of at least 0.1% (w/w) in an aqueous sodium dodecyl sulphate solution (2% w/w) at room temperature. In some embodiments, the term "Class I hydrophobin" includes a hydrophobin (as defined and exemplified herein) having the above-described self-assembly property but which does not have this specified redissolution property.

Hydrophobins of Classes I and II may also be distinguished by the hydrophobicity/hydrophilicity of a number of regions of the hydrophobin protein.

In some embodiments, the term "Class II hydrophobin" includes a hydrophobin (as defined and exemplified herein) having the above-described self-assembly property and in which the region between the residues $B_3$ and $B_4$, i.e. the moiety $(X_3)_c$, is predominantly hydrophobic. In some embodiments, the term "Class I hydrophobin" includes a hydrophobin (as defined and exemplified herein) having the above-described self-assembly property but in which the region between the residues $B_3$ and $B_4$, i.e. the group $(X_3)_c$, is predominantly hydrophilic.

In some embodiments, the term "Class II hydrophobin" includes a hydrophobin (as defined and exemplified herein) having the above-described self-assembly property and in which the region between the residues $B_7$ and $B_8$, i.e. the moiety $(X_7)_g$, is predominantly hydrophobic. In some embodiments, the term "Class I hydrophobin" includes a hydrophobin (as defined and exemplified herein) having the above-described self-assembly property but in which the region between the residues $B_7$ and $B_8$, i.e. the moiety $(X_7)_g$, is predominantly hydrophilic.

In some embodiments, the term "Class II hydrophobin" includes a hydrophobin (as defined and exemplified herein) having the above-described self-assembly property and in which the region between the residues $B_3$ and $B_4$, i.e. the moiety $(X_3)_c$, is predominantly hydrophobic. In some embodiments, the term "Class I hydrophobin" includes a hydrophobin (as defined and exemplified herein) having the above-described self-assembly property but in which the region between the residues $B_3$ and $B_4$, i.e. the group $(X_3)_c$, is predominantly hydrophilic.

In some embodiments, the term "Class II hydrophobin" includes a hydrophobin (as defined and exemplified herein) having the above-described self-assembly property and in which the region between the residues $B_7$ and $B_8$, i.e. the moiety $(X_7)_g$, is predominantly hydrophobic. In some embodiments, the term "Class I hydrophobin" includes a hydrophobin (as defined and exemplified herein) having the above-described self-assembly property but in which the region between the residues $B_7$ and $B_8$, i.e. the moiety $(X_7)_g$, is predominantly hydrophilic.

The relative hydrophobicity/hydrophilicity of the various regions of the hydrophobin protein can be established by comparing the hydropathy pattern of the hydrophobin using the method set out in Kyte and Doolittle, *J. Mol. Biol.*, 1982, 157, 105-132. A computer program can be used to progressively evaluate the hydrophilicity and hydrophobicity of a protein along its amino acid sequence. For this purpose, the method uses a hydropathy scale (based on a number of experimental observations derived from the literature) comparing the hydrophilic and hydrophobic properties of each of the 20 amino acid side-chains. The program uses a moving-segment approach that continuously determines the average hydropathy within a segment of predetermined length as it advances through the sequence. The consecutive scores are plotted from the amino to the carboxy terminus. At the same time, a midpoint line is printed that corresponds to the grand average of the hydropathy of the amino acid compositions found in most of the sequenced proteins. The method is further described for hydrophobins in Wessels, Adv. Microbial Physiol. 1997, 38, 1-45.

Class II hydrophobins may also be characterized by their conserved sequences.

In one embodiment, the Class II hydrophobins used in the present invention have the general formula (IV):

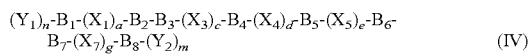
(IV)

wherein: m and n are independently 0 to 200; $B_1$, $B_2$, $B_3$, $B_4$, $B_5$, $B_6$, $B_7$ and $B_8$ are each independently amino acids selected from Cys, Leu, Ala, Ser, Thr, Met or Gly, at least 6 of the residues $B_1$ through $B_8$ being Cys; a is 6 to 12; c is 8 to 16; d is 2 to 20; e is 4 to 12; and g is 5 to 15.

In the formula (IV), in some embodiments, a is 7 to 11.
In the formula (IV), in some embodiments, c is 10 to 12. In some embodiments, c is 11.
In the formula (IV), in some embodiments, d is 4 to 18. In some embodiments, d is 4 to 16.

In the formula (IV), in some embodiments, e is 6 to 10. In some embodiments, e is 9 or 10.
In the formula (IV), in some embodiments, g is 6 to 12. In some embodiments, g is 7 to 10.

In some embodiments, the Class II hydrophobins used in the present invention have the general formula (V):

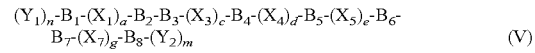
(V)

wherein: m and n are independently 0 to 10; $B_1$, $B_2$, $B_3$, $B_4$, $B_5$, $B_6$, $B_7$ and $B_8$ are each independently amino acids selected from Cys, Leu or Ser, at least 7 of the residues $B_1$ through $B_8$ being Cys; a is 7 to 11; c is 11; d is 4 to 18; e is 6 to 10; and g is 7 to 10.

In the formulae (IV) and (V), in some embodiments, at least 7 of the residues $B_1$ through $B_8$ are Cys, or all 8 of the residues $B_1$ through $B_8$ are Cys.

In the formulae (IV) and (V), in some embodiments, when 7 of the residues $B_1$ through $B_8$ are Cys, it is preferred that the residues $B_3$ through $B_7$ are Cys.

In the formulae (IV) and (V), in some embodiments, when 7 of the residues $B_1$ through $B_8$ are Cys, it is preferred that: (a) $B_1$ and $B_3$ through $B_8$ are Cys and $B_2$ is other than Cys; (b) $B_1$ through $B_7$ are Cys and $B_8$ is other than Cys, or (c) $B_1$ is other than Cys and $B_2$ through $B_8$ are Cys. In some embodiments, when 7 of the residues $B_1$ through $B_8$ are Cys, it is preferred that the other residue is Ser, Pro or Leu. In some embodiments, $B_1$ and $B_3$ through $B_8$ are Cys and $B_2$ is Ser. In some embodiments, $B_1$ through $B_7$ are Cys and $B_8$ is Leu. In some embodiments, $B_1$ is Pro and $B_2$ through $B_8$ are Cys.

In the formulae (IV) and (V), in some embodiments, the group $(X_3)_c$ comprises the sequence motif ZZXZ, wherein Z is an aliphatic amino acid; and X is any amino acid. The term "aliphatic amino acid" means an amino acid selected from the group consisting of glycine (G), alanine (A), leucine (L), isoleucine (I), valine (V) and proline (P).

In some embodiments, the group $(X_3)_c$ comprises the sequence motif selected from the group consisting of LLXV, ILXV, ILXL, VLXL and VLXV. In some embodiments, the group $(X_3)_c$ comprises the sequence motif VLXV.

In the formulae (IV) and (V), in some embodiments, the group $(X_3)_c$ comprises the sequence motif ZZXZZXZ, wherein Z is an aliphatic amino acid; and X is any amino acid. In some embodiments, the group $(X_3)_c$ comprises the sequence motif VLZVZXL, wherein Z is an aliphatic amino acid; and X is any amino acid.

In some embodiments, the hydrophobin is a polypeptide selected from SEQ ID NOs: 2, 4, 6, 8 or 10, or a polypeptide having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any thereof. By "the hydrophobin core" is meant the sequence beginning with the residue $B_1$ and terminating with the residue $B_8$.

In some embodiments, the hydrophobin is obtained or obtainable from fungi of the phylum Ascomycota. In some embodiments, the hydrophobin is obtained or obtainable from fungi of the genera *Cladosporium* (particularly *C. fulvum*), *Ophistoma* (particularly *O. ulmi*), *Cryphonectria* (particularly *C. parasitica*), *Trichoderma* (particularly *T. harzianum, T. longibrichiatum, T. asperellum, T. Koningiopsis, T. aggressivum, T. stromaticum* or *T. reesei*), *Gibberella* (particularly *G. moniliformis*), *Neurospora* (particularly *N. crassa*), *Maganaporthe* (particularly *M. grisea*) or *Hypocrea* (particularly *H. jecorina, H. atroviridis, H. vixens* or *H lixii*).

In some embodiments, the hydrophobin is obtained or obtainable from fungi of the genus Trichoderma (particularly *T. harzianum*, *T. longibrichiatum*, *T. asperellum*, *T. Koningiopsis*, *T. aggressivum*, *T. stromaticum* or *T. reesei*). In some embodiments, the hydrophobin is obtained or obtainable from fungi of the species *T. reesei*.

In some embodiments, the hydrophobin is selected from the group consisting of: (a) HFBII (SEQ ID NO: 2; obtainable from the fungus *Trichoderma reesei*); (b) HFBI (SEQ ID NO: 4; obtainable from the fungus *Trichoderma reesei*); (c) SC3 (SEQ ID NO: 6; obtainable from the fungus *Schizophyllum commune*); (d) EAS (SEQ ID NO: 8; obtainable from the fungus *Neurospora crassa*); and (e) TT1 (SEQ ID NO: 10; obtainable from the fungus *Talaromyces thermophilus*); or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any thereof.

In some embodiments, the hydrophobin is encoded by the polynucleotide selected from the group consisting of: (a) HFBII (SEQ ID NO: 1; obtainable from the fungus *Trichoderma reesei*); (b) HFBI (SEQ ID NO: 3; obtainable from the fungus *Trichoderma reesei*); (c) SC3 (SEQ ID NO: 5; obtainable from the fungus *Schizophyllum commune*); (d) EAS (SEQ ID NO: 7; obtainable from the fungus *Neurospora crassa*); and (e) TT1 (SEQ ID NO: 9; obtainable from the fungus *Talaromyces thermophilus*); or the protein encoded by a polynucleotide which is degenerate as a result of the genetic code to the polynucleotides defined in (a) to (e) above.

In some embodiments, the hydrophobin is "HFBII" (SEQ ID NO: 2; obtainable from *Trichoderma reesei*) or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core thereof.

In some embodiments, the hydrophobin may be present as an initial component of the composition. In another embodiment, the hydrophobin may be generated in situ in the composition (for example, by in situ hydrolysis of a hydrophobin fusion protein).

In some embodiments, the hydrophobin may be replaced wholly or partially with a chaplin. Chaplins are hydrophobin-like proteins which are also capable of self-assembly at a hydrophobic-hydrophilic interface, and are therefore functional equivalents to hydrophobins. Chaplins have been identified in filamentous fungi and bacteria such as Actinomycetes and *Streptomyces*. Unlike hydrophobins, they may have only two cysteine residues and may form only one disulphide bridge. Examples of chaplins are described in WO 01/74864, US 2010/0151525 and US 2010/0099844 and in Talbot, *Curr. Biol.* 2003, 13, R696-R698.

c. Assay

One property of the hydrophobins used in some embodiments of the present invention is the self-assembly property of the hydrophobins at a hydrophilic/hydrophobic interface.

Self-assembly can be detected by adsorbing the protein to polytetrafluoroethylene (TEFLON®) and using Circular Dichroism (CD) to establish the change in secondary structure exemplified by the occurrence of motifs in the CD spectrum corresponding to a newly formed α-helix) (De Vocht et al., *Biophys. J.* 1998, 74, 2059-2068). A full procedure for carrying out the CD spectral analysis can be found in Askolin et al. *Biomacromolecules*, 2006, 7, 1295-1301.

In some embodiments, the hydrophobins used in the present invention are characterized by their effect on the surface properties at an interface, e.g., at an air/water interface. The surface property may be surface tension (especially equilibrium surface tension) or surface shear rheology, particularly the surface shear elasticity (storage modulus).

In some embodiments, the hydrophobin may cause the equilibrium surface tension at a water/air interface to reduce to below 70 mN/m. In some embodiments, the hydrophobin may cause the equilibrium surface tension at a water/air interface to reduce to below 50 mN/m. In some embodiments, the hydrophobin may cause the equilibrium surface tension at a water/air interface to reduce to below 45 mN/m. In contrast, the surface tension of pure water is 72 mN/m at room temperature. In some embodiments, such a reduction in the equilibrium surface tension at a water/air interface may be achieved using a hydrophobin concentration of between $5 \times 10^{-8}$M and $2 \times 10^{-6}$ M, e.g., between $1 \times 10^{-7}$M and $1 \times 10^{-6}$M. In some embodiments such a reduction in the equilibrium surface tension at a water/air interface may be achieved at a temperature ranging from 0° C. to 50° C., especially room temperature. The change in equilibrium surface tension can be measured using a tensiometer following the method described in Cox et al., *Langmuir*, 2007, 23, 7995-8002.

In some embodiments, the hydrophobin may cause the surface shear elasticity ($G'_s$) at a water/air interface to increase to 30-35 mN/m, 40-50 mN/m, or higher. In some embodiments, the hydrophobin may cause the surface shear elasticity ($G'_s$) at a water/air interface to increase to 0.3-0.6 N/m, or higher. In some embodiments, such a surface shear elasticity at a water/air interface may be achieved using a hydrophobin concentration of between 0.01-100 mM. In some embodiments, the hydrophobin is present in a concentration of 0.1 μM-50 mM. In some embodiments, the hydrophobin is present in a concentration of 0.1-20% by weight of the total weight of the composition. In some embodiments, such a surface shear elasticity at a water/air interface may be achieved using a hydrophobin concentration of between 0.01-50 mM. In some embodiments, such a surface shear elasticity at a water/air interface may be achieved using a hydrophobin concentration of between 0.01-20 mM. In some embodiments, such a surface shear elasticity at a biomimetic membrane may be achieved at a temperature ranging from 0° C. to 50° C., especially room temperature. The change in equilibrium surface tension can be measured using a rheometer following the method described in Cox et al., *Langmuir*, 2007, 23, 7995-8002

In some embodiments, the hydrophobin may cause the equilibrium surface tension at a biomimetic membrane (e.g. a biomimetic membrane containing one or more membrane proteins) to reduce to below 50 mN/m. In some embodiments, such a reduction in the equilibrium surface tension at a biomimetic membrane may be achieved using a hydrophobin concentration of between 0.01-100 mM, 0.01-50 mM or between 0.01-20 mM. In some embodiments, the hydrophobin is present in a concentration of 0.1 μM-50 mM. In some embodiments, the hydrophobin is present in a concentration of 0.1-20% by weight of the total weight of the composition. In some embodiments such a reduction in the equilibrium surface tension at a biomimetic membrane may be achieved at a temperature ranging from 0-90° C.

In some embodiments, the hydrophobin may cause the surface shear elasticity at a biomimetic membrane (e.g. a biomimetic membrane containing one or more membrane proteins) to increase to 30-35 mN/m or higher. In some embodiments, the hydrophobin may cause the surface shear elasticity at a biomimetic membrane (e.g. a biomimetic membrane containing one or more membrane proteins) to increase to 0.3-0.6 N/m, or higher. In some embodiments, such a surface shear elasticity at a biomimetic membrane may be achieved using a hydrophobin concentration of between 0.01-100 mM, 0.01-50 mM or 0.01-20 mM. In some embodiments, the hydrophobin is present in a concentration of 0.1 µM-50 mM. In some embodiments, the hydrophobin is present in a concentration of 0.1-20% by weight of the total weight of the composition. In some embodiments, such surface shear elasticity at a biomimetic membrane may be achieved at a temperature ranging from 0-90° C.

In some embodiments, the hydrophobins used in the present invention are characterized by their effect on stabilization and/or dispersion of membrane proteins. In some embodiments the hydrophobins are used to disperse membrane proteins. Thus, in some embodiments, the membrane protein molecules are held in dispersion in a medium. The invention provides stable dispersions of the membrane proteins. The dispersed membrane protein can then be used in the formation of biomimetic membranes.

In some embodiments, the hydrophobins used in the present invention are biosurfactants. Biosurfactants are surface-active substances synthesized by living cells. Among other properties, they have the properties of reducing surface tension, stabilizing emulsions, promoting foaming and are generally non-toxic and biodegradable.

Examples of specific hydrophobins useful in the methods, compositions, kits and/or apparatuses of the present disclosure are listed in Table 1 below.

TABLE 1

| Organism | Gene, Protein name | NCBI accession code and version number |
|---|---|---|
| Agaricus bisporus | ABH3 | Y14602.1 |
| Agaricus bisporus | HYPB | Y15940.1 |
| Aspergillus fumigatus | HYP1/RODA | L25258.1, U06121.1 |
| Aspergillus fumigatus | RODB | AY057385.1 |
| Aspergillus niger | A_NIG1 | XM_001394993.1 |
| Aspergillus oryzae | HYPB | AB097448.1 |
| Aspergillus oryzae | ROLA | AB094496.1 |
| Aspergillus terreus | A_TER | XM_001213908.1 |
| Cladosporium fulvum | HCF-5 | AJ133703.1 |
| Cladosporium fulvum | HCF-6 | AJ251294.1 |
| Cladosporium fulvum | HCF-3 | AJ566186.1 |
| Cladosporium fulvum | HCF-1 | X98578.1 |
| Cladosporium fulvum | HCF-2 | AJ133700.1 |
| Cladosporium fulvum | HCF-4 | AJ566187.1 |
| Cladosporium herbarum | HCH-1 | AJ496190.1 |
| Claviceps fusiformis | CFTH1_I-III | AJ133774.1 |
| Claviceps fusiformis | CLF | CAB61236.1 |
| Claviceps purpurea | CLP | CAD10781.1 |
| Claviceps purpurea | CPPH1_I-V | AJ418045.1 |
| Coprinus cinereus | COH1 | Y10627.1 |
| Coprinus cinereus | COH2 | Y10628.1 |
| Cryphonectria parasitica | CRP | L09559.1 |
| Dictyonema glabratum | DGH3 | AJ320546.1 |
| Dictyonema glabratum | DGH2 | AJ320545.1 |
| Dictyonema glabratum | DGH1 | AJ320544.1 |
| Emericella nidulans | RODA | M61113.1 |
| Emericella nidulans | DEWA | U07935.1 |
| Flammulina velutipes | FVH1 | AB026720.1 |
| Flammulina velutipes | FvHYD1 | AB126686.1 |
| Gibberella moniliformis | HYD5, GIM | AY158024.1 |
| Gibberella moniliformis | HYD4 | AY155499.1 |
| Gibberella moniliformis | HYD1 | AY155496.1 |
| Gibberella moniliformis | HYD2 | AY155497.1 |
| Gibberella moniliformis | HYD3 | AY155498.1 |
| Gibberella zeae | GIZ, FG01831.1 | XP_382007.1 |
| Lentinula edodes | Le.HYD1 | AF217807.1 |
| Lentinula edodes | Le.HYD2 | AF217808.1 |
| Magnaporthe grisea | MGG4 | XM_364289.1 |
| Magnaporthe grisea | MGG2 | XM_001522792.1 |
| Magnaporthe grisea | MHP1, MGG1 | AF126872.1 |
| Magnaporthe grisea | MPG1 | L20685.2 |
| Metarhizium anisopliae | SSGA | M85281.1 |
| Neurospora crassa | NCU08192.1 | AABX01000408.1 |
| Neurospora crassa | EAS | AAB24462.1 |
| Ophiostoma ulmi | CU | U00963.1 |
| Paracoccidioides brasilensis | PbHYD2 | AY427793.1 |
| Paracoccidioides brasilensis | PbHYD1 | AF526275.1 |
| Passalora fulva | PF3 | CAC27408.1 |
| Passalora fulva | PF1 | CAC27407.1 |
| Passalora fulva | PF2 | CAB39312.1 |
| Pholiota nameko | PNH2 | AB079129.1 |
| Pholiota nameko | PNH1 | AB079128.1 |
| Pisolithus tinctorius | HYDPt-1 | U29605.1 |
| Pisolithus tinctorius | HYDPt-2 | U29606.1 |
| Pisolithus tinctorius | HYDPt-3 | AF097516.1 |
| Pleurotus ostreatus | POH2 | Y14657.1 |
| Pleurotus ostreatus | POH3 | Y16881.1 |
| Pleurotus ostreatus | VMH3 | AJ238148.1 |
| Pleurotus ostreatus | POH1 | Y14656.1 |
| Pleurotus ostreatus | FBHI | AJ004883.1 |
| Schizophyllum commune | SC4 | M32330.1 |
| Schizophyllum commune | SC1, 1G2 | X00788.1 |
| Schizophyllum commune | SC6 | AJ007504.1 |
| Schizophyllum commune | SC3 | AAA96324.1 |
| Talaromyces thermophilus | TT1 | |
| Trichoderma harzianum | QID3 | X71913.1 |
| Trichoderma harzianum | SRH1 | Y11841.1 |
| Trichoderma reesei | HFBII | P79073.1 |
| Trichoderma reesei | HFBI | P52754.1 |
| Tricholoma terreum | HYD1 | AY048578.1 |
| Verticillium dahliae | VED | AAY89101.1 |
| Xanthoria ectaneoides | XEH1 | AJ250793.1 |
| Xanthoria parietina | XPH1 | AJ250794.1 | d. Fusion Proteins

The hydrophobin of the present disclosure includes fusion proteins of a hydrophobin and another polypeptide as well as conjugates of hydrophobin and other molecules such as polysaccharides.

In some embodiments, the hydrophobin is a hydrophobin fusion protein. The term "fusion protein" includes a hydrophobin sequence (as defined and exemplified above) bonded to a further peptide sequence (described herein as "a fusion partner") which does not occur naturally in a hydrophobin.

In some embodiments, the fusion partner may be bonded to the amino terminus of the hydrophobin core, thereby forming the group $(Y_1)_m$. In some embodiments, m may range from 1 to 2000, or 2 to 1000, or 5 to 500, or 10 to 200, or 20 to 100.

In some embodiments, the fusion partner may be bonded to the carboxyl terminus of the hydrophobin core, thereby forming the group $(Y_2)_n$. In some embodiments, n may range from 1 to 2000, or 2 to 1000, or 5 to 500, or 10 to 200, or 20 to 100.

In some embodiments, fusion partners may be bonded to both the amino and carboxyl termini of the hydrophobin core. In some embodiments, the fusion partners may be the same or different, and may have amino acid sequences having the number of amino acids defined above by the stated values of m and n.

In some embodiments, the hydrophobin is not a fusion protein and m and n are 0.

Membrane Proteins

In some embodiments, the biomimetic membranes describe herein comprise one or more membrane proteins. In some embodiments, the biomimetic membranes further comprise one or more hydrophobin. The membrane protein to be incorporated into a membrane according to the invention can be any membrane protein.

In some embodiments the hydrophobins described herein are used to stabilize membrane proteins. The term stabilize includes disperse and/or emulsify. Thus, in some embodiments, the membrane protein molecules are held in dispersion in a medium. The invention provides stable dispersions of the membrane proteins. The dispersed membrane protein can then be used in the formation of biomimetic membranes.

Examples are G-protein coupled receptors such as odorant receptors, rhodopsin receptors, in particular bovine rhodopsin receptors, rhodopsin pheromone receptors, peptide hormone receptors, taste receptors, GABA receptors, opiate receptors, serotonin receptors, $Ca^{2+}$ receptor, melanopsin, neurotransmitter receptors, ligand gated, voltage gated or mechanically gated such as acetylcholine (ACh), nicotinic, adrener, norepinephrine, catecholamines, L-dopa, dopamine and serotonin—biogenic amines, endorphins/enkephalins—neuropeptide receptors, kinases such as serin/threonin kinases, cytoplasmic tyrosine kinases, receptor tyrosine kinases, phosphatases proteases, inactive kinases, porins/channels such as chloride channels, potassium channels, sodium channels, OMP proteins, ABC transporter (ATP-Binding Cassette-Transporter) such as amino acid transporter, Na-glucose transporter, $Na^+$/iodide transporter, ion transporters such as Light Harvesting Complex, cytochrome c oxidase, ATP ase Na/K, H/K,Ca, cell adhesion receptors such as metallo proteases, integrins, catherins.

In some embodiments, the biomimetic membranes comprise one or more membrane proteins, such as channel forming molecules, e.g. certain peptides or peptide like molecules including amphotericin B, alamethicin, valinomycin, gramicidin A and their dimers, oligomers and analogues thereof; or transmembrane proteins, e.g. aquaporin water channels, Fas protein, DsbB, CFTR, alpha-haemolysin, VDAC, and OmpG.

In some embodiments, the biomimetic membranes comprise one or more transmembrane proteins, e.g. aquaporin water channels. In some embodiments, the biomimetic membranes comprise one or more aquaporin water channels.

a. Aquaporin

Living cells are enclosed by a lipid bilayer membrane, separating the cells from other cells and their extracellular medium. Lipid bilayer membranes are essentially impermeable to water, ions, and other polar molecules; yet, in many instances, such entities need to be rapidly and selectively transported across a membrane, often in response to an extra- or intracellular signal. The water-transporting task is accomplished by aquaporin water channel proteins (Preston, G. M., P. Piazza-Carroll, W. B. Guggino, and P. Agre. (1992). Appearance of water channels in *Xenopus* oocytes expressing red cell CHIP28 water channel. Science, 256, 385-387). Aquaporins are crucial for life in any form and they are found in all organisms, from bacteria via plants to man Aquaporins facilitate rapid, highly selective water transport, thus allowing the cell to regulate its volume and internal osmotic pressure according to hydrostatic and/or osmotic pressure differences across the cell membrane. The physiological importance of the aquaporin in humans is perhaps most conspicuous in the kidney, where about 150-200 liters of water need to be reabsorbed from the primary urine each day, that is, aquaporin facilitated water transport is invoked when water rapidly must be retrieved from a body fluid. In kidneys, this is made possible mainly by two aquaporins denoted AQP1 and AQP2 (11 different aquaporins are known in humans) In plants, aquaporins are also critical for water absorption in the root and for maintaining the water balance throughout the plant (Agre, P., M. Bonhivers, and M. J. Borgnia. (1998) The aquaporins, blueprints for cellular plumbing systems. Journal of Biological Chemistry, 273, 14659-14662; Borgnia, M., S, Nielsen, A. Engel, and P. Agre. (1999). Cellular and molecular biology of the aquaporin water channels. Annual Review of Biochemistry, 68, 425-458). In plants, water is absorbed by the same osmotic forces as this invention intends to use in a PRO system in the production of salinity power.

Studies of water transport in various organisms and tissues suggested that aquaporins have a narrow pore preventing any flow of large molecules, ions (salts) and even protons ($H_3O+$) and hydroxyl ions (OH—) while maintaining an extremely high water permeation rate; about $10^9$ molecules $H_2O$ per channel per second (Agre, P., M. Bonhivers, and M. J. Borgnia. (1998) the aquaporins, blueprints for cellular plumbing systems. Journal of Biological Chemistry, 273, 14659-14662, Borgnia, M., S, Nielsen, A. Engel, and P. Agre. (1999). Cellular and molecular biology of the aquaporin water channels. Annual Review of Biochemistry, 68, 425-458). Until 2000 and 2001, where the first high-resolution 3D structure of AQP1 and that of the related glycerol-conducting bacterial channel protein aquaglyceroporin GlpF were reported (Fu, D., Libson, A., Miercke, L. J., Weitzman, C., Nollert, P., Krucinski, J., and Stroud, R. M. (2000). Structure of a glycerol-conducting channel and the basis for its selectivity, Science 290, 481-6; Murata, K., Mitsuoka, K., Hirai, T., Walz, T., Agre, P., Heymann, J. B., Engel, A., and Fujiyoshi, Y. (2000). Structural determinants of water permeation through aquaporin-1, Nature 407, 599-605), little was known about the origin of water selectivity.

However, based on the experimental structures, detailed computer models were put forward explaining not only the high permeation rate and the strict water selectivity but also the ability of aquaporins to prevent proton leakage (de Groot, B. L., and Grubmuller, H. (2001). Water permeation across biological membranes: mechanism and dynamics of aquaporin-1 and GlpF, Science 294, 2353-2357; de Groot, B. L., Frigato, T., Helms, V. and Grubmuller, H. (2003). The mechanism of proton exclusion in the aquaporin-1 channel, Journal of Molecular Biology 333, 279-293; Tajkhorshid, E., Nollert, P., Jensen, M. O., Miercke, L. J., O'Connell, J., Stroud, R. M., and Schulten, K. (2002). Control of the selectivity of the aquaporin water channel family by global orientational tuning, Science 296, 525-530; Jensen, M. O., Tajkhorshid, E., and Schulten, K. (2003). Electrostatic tuning of permeation and selectivity in aquaporin water channels, Biophysical Journal 85, 2884-2899; Zhu, F., Tajkhorshid, E. and Schulten, K. (2003). Theory and simulation of water permeation in aquaporin-1. Biophysical Journal, 86, 50-57; Burykin and A. Warshel (2003). What really prevents proton transport through aquaporin? Charge self-energy vs. proton wire proposals, Biophysical Journal 85, 3696-3706; Ilan, B., Tajkhorshid, E., Schulten, K. and Voth, G. (2004). The mechanism of proton exclusion in aquaporin water channels. PRO ILINS: Structure, Function, and Bioinformatics, 55, 223-228; Chakrabarti, N., Tajkhorshid, E., Roux, B. and Pommes, R. (2004). Molecular basis of proton blockage in aquaporins, Structure 12, 65-74). In essence, the architecture of the aquaporin channel allows water molecules to pass only in a single file while electrostatic tuning of the channel interior controls aquaporin selectivity against any charged species, that is, trans-port of any salt (ion) as well as protons and hydroxyl ions is abrogated (the high permeation rate and the strict water selectivity but also the ability of aquaporins to prevent proton leakage (de Groot, B. L., and Grubmuller, H. (2001). Water permeation across biological membranes: mechanism and dynamics of aquaporin-1 and GlpF, Science 294, 2353-2357; de Groot, B. L., Frigato, T., Helms, V. and Grubmuller, H. (2003). The mechanism of proton exclusion in the aquaporin-1 channel, Journal of Molecular Biology 333, 279-293; Tajkhorshid, E., Nollert, P., Jensen, M. O., Miercke, L. J., O'Connell, J., Stroud, R. M., and Schulten, K. (2002). Control of the selectivity of the aquaporin water channel family by global orientational tuning, Science 296, 525-530; Jensen, M. O., Tajkhorshid, E., and Schulten, K. (2003). Electrostatic tuning of permeation and selectivity in aquaporin water channels, Biophysical Journal 85, 2884-2899; Zhu, F., Tajkhorshid, E. and Schulten, K. (2003). Theory and simulation of water permeation in aquaporin-1. Biophysical Journal, 86, 50-57; Burykin and A. Warshel (2003). What really prevents proton transport through aquaporin? Charge self-energy vs. proton wire proposals, Biophysical Journal 85, 3696-3706; Ilan, B., Tajkhorshid, E., Schulten, K. and Voth, G. (2004). The mechanism of proton exclusion in aquaporin water channels. PRO ILINS: Structure, Function, and Bioinformatics, 55, 223-228; Chakrabarti, N., Tajkhorshid, E., Roux, B. and Pommes, R. (2004). Molecular basis of proton blockage in aquaporins, Structure 12, 65-74). In short, this shows the high selectivity of the aquaporin water pore.

Each unit in an aquaporin channel transports about $10^9$ $H_2O$ molecules/sec, i.e., about $410^9$ molecules/channel/sec. Hence, 1 g of aquaporin is capable of transporting about 720 liter of water/sec at very high pressure.

The term "aquaporin family of membrane proteins" as used herein includes also the GLpF proteins which in addition to water molecules also channels glycerol.

Transmembrane proteins different from aquaporins suitable for inclusion in the membranes of the present invention are for instance selected from, but not limited to, any transmembrane protein found in the Transporter Classification Database (TCDB). TCDB is accessible at the TCDB website.

Examples of transmembrane proteins included in the present invention from TCDB are: Aerolysin channel-forming toxin, Agrobacterial target-host cell-membrane anion channel, a-Hemolysin channel-forming toxin, Alamethicin channel, Alginate export porin, Amoebapore, Amphipathic peptide mastoparan, Amyloid b-protein peptide, Animal inward-rectifier $K^+$ channel, Annexin, Apoptosis regulator, ArpQ holin, AS-48, ATP-gated cation channel, Autotransporter, *Bacillus subtilis* j29 holin, Bacterial type III-target cell pore, Bactericidal permeability-increasing protein, Bacteriocin AS-48 cyclic polypeptide, Bacteriorhodopsin, Beticolin channel, BlyA holing, Botulinum and tetanus toxin, *Brucella-Rhizobium porin*, *Campylobacter jejuni* major outer membrane porin, Cathilicidin, cation channel, Cation-channel-forming heat-shock protein 70, Cecropin, Channel-forming *Bacillus* anthrax protective antigen, Channel-forming ceramide, Channel-forming colicin, Channel-forming colicin V, Channel-forming d-endotoxin insecticidal crystal protein, Channel-forming e-toxin, Channel-forming leukocidin cytotoxin, Chlamydial porin, Chloride channel, Chloroplast membrane anion-channel-former, Chloroplast outer-membrane solute channel, Cholesterol-binding thiol-activated cytolysin, Clostridial cytotoxin, Complement protein C9, Complexed polyhydroxybutyrate-$Ca^{2+}$ channel, Corynebacterial porin, Cphl holin, C-type natriuretic peptide, Cyanobacterial porin, Cyclodextrin porin, Cytohemolysin, Cytotoxic amylin, Defensin, Dermaseptin, Diphtheria toxin, Divergicin A, Earthworm lysenin toxin, Envelope virus E1 channel, Epithelial chloride channel, Epithelial $Na^+$ channel, FadL outer-membrane protein, Fusobacterial outer-membrane porin, Gap-junction-forming connexin, Gap-junction-forming innexin, General bacterial porin, Glucose-selective OprB porin, Glutamate-gated ion channel of neurotransmitter receptors, gp91$^{Phox}$ phagocyte NADPH-oxidase-associated cyt $b_{558}$ $H^+$-channel, Gramicidin A channel, $H^+$- or $Na^+$-translocating bacterial flagellar motor, $H^+$- or $Na^+$-translocating bacterial MotAB flagellar motor/ExbBD outer-membrane transport, *Helicobacter* outer membrane porin, HP1 holin, Influenza virus matrix-2 channel, Insect defensin, Intracellular chloride channel, j11 holin, jAdh holing, jU53 holin, Lactacin X, Lacticin 481, Lactocin S, Lactococcin 972, Lactococcin A, Lactococcin G, Large-conductance mechanosensitive ion channel, lholin S, Ligand-gated ion channel of neurotransmitter receptors, LrgA holin, LydA holin, Magainin, Major intrinsic protein, Melittin, Metal-ion transporter (channel), Microcin E492, Mitochondrial and plastid porin, Mycobacterial porin, Nisin, Nonselective cation channel-1, Nonselective cation channel-2, Nucleoside-specific channel-forming outer-membrane porin, OmpA-OmpF porin, OmpG porin, Organellar chloride channel, Outer-bacterial-membrane secretin, Outer-membrane auxiliary protein, Outer-membrane factor, Outer-membrane fimbrial usher porin, Outer-membrane porin, Outer-membrane receptor, P2 holin TM, P21 holin S, Pediocin, Phospholemman, Pilosulin, Plant defensin, Plant plasmodesmata, Plant thionine, Plantaricin E F, Plantaricin J K, Plastid outer-envelope porin of 16 kDa, Plastid outer-envelope porin of 21 kDa, Plastid outer-envelope porin of 24 kDa, Polycystin cation channel, Polyglutamine ion channel, Pore-forming equinatoxin, Pore-forming hemolysin E, Pore-forming RTX toxin, PRD1 holin M, Prion peptide fragment, *Pseudomonas syringae* HrpZ target-host cell-membrane, *Pseudomonas* OprP porin, Raffinose porin, *Rhodobacter* PorCa porin, Ryanodine-inositol-1,4,5-trisphosphate receptor $Ca^+$ channel, Saponin channel, Shiga toxin B-chain, Short-chain amide and urea porin, Small-conductance mechanosensitive ion channel, Sugar porin, Syringomycin channel, Syringopeptin channel, T4 holin, T4 Immunity holing, T7 holin, Tachyplesin, Tolaasin channel, TonB-ExbB-ExbD/TolA-TolQ-TolR of energizers for outer-membrane receptor (OMR)-medi-Transient receptor potential $Ca^+$ channel, Tripartite hemolysin BL, Two-partner secretion porin, Type B influenza virus NB channel, Urea transporter (channel), Urea/amide channel, Vacuolating cytotoxin, *Vibrio* chitoporin/*Neisseria* porin, Voltage-gated ion channel superfamily, Whipworm stichosome porin, Yeast killer toxin K1, Yeast stretch-activated cation-selective, $Ca^+$ channel.

In some embodiments, the aquaporin water channel is selected from the group consisting of aquaglyceroporins (GLpF), such as a GLPA channel, a GLPB1 channel, a GLPB2 channel, a GLPB3 channel, and a GLPY2 channel, and mixtures and hybrids thereof. In some embodiments, the aquaporin water channel is aquaporin Z (AqpZ), which is derived from *E. Coli*. In some embodiments, the aquaporin channels are modified. In some embodiments, AqpZ can be modified to fulfill a desired application that may be different from the protein's original function. For example, by simply changing a particular amino acid residue near the center of the water channel to cysteine, the Aquaporins produced would bind any free Mercury in the solution and cease transporting water due to the blockage. Thus, these mutant proteins used in a membrane device could detect Mercury contamination in a water sample by simply ceasing flow when the concentration of the toxic substance rises too high.

In some embodiments, one or more hydrophobins described herein are used to disperse aquaporin proteins. Thus, in some embodiments, the aquaporin protein molecules are held in dispersion in a medium. The invention provides stable dispersions of the aquaporin proteins. The dispersed aquaporin protein can then be used in the formation of biomimetic membranes. In some embodiments, the biomimetic membranes further comprise or more hydrophobins in combination with one or more aquaporins. In some embodiments, the hydrophobin is selected from the group consisting of: (a) HFBII (SEQ ID NO: 2; obtainable from the fungus *Trichoderma reesei*); (b) HFBI (SEQ ID NO: 4; obtainable from the fungus *Trichoderma reesei*); (c) SC3 (SEQ ID NO: 6; obtainable from the fungus *Schizophyllum commune*); (d) EAS (SEQ ID NO: 8; obtainable from the fungus *Neurospora crassa*); and (e) TT1 (SEQ ID NO: 10; obtainable from the fungus *Talaromyces thermophilus*); or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any thereof.

In some embodiments, the hydrophobin is "HFBII" (SEQ ID NO: 2; obtainable from *Trichoderma reesei*) or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core thereof.

In some embodiments, the dispersed medium comprise HFBII and one or more aquaporin water channels selected from the group consisting of aquaglyceroporins (GLpF), such as a GLPA channel, a GLPB1 channel, a GLPB2 channel, a GLPB3 channel, and a GLPY2 channel, and mixtures and hybrids thereof. In some embodiments, the dispersed medium comprises HFBII and AqpZ. In some embodiments, the aquaporin channels are modified.

In some embodiments, the biomimetic membranes comprise HFBII and one or more aquaporin water channels selected from the group consisting of aquaglyceroporins (GLpF), such as a GLPA channel, a GLPB1 channel, a GLPB2 channel, a GLPB3 channel, and a GLPY2 channel, and mixtures and hybrids thereof. In some embodiments, the biomimetic membrane comprises HFBII and AqpZ. In some embodiments, the aquaporin channels are modified.

Biomimetic Membranes

In one aspect, the present invention provides biomimetic membranes. The term biomimetic membrane includes one or more membranes or walls or shells. The biomimetic membranes include vesicles (e.g. liposomes, micelles, polymerosome, nanoparticles and microbubbles) surrounding an internal void that could be empty or filled, e.g. filled with a gas, liquid or precursor thereto. The biomimetic membranes include planar biomimetic membranes as well as solid-supported membranes such as solid-supported lipid bilayers and tethered lipid bilayers, or membranes comprising vesicles. In some embodiments, the biomimetic membranes comprise one or more lipids and/or one or more polymers. The term lipids includes agents exhibiting amphipathic characteristics causing it to spontaneously adopt an organized structure in water wherein the hydrophobic portion of the molecule is sequestered away from the aqueous phase. In some embodiments, the biomimetic membranes comprise polymerizable lipids. In some embodiments, the biomimetic membranes comprise one or more lipids, at least one of which is polymerizable. In some embodiments, the biomimetic membranes also contain one or more polypeptides, and/or other functional molecules.

The biomimetic membranes of the invention may also include any other materials or combination thereof known to those skilled in the art as suitable for biomimetic membrane construction.

a. Lipids

In one aspect, the biomimetic membranes of the invention comprise one or more lipid. Examples of useful lipids for the formation of lipid membranes (e.g. monolayer, bilayers, planar or vesicles) to be used in the biomimetic membranes of the invention, include but are not limited to:

(i) Phosphatidylcholines: 1,2-dimyristoylphosphatidylcholine (DMPC); 1,2-dipalmitoylphosphatidylcholine (DPPC); 1,2-distearoylphosphatidylcholine (DSPC); 1,2-dioleoylphosphatidylcholine (DOPC); 1,2-dimyristoleoylphosphatidylcholine; 1,2-dipalmitoleoylphosphatidylcholine; 1,2-dipetroselinoylphosphatidylcholine; 1,2-dielaidoylphosphatidylcholine; 1,2-dilinoleoylphosphatidylcholine; 1,2-dilinolenoylphosphatidylcholine; 1,2-dieicosenoylphosphatidylcholine; 1,2-diarachidonoylphosphatidylcholine; 1,2-dierucoylphosphatidylcholine; 1,2-dnervonoylphosphatidylcholine; 1-palmitoyl-2-oleoylphosphatidylcholine (POPC); 1-palmitoyl-2-linoleoylphosphatidylcholine; 1-palmitoyl-2-arachidonoylphosphatidylcholine; 1-palmitoyl-2-docosahexaenoylphosphatidylcholine; 1-stearoyl-2-oleoylphosphatidylcholine (SOPC); 1-stearoyl-2-linoleoylphosphatidylcholine; 1-stearoyl-2-arachidonoylphosphatidylcholine; 1-stearoyl-2-docosahexaenoylphosphatidylcholine; 1-oleoyl-2-palmitoylphosphatidylcholine; 1-oleoyl-2-stearoylphosphatidylcholine; 1,2-didocosahexaenoylphosphatidylcholine;

(ii) Phosphatidylethanolamines: 1,2-dimyristoylphosphatidylethanolamine (DMPE); 1,2-dipalmitoylphosphatidylethanolamine (DPPE); 1,2-distearoylphosphatidylethanolamine (DSPE); 1,2-dioleoylphosphatidylethanolamine (DOPE); 1-palmitoyl-2-oleoylphosphatidylethanolamine (POPE); 1-palmitoyl-2-linoleoylphosphatidylethanolamine; 1-palmitoyl-2-arachidonoylphosphatidylethanolamine; 1-palmitoyl-2-docosahexaenoylphosphatidylethanolamine; 1-stearoyl-2-oleoylphosphatidylethanolamine (SOPE); 1-stearoyl-2-linoleoylphosphatidylethanolamine; 1-stearoyl-2-arachidonoylphosphatidylethanolamine; 1-stearoyl-2-docosahexaenoylphosphatidylethanolamine; 1,2-dielaidoylphosphatidylethanolamine; 1,2-dilinoleoylphosphatidylethanolamine; 1,2-dilinolenoylphosphatidylethanolamine; 1,2-diarachidonoylphosphatidylethanolamine; 1,2-didocosahexaenoylphosphatidylethanolamine; 1,2-dipalmitoleoylphosphatidylethanolamine;

(iii) Phosphatidylglycerols: 1,2-dimyristoylphosphatidylglycerol (DMPG); 1,2-dipalmitoylphosphatidylglycerol (DPPG); 1,2-distearoylphosphatidylglycerol (DSPG); 1,2-dioleoylphosphatidylglycerol (DOPG); 1-palmitoyl-2-oleoylphosphatidylglycerol (POPG); 1-palmitoyl-2-linoleoylphosphatidylglycerol; 1-palmitoyl-2-arachidonoylphosphatidylglycerol; 1-palmitoyl-2-docosahexaenoylphosphatidylglycerol; 1-stearoyl-2-oleoylphosphatidylglycerol (SOPG); 1-stearoyl-2-linoleoylphosphatidylglycerol; 1-stearoyl-2-arachidonoylphosphatidylglycerol; 1-stearoyl-2-docosahexaenoylphosphatidylglycerol;

(iv) Phosphatidylserines: 1-palmitoyl-2-oleoylphosphatidylserine (POPS); 1-palmitoyl-2-linoleoylphosphatidylserine; 1-palmitoyl-2-arachidonoylphosphatidylserine; 1-palmitoyl-2-docosahexaenoylphosphatidylserine; 1-stearoyl-2-oleoylphosphatidylserine (SOPS); 1-stearoyl-2-linoleoylphosphatidylserine; 1-stearoyl-2-arachidonoylphosphatidylserine; 1-stearoyl-2-docosahexaenoylphosphatidylserine; 1,2-dimyristoylphosphatidylserine (DMPS); 1,2-dipalmitoylphosphatidylserine (DPPS); 1,2-distearoylphosphatidylserine (DSPS); 1,2-dioleoylphosphatidylserine (DOPS); 1,2-didocosahexaenoylphosphatidylserine; 1,2-dierucoylphosphatidylserine;
(v) Special lipids: Cardiolipin; Bipolar lipids;
(vi) Polymerizable lipids: 1,2-di-10,12-tricosadiynoyl-sn-glycero-3-phosphocholine (DTPC); 1,2-di-10,12-tricosadiynoyl-sn-glycero-3-phosphoethanolamine (DTPE); 1-palmitoyl-2,10,12-tricosadiynoyl-sn-glycero-3-phosphoethanolamine (PTPE); (DC8,9PC [1,2-bis(10,12-tricosadiynoyl)-sn-glycero-3-phosphocholine]; diPhyPC [1,2-diphytanoyl-sn-glycero-3-phosphocholine]
(vii) Natural lipid extracts: Egg yolk phosphatidylcholine; Bovine heart phosphatidylcholine; Brain phosphatidylcholine; Bovine liver phosphatidylcholine; Soybean phosphatidylcholine; *E. Coli* phosphatidylethanolamine; Bovine Heart phosphatidylethanolamine; Brain phosphatidylethanolamine; Bovine Liver phosphatidylethanolamine; Egg phosphatidylethanolamine; Bovine liver phosphatidylinositol; Soybean phosphatidylinositol; Brain phosphatidylserine; Soy phosphatidylserine.

Useful lipids for reconstitution of aquaporins and/or hydrophobins and formation of lipid bilayers are: POPC, DPPC, ceramide and mixtures thereof.

In some embodiments, the biomimetic membranes of the invention comprise one or more polymerizable lipid. Examples of polymerizable lipids include but are not limited to, diyne PC and diynePE, for example 1,2-bis(10,12-tricosadiynoyl-sn-glycero-3-phosphocoline. In some embodiments, the biomimetic membrane of the invention comprise at least 0.1%, 0.5%, 1%, 5%, 10%, 15%, 20%, 25%, 30%, 35%, 40%, 45%, 50%, 55%, 60%, 70%, 80%, 90% or 100% of polymerizable lipids. In some embodiments, the biomimetic membranes of the invention comprise at least 25% of polymerizable lipids. In some embodiments, the biomimetic membranes of the invention comprise at least 50% of polymerizable lipids. In some embodiments, the polymerizable lipid may comprise a polymerizable group attached to a lipid molecule. The biomimetic membranes may also contain lipids that are not polymerizable, lipids conjugated to a functional moiety (such as a targeting agent), and lipids with a positive, negative, or neutral charge.

In some embodiments, the biomimetic membranes of the invention comprise one or more neutral phospholipids. Examples of neutral phospholipids include, but are not limited to, hydrogenated phosphatidyl choline (HSPC), dipalmitoyl-, distearoyl- and diarachidoyl phosphatidylcholine (DPPC, DSPC, DAPC). In some embodiments, the biomimetic membranes of the invention comprise at least 0.1%, 0.5%, 1%, 5%, 10%, 15%, 20%, 25%, 30%, 35%, 40%, 45%, 50%, 55%, 60%, 70%, 80%, 90% or 100% of neutral phospholipids. In some embodiments, the biomimetic membranes of the invention comprise at least 10% of neutral phospholipids. In some embodiments, the biomimetic membranes of the invention comprise at least 30% of neutral phospholipids. In some embodiments, the biomimetic membranes of the invention comprise at least 45% of neutral phospholipids.

In some embodiments, the biomimetic membranes of the invention comprise one or more negatively charged phospholipids. Examples of negatively charged phospholipids include, but are not limited to, dipalmitoyl and distearoyl phosphatidic acid (DPPA, DSPA), dipalmitoyl and distearoyl phosphatidyls erine (DPPS, DSPS), phosphatidyl glycerols such as dipalmitoyl and distearoyl phosphatidylglycerol (DPPG, DSPG). In some embodiments, the biomimetic membranes of the invention comprise at least 0.1%, 0.5%, 1%, 5%, 10%, 15%, 20%, 25%, 30%, 35%, 40%, 45%, 50%, 55%, 60%, 70%, 80%, 90% or 100% of negatively charged phospholipids. In some embodiments, the biomimetic membranes of the invention comprise at least 2% of negatively charged phospholipids. In some embodiments, the biomimetic membranes of the invention comprise at least 5% of negatively charged phospholipids. In some embodiments, the biomimetic membranes of the invention comprise at least 10% of negatively charged phospholipids. In some embodiments, the biomimetic membranes of the invention comprise at least 25% of negatively charged phospholipids. In some embodiments, the biomimetic membranes of the invention comprise at least 30% of negatively charged phospholipids.

In some embodiments, the biomimetic membranes of the invention comprise one or more reactive phospholipids. Examples of reactive phospholipids include, but are not limited to, phosphatidyl ethanolamine derivatives coupled to a polyethyleneglycol, a biotinyl, a glutaryl, a caproyl, a maleimide, a sulfhydral, a pyridinal disulfide or a succinyl amine. In some embodiments, the biomimetic membranes of the invention comprise at least 0.1%, 0.5%, 1%, 5%, 10%, 15%, 20%, 25%, 30%, 35%, 40%, 45%, 50%, 55%, 60%, 70%, 80%, 90% or 100% of reactive phospholipids. In some embodiments, the biomimetic membranes of the invention comprise at least 2% of reactive phospholipids. In some embodiments, the biomimetic membranes of the invention comprise at least 5% of reactive phospholipids. In some embodiments, the biomimetic membranes of the invention comprise at least 10% of reactive phospholipids. In some embodiments, the biomimetic membranes of the invention comprise at least 25% of reactive phospholipids. In some embodiments, the biomimetic membranes of the invention comprise at least 30% of reactive phospholipids.

In some embodiments, the biomimetic membranes of the invention comprise one or more lipids and phospholipids such as soy lecithin, partially refined lecithin, hydrogenated phospholipids, lysophosphate, phosphatidylcholine, phosphatidylethanolamine, phosphatidylserine, phosphatidylinositol, cardiolipin, sphingolipids, gangliosides, cerebrosides, ceramides, other esters analogue of phopshpatidylcholine (PAF, lysoPAF). In some embodiments, the biomimetic membranes of the invention comprise one or more synthetic phospholipids such as L-a-lecithin (dilauroylphosphatidylcholine, dipalmitoylphosphatidylcholine, dilinoloylphosphatidylcholine, distearoylphosphatidylcholine, diarachidoylphosphatidylcholine); phosphatidylethanolamine derivatives, such as 1,2-diacyl-sn-glycero-3-phosphoethanolamine, 1-acyl-2-acyl-sn-glycero-3-phosphoethanolamine, dinitrophenyl- and dinitrophenylamino caproylphosphatidylethanolamine, 1,2-diacyl-sn-glycero-3-phosphoethanolamine-N-poly ethylene glycol (PEG-PE), N-biotinyl-PE, N-caproylamine PE, N-dodecylamine-PE, N-MPB-PE, N-PDD-PE, N-succinyl-PE, N-glutaryl-PE; di-acetylenic lipids; phosphatidic acids (1,2-diacyl-sn-glycero-3-phosphate salt, 1-acyl-2-acyl-sn-glycero-3-phosphate sodium salt; phosphatidylserine such as 1,2-diacyl-snglycero-3-[phospho-L-serine] sodium salt, 1-acyl-2-acyl-sn-glycero-3-[phospho-L-serine] sodium salt, lysophosphatidic acid; cationic lipids such as 1,2-diacyl-3-trimethylammoniumpropane (TAP), 1,2-diacyl-3-dimethylammoniumpropane (DAP), N-[1-(2,3-dioleoyloxy) propyl-N,N',N''-trimethylammonium chloride (DOTMA).

In some embodiments, the biomimetic membranes of the invention comprise one or more lipids suitable for click chemistry, such as those containing azide and alkyne groups. In some embodiments, the biomimetic membranes of the invention comprise one or more phospholipids with multi-various headgroups such as phosphatidylethanol, phosphatidylpropanol and phosphatidylbutanol, phosphatidylethanolamine-N-monomethyl, 1,2-disteraoyl(dibromo)-sn-glycero-3-phosphocoline. In some embodiments, the biomimetic membranes of the invention comprise one or more phospholipids with partially or fully fluorinated cholesterol or cholesterol derivatives can be used in place of an uncharged lipid, as generally known to a person skilled in the art.

The surface of a biomimetic membrane may also be modified with a polymer, such as, for example, with polyethylene glycol (PEG), using procedures readily apparent to those skilled in the art. Lipids may contain functional surface groups for attachment to a metal, which provides for the chelation of radioactive isotopes or other materials that serve as the therapeutic entity. Any species of lipid may be used, with the sole proviso that the lipid or combination of lipids and associated materials incorporated within the lipid matrix should form a monolayer phase under physiologically relevant conditions. As one skilled in the art will recognize, the composition of the biomimetic membrane may be altered to modulate the biodistribution and clearance properties of the resulting biomimetic membranes.

Other useful lipids or combinations thereof apparent to those skilled in the art which are in keeping with the spirit of the present invention are also encompassed by the present invention. For example, carbohydrates bearing lipids may be employed for in vivo targeting as described in U.S. Pat. No. 4,310,505.

In some embodiments, the biomimetic membranes of the invention comprise one or more polymerizable lipid. Polymerizable lipids that can be used in the present invention include those described in U.S. Pat. Nos. 5,512,294 and 6,132,764, and US publication No. 2010/0111840, incorporated by reference herein in their entirety.

In some embodiments, the hydrophobic tail groups of polymerizable lipids are derivatized with polymerizable groups, such as diacetylene groups, which irreversibly cross-link, or polymerize, when exposed to ultraviolet light or other radical, anionic or cationic, initiating species, while maintaining the distribution of functional groups at the surface of the biomimetic membrane. The resulting polymerized biomimetic membrane is stabilized against fusion with cell membranes or other biomimetic membranes and stabilized towards enzymatic degradation. The size of the polymerized biomimetic membranes can be controlled by the method described herein, but also by other methods known to those skilled in the art, for example, by extrusion.

Polymerized biomimetic membranes may be comprised of polymerizable lipids, but may also comprise saturated and non-alkyne, unsaturated lipids. The polymerized biomimetic membranes can be a mixture of lipids which provide different functional groups on the hydrophilic exposed surface. For example, some hydrophilic head groups can have functional surface groups, for example, biotin, amines, cyano, carboxylic acids, isothiocyanates, thiols, disulfides, α-halocarbonyl compounds, α,β-unsaturated carbonyl compounds and alkyl hydrazines. These groups can be used for attachment of targeting agents, such as antibodies, ligands, proteins, peptides, carbohydrates, vitamins, nucleic acids or combinations thereof for specific targeting and attachment to desired cell surface molecules, and for attachment to other surfaces. Other hydrophilic head groups can have a functional surface group of diethylenetriamine pentaacetic acid, ethylenedinitrile tetraacetic acid, tetraazocyclododecane-1, 4,7,10-tetraacetic acid (DOTA), porphoryin chelate and cyclohexane-1,2,-diamino-N,N'-diacetate, as well as derivatives of these compounds, for attachment to a metal, which provides for the chelation of radioactive isotopes or other materials. Examples of lipids with chelating head groups are provided in U.S. Pat. No. 5,512,294, incorporated by reference herein in its entirety.

The component lipids of the biomimetic membranes can be purified and characterized individually using standard, known techniques and then combined in controlled fashion to produce the final particle. The biomimetic membranes can be constructed to mimic native cell membranes or present functionality, such as ethylene glycol derivatives. Additionally, the biomimetic membranes can have a well-defined monolayer or bilayer structure that can be characterized by known physical techniques such as transmission electron microscopy and atomic force microscopy.

b. Polymers

In one aspect, the biomimetic membranes of the invention comprise one or more polymers. In some embodiments, the biomimetic membranes comprise block copolymer membranes simulating a natural environment. In some embodiments, the polypeptide(s) described herein (e.g. aquaporin and/or hydrophobin) are incorporated into the block copolymer membranes simulating a natural environment.

Various types of amphiphilic copolymers can be used. In one embodiment, the copolymer is an ABA copolymer, where A is hydrophilic and B is hydrophobic where A is the same or different hydrophilic segments and B is a hydrophobic B segment. Thus, the term "ABA copolymer" includes an ABC copolymer, where the hydrophilic segments A and C are different.

One class of suitable polymeric materials is described in U.S. Pat. No. 5,807,944 to Hirt, et al. In one embodiment, the amphiphilic polymer is biocompatible. Many suitable amphiphilic copolymers and hydrophobic and hydrophilic copolymers are described in WO 97/49387.

The block copolymer includes at least one segment B that includes a hydrophobic polymer. Any of a number of hydrophobic polymers can be used, such as, but not limited to, polysiloxane such as polydimethylsiloxane and polydiphenylsiloxane, perfluoropolyether, polystyrene, polyoxypropylene, polyvinylacetate, polyoxybutylene, polyisoprene, polybutadiene, polyvinylchloride, polyalkylacrylate (PAA), polyalkylmethacrylate, polyacrylonitrile, polypropylene, PTHF, polymethacrylates, polyacrylates, polysulfones, polyvinylethers, and poly(propylene oxide), and copolymers thereof.

In some embodiments, the hydrophobic segment contains a predominant amount of hydrophobic monomers. A hydrophobic monomer is a monomer that typically gives a homopolymer that is insoluble in water and can absorb less than 10% by weight of water.

Suitable hydrophobic monomers are C1-C18 alkyl and C3-C18 cycloalkyl acrylates and methacrylates, C3-C18 alkylacrylamides and -methacrylamides, acrylonitrile, methacrylonitrile, vinyl C1-C18 alkanoates, C2-C18 alkenes, C2-C18 haloalkenes, styrene, (lower alkyl)styrene, C4-C12 alkyl vinyl ethers, C2-C10 perfluoro-alkyl acrylates and methacrylates and correspondingly partially fluorinated acrylates and methacrylates, C3 through C12 perfluoroalkylethylthiocalbonylaminoethyl acrylates and methacrylates, acryloxy- and methacryloxyalkylsiloxanes, N-vinylcarbazole, C1 through C12 alkyl esters of maleic acid, fumaric acid, itaconic acid, mesaconic acid, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexafluoroisopropyl methacrylate, hexafluorobutyl methacrylate, tristrimethylsilyloxysilylpropyl methacrylate (TRIS), and 3-methacryloxypropylpentamethyldisiloxane.

In some embodiments, the hydrophobic polymer is one which displays a relatively high oxygen diffusion rate there through, such as, but not limited to, polysiloxanes, perfluoroalkyl ethers, specific unsaturated polymers, and polysulfones. In one embodiment, the hydrophobic polymer is a polysiloxane block having terminal alkylene groups.

In some embodiments, the hydrophobic polymer includes a perfluoroalkyl-polyether block. In other embodiments, the hydrophobic polymer includes an unsaturated polymer, such as a polymer of a conjugated aliphatic or alicyclic diene, which may be substituted by halogen or lower alkyl, a polymer of an alkyne or dialkyne, which may be substituted by lower alkyl or trimethylsilyl, a copolymer of a conjugated diene and a hydrophilic or hydrophobic vinylic monomer, and also partially hydrated derivatives of these compounds.

Specific examples of polymers of conjugated dienes are cis-, trans-, iso- or syndiotactic poly-1,2-butadiene, poly-1,4-butadiene or polyisoprene, poly-pentenamer, polychloroprene and polypiperylen. Other examples of copolymers are butadiene- or isoprene-copolymers with hydrophilic or hydrophobic vinylic monomers, such as acrylonitrile, styrene, acrylic acid or hydroxyethylmethacrylate. An example of a polyalkyne is poly-1-trimethylsilyl-propyne. In some embodiments, examples of polymers included unsaturated polymers are syndiotactic poly-1,2-butadiene, poly-1,4-butadiene and polyisoprene. An especially preferred unsaturated polymer is poly-1-trimethylsilyl-propyne. Another especially preferred unsaturated polymer is poly-1,4-butadiene.

The hydrophobic polymer may include a single type of polymer or more than one type of polymer, such as two or more of those discussed above. The mean molecular weight of one segment B is in the range from about 500 to about 50,000, preferably in the range from about 800 to about 15,000, more preferably in the range of about 1,000 to 12,000, particularly preferably in the range from about 5,000 to about 12,000.

In some embodiments. in addition to the hydrophobic segment B, the amphiphilic segmented copolymer includes at least one segment A which includes at least one hydrophilic polymer, such as, but not limited to, polyoxazoline, polyethylene glycol, polyethylene oxide, polyvinyl alcohol, polyvinylpyrrolidone, polyacrylamide, poly(meth)acrylic acid, polyethylene oxide-co-polypropyleneoxide block copolymers, poly(vinylether), poly(N,N-dimethylacrylamide), polyacrylic acid, polyacyl alkylene imine, polyhydroxyalkylacrylates such as hydroxyethyl methacrylate (HEMA), hydroxyethyl acrylate, and hydroxypropyl acrylate, polyols, and copolymeric mixtures of two or more of the above mentioned polymers, natural polymers such as polysaccharides and polypeptides, and copolymers thereof, and polyionic molecules such as polyallylammonium, polyethyleneimine, polyvinylbenzyltrimethylammonium, polyaniline, sulfonated polyaniline, polypyrrole, and polypyridinium, polythiophene-acetic acids, polystyrenesulfonic acids, zwitterionic molecules, and salts and copolymers thereof.

In some embodiments, the hydrophilic segment preferably contains a predominant amount of hydrophilic monomers. A hydrophilic comonomer is a monomer that typically gives a homopolymer that is soluble in water or can absorb at least 10% by weight of water.

Suitable hydrophilic monomers are hydroxyl-substituted lower alkyl acrylates and methacrylates, acrylamide, methacrylamide, (lower alkyl) acrylamides and methacrylamides, N,N-dialkyl-acrylamides, ethoxylated acrylates and methacrylates, polyethyleneglycol-mono methacrylates and polyethyleneglycolmonomethylether methacrylates, hydroxyl-substituted (lower alkyl)aciylamides and methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)-(where the term amino also includes quaternary ammonium), mono(lower alkylamino)(lower alkyl) and di(lower alkylamino)(lower alkyl) acrylates and methacrylates, allyl alcohol, 3-trimethylammonium 2-hydroxypropylmethacrylate chloride (Blemer, QA, for example from Nippon Oil), dimethylaminoethyl methacrylate (DMAEMA), dimethylaminoethylmethacrylamide, glycerol methacrylate, and N-(1,1-dimethyl-3-oxobutyl)acrylamide.

In some embodiments, the segment A includes a polymer displaying a relatively high water or ion diffusion rate there through. Specific examples of hydrophilic monomers from which such polymers can be made are cyclic imino ethers, vinyl ethers, cyclic ethers including epoxides, cyclic unsaturated ethers, N-substituted aziridines, beta-lactones and beta-lactames. Further suitable monomers include ketene acetals, vinyl acetals and phosphoranes. Suitable cyclic imino ethers include 2-oxazoline. If a 2-oxazoline having an alkenyl group in 2 position is used as hydrophilic monomer, a polymerizable unsaturated group is provided within segment A (in a side chain) of the amphiphilic segmented copolymer to serve as the polymerizable unsaturated group necessary for the final polymerization to obtain a polymeric product or as an additional polymerizable unsaturated group which offers the possibility of direct crosslinking in the preparation of the polymer. In some embodiments, the cyclic imino ether is 2-methyloxazoline. The most preferred vinyl ethers are methyl vinyl ether, ethyl vinyl ether and methoxy ethyl vinyl ether.

In some embodiments, the mean molecular weight of one segment A is in the range from about 500 to about 50,000, from about 800 to about 15,000, from about 1,000 to 12,000, particularly from about 5,000 to about 12,000.

The mixtures of block copolymers can be mixtures of two or more of the following classes, where the separate components can be of the same class but with a different distribution of polymer blocks:

Polymer source triblock copolymers E/EP/E, of poly (ethylene)(E) and poly(ethylenepropylene)(EP) triblock copolyampholytes. Among (N,N dimethylamino)isoprene, such polymers are Ai14S63A23, Ai31S23A46, Ai42S23A35, styrene, and methacrylic acid Ai56S23A21, Ai57S11A32.

Styrene-ethylene/butylene-styrene (KRATON) G 1650, a 29% styrene, 8000 solution triblock copolymer viscosity (25 wt-% polymer), 100% triblock styrene-ethylene/butylene-styrene (S-EB-S) block copolymer; (KRATON) G 1652, a 29% styrene, 1350 solution viscosity (25 wt-% polymer), 100% triblock S-EB-S block copolymer; (KRATON) G 1657, a 4200 solution viscosity (25 wt-% polymer), 35% diblock S-EB-S block copolymer; all available from the Shell Chemical Company. Such block copolymers include the styrene-ethylene/propylene (S-EP) types and are commercially available under the tradenames (KRATON) G 1726, a 28% styrene, 200 solution viscosity (25 wt-% polymer), 70% diblock S-EB-S block copolymer; (KRATON) G-1701X a 37% styrene, >50,000 solution viscosity, 100% diblock S-EP block copolymer; and (KRATON) G-1702X, a 28% styrene, >50,000 solution viscosity, 100% diblock SEP block copolmyer.

Siloxane triblock copolymer PDMS-b-PCPMS-b-PDMSs (PDMS=polydimethylsiloxane, PCPMS=poly(3-cyanopropylmethylsiloxane) can be prepared through kinetically controlled polymerization of hexamethylcyclotrisiloxane initiated by lithium silanolate endcapped PCPMS macroinitiators. The macroinitiators can be prepared by equilibrating mixtures of 3-cyanopropylmethylcyclosiloxanes (DXCN) and dilithium diphenylsilanediolate (DLDPS). DxCNs can be synthesized by hydrolysis of 3-cyanopropylmethyldichlorosilane, followed by cyclization and equilibration of the resultant hydrolysates. DLDPS can be prepared by deprotonation of diphenylsilanediol with diphenylmethyllithium. Mixtures of DXCN and DLDPS can be equilibrated at 100° C. within 5-10 hours. By controlling the DxCN-to-DLDPS ratio, macroinitiators of different molecular weights are obtained. The major cyclics in the macroinitiator equilibrate are tetramer (8.6+-0.7 wt %), pentamer (6.3+-0.8 wt %) and hexamer (2.1+-0.5 wt %).

2.5 k-2.5 k-2.5 k, 4 k-4-k-4-k, and 8 k-8 k-8 k triblock copolymers have been characterized. These triblock copolymers are transparent, microphase separated and highly viscous liquids. PEO-PDMS-PEO triblock formed from Polyethylene oxide (PEO) and poly-copolymer dimethyl siloxane (PDMS). Functionalized poly (2 methyloxazoline)-block-: These A-B-A polymers include poly(dimethylsiloxane)-block-versions in which the A components have MW of poly(2-methyloxazoline) triblock approximately 2 kDa, and the B component of copolymer approximately 5 kDa, and (b) the A components have MW of approximately 1 kDa, and the B component of approximately 2 kDa. Poly(d/1-lactide) ("PLA")—PEG-PLA triblock copolymer. Poly(styrene-b-butadiene-b-styrene) triblock copolymer.

Poly(ethylene (such polymers included Pluronic F127, Pluronic P105, or oxide)/poly(propylene oxide) Pluronic L44 from BASF (Performance Chemicals). Triblock copolymers PDMS-PCPMS-PDMS. A series of epoxy and vinyl end-capped polysiloxane (polydimethylsiloxane-triblock copolymers with systematically varied molecular polycyanopropylmethylsiloxane) weights can be synthesized via anionic polymerization triblock copolymer using LiOH as an initiator. Polydiene-polystyrene-polydiene available as Protolyte A700 from DAIS-Analytic, Odessa, Fla. Azo-functional styrene-butadiene-HEMA triblock copolymer. Amphiphilic triblock copolymer carrying polymerizable end groups. Syndiotactic polymethylmethacrylate (sPMMA)-polybutadiene (PBD)-sPMMA triblock copolymer. Tertiary amine methacrylate triblock Biodegradable PLGA-b-PEO-b-PLGA triblock copolymer, Polyactide-b-polyisoprene-b-polyactide triblock copolymer, Poly(isoprene-block-styrene-block-dimethylsiloxane) triblock copolymer, Poly (ethylene oxide)-block-polystyrene-block-poly(ethylene oxide) triblock copolymer, Poly(ethylene oxide)-poly(THF)-poly(ethylene oxide) triblock copolymer. Ethylene oxide triblock Poly E-caprolactone (Birmingham Polymers, Birmingham), AL Poly(DL-lactide-co-glycolide) (Birmingham Polymers), Poly(DL-lactide) (Birmingham Polymers), Poly(L-lactide) (Birmingham Polymers), Poly(glycolide) (Birmingham Polymers), Poly(DL-lactide-co-caprolactone) (Birmingham Polymers), Styrene-Isoprene-styrene triblock (Japan Synthetic Rubber Co., Tokyo, Japan) MW=140 kg/mol, copolymer Block ratio of PS/PI=15/85. PM MA-b-PIB-b-PM MA Poly(methyl methacrylate) (PMMA) and polyisobutylene (PIB). PLGA-PEO-PLGA triblock Polymers of poly(DL-lactic acid-co-glycolic acid) copolymer (PLGA) and PEO. Sulfonated styrene/ethylene-butylene/styrene (S-SEBS) triblock copolymer proton conducting membrane. Poly(l-lactide)-block-poly(ethylene oxide)-block-poly(l-lactide) triblock copolymer Poly-ester-ester-ester triblock copolymer PLA/PEO/PLA triblock copolymer. The synthesis of the triblock copolymers can be prepared by ring-opening polymerization of DL-lactide or e-caprolactone in the presence of poly(ethylene glycol), using no-toxic Zn metal or calcium hydride as co-initiator instead of the stannous octoate. The composition of the co-polymers can be varied by adjusting the polyester/polyether ratio.

The above polymers can be used in mixtures of two or more of polymers in the same or different class. For example, in two polymer mixtures measured in weight percent of the first polymer, such mixtures can comprise 10-15%, 15-20%, 20-25%, 25-30%, 30-35%, 35-40%, 40-45% or 45-50%. Or, for example where three polymers are used: the first can comprise 10-15%, 15-20%, 20-25%, 25-30%, 30-35%, 35-40%, 40-45% or 45-50% of the whole of the polymer components, and the second can 10-15%, 15-20%, 20-25%, 25-30%, 30-35%, 35-40%, 40-45% or 45-50% of the remainder.

Preparation of the Amphiphilic Copolymer

In some embodiments, the segments A and B are linked together through a bond that may be hydrolyzable or non-hydrolyzable. A non-hydrolyzable bond is a covalent bond that is not cleaved by an ordinary aqueous or solvent hydrolysis reaction, e.g. under acidic or basic conditions. Specific bonds that are hydrolyzable are well known to those skilled in the art.

A non-hydrolyzable bond between segments A and B in the amphiphilic segmented copolymer can be formed by polymerizing a suitable hydrophilic monomer (from segment A) in the presence of a suitably functionalized hydrophobic monomer (from segment B) such that a block of units of the hydrophilic monomer grows from the site of functionalization of the hydrophilic monomer or, alternatively by polymerizing a suitable hydrophobic monomer in the presence of a suitably functionalized hydrophilic monomer such that a block of units of the hydrophobic monomer grows from the site of functionalization of the hydrophilic monomer.

The functionalized segment is also called a macroinitiator. Suitable macroinitiators include thermally or photochemically activatable cationic or anionic groups, or a thermally or photochemically activatable radical initiator group. Anionic polymerization, polycondensation, and polyaddition can also be used. Specific examples of preferred photochemically activatable cationic initiator groups are triflate (—O—$SO_2$—$CF_3$), —I (iodide), —O-mesyl, —O-tosyl, and —Cl+ $AgSbF_6$. In some embodiments, the preferred initiator group is the triflate group. The initiator group is linked to the starting segment in a way that provides a covalent non-hydrolyzable bond between the terminal group of the starting segment and the first monomer forming the growing segment that is attached to the starting segment during the graft copolymerization for preparing the amphiphilic segmented copolymer. Grafting means that polymer chains are grown from a monomer either in terminal or in pendant position onto another preformed polymer.

The initiator group may be introduced into a preformed polymer in a suitable way, for example through linkage of cationic or thermal initiator groups to functional groups present on the starting monomer. Only the latter method is suitable for providing pendent initiator groups. Preferred triflate groups can be introduced by reaction of terminal or pendent functional hydroxyl groups with activated triflic acid derivatives such as $(CF_3 SO)_2 O$.

A degradable bond between the A segment and the B segment can be used so that the biomimetic membrane (e.g. vesicle) can be degraded. Degradable bonds within the A or B segment can also be used. Biodegradable regions can be constructed from polymers or monomers using linkages susceptible to biodegradation. Degradability can be imparted by inclusion of a single degradable linkage or a degradable region made of more than one degradable linkage. The terms degradable linkage and degradable region are used interchangeably hereinafter.

The degradable region is preferably degradable under in vivo conditions. For example, a degradable region may be a hydrolyzable region, such as made from a polymer or oligomer of glycolide, lactide, epsilon-caprolactone, other hydroxy acids, or other biologically degradable polymer that yields materials that are non-toxic or present as normal metabolites in the body. Regions that are biodegradable by enzymatic degradation can also be used. Preferred poly (alpha-hydroxy acids) are poly(glycolic acid), poly(DL-lactic acid), and poly(L-lactic acid). Other useful materials include poly(amino acids), poly(anhydrides), poly(orthoesters), poly(phosphazines) and poly(phosphoesters). Polylactones such as poly(epsilon-caprolactone), poly(delta-valerolactone), and poly(gamma-butyrolactone), for example, are also useful. The biodegradable region may have a degree of polymerization ranging from one up to values that would yield a product that is not substantially water soluble. Thus, monomeric, dimeric, trimeric, oligomeric, and polymeric regions may be used.

Accordingly, the amphiphilic segmented copolymers may consist in one embodiment of one segment A and one segment B (A-B-type, diblock), or of one segment A and two segments B attached to its termini (B-A-B-type, triblock), or may have a comb-type structure wherein several segments B are pendent from one segment A, which may further carry one or two terminal segments B). In another embodiment, the amphiphilic segmented copolymers may consist of one segment B and two segments A attached to its termini (A-B-A-type, triblock). In another embodiment, the amphiphilic segmented copolymers may have a comb-type structure wherein several segments A are pendent from one segment B, which may further carry one or two terminal segments A. In some embodiments, the copolymer is an ABA or ABC triblock copolymer.

It is also possible to change the monomer during graft copolymerization such that, for example, first hydrophilic segments A are grown on a preformed hydrophobic segment B and then hydrophobic segments B' are attached to the termini of the earlier prepared segments A. Also a different hydrophilic monomer may be used to produce a different hydrophilic segment A' at the termini of the hydrophilic segments A Again, other embodiments of the amphiphilic segmented copolymers may be produced starting from a functionalized hydrophilic segment A.

In some embodiments, the polymer that makes up the starting segment (A or B) usually has a number average molecular weight Mn in the range from about 500 to about 50,000, from about 800 to about 15,000, about 1,000 to 12,000, from about 5,000 to about 12,000. The length of the one or more segments A, B, A', or B' which are to be graft copolymerized on the starting segment can be easily controlled by controlling the amount of monomer (hydrophilic or hydrophobic) which is added for the graft copolymerization. In this way the size of the segments and their ratio can easily be controlled.

The amphiphilic segmented copolymers can be prepared in the presence or absence of a solvent. It is advantageous to use a substantially inert solvent, i.e. one that does not participate in the reaction. Suitable examples are halogenated hydrocarbons, such as chloroform or methylene chloride, bipolar aprotic solvents, such as acetonitrile, acetone, dimethylformamide (DMF) or dimethyl sulfoxide (DMSO), hydrocarbons, such as toluene or xylene, and pyridine or N-methylmorpholine, and mixtures thereof.

In the preparation of the amphiphilic segmented copolymers of the invention, the reaction temperature can be, for example, from $-60°$ C. to $150°$ C., preferably from $0°$ C. to $80°$ C. The reaction times are in the range from about 15 minutes to 7 days, preferably in the region of about 2 to 48 hours. If necessary, the reaction is carried out under argon or nitrogen as protective gas. A suitable catalyst, for example dibutyltin dilaurate (DBTDL), is added in the urethane-forming terminal functionalizing reaction.

In some embodiments, the biomimetic membrane can be crosslinked to provide additional stability. Crosslinking can be achieved using many standard techniques, including photopolymerization, for example, of acrylate groups in the presence of a photoinitiator, or through the use of an alkylating agent. Crosslinking can also be achieved using side groups and end groups which can be polymerized by free radical polymerization, side groups which can be polymerized by cationic polymerization, and side groups which can be polymerized by ring-opening polymerization.

In addition to the hydrophilic and hydrophobic segments, the membranes may also include additional hydrophobic and/or hydrophilic components, as well as crosslinkers such as monomers or macromers with reactive groups, surfactants, and crosslinking initiators, especially photoinitiators. Targeting or biological signal molecules can be attached to the outside surface of the biomimetic membranes (e.g. vesicles).

Polymerization Groups

The segmented copolymers may already contain polymerizable groups in the hydrophobic and/or hydrophilic segments, e.g. if a hydrophobic segment B comprises a diene-polymer like polybutadiene or polyisoprene, or if the monomer used for making a hydrophilic segment comprises an unsaturated side chain, for example 2-allyl-oxazoline. Whether or not present, it is possible to introduce polymerizable groups by suitable reactions, e.g. at the end of or pendent from the growing segments. For this purpose, the graft polymerization of the growing segment may be terminated after a suitable chain length is reached and the initiator group present at the chain end capped, for example, either by using specific reagents such as hydroxy styrene, allyl alcohol, HEMA, propargyl alcohol, allyl amines and propargyl amine, or by using KOH/EtOH or primary amines leaving —OH or —NH— groups or unsaturated groups at the end of the growing segment. Hydroxyl groups may also be introduced into the copolymers by employing suitable comonomers in the graft copolymerization, e.g. 2-hydroxy-alkylox-azolines. The hydroxyl or —NH— groups may then be reacted, e.g. with an isocyanate carrying a polymerizable unsaturated group. Preferred examples of such bifunctional compounds are 2-isocyanatoethyl methacrylate (IEM), which is especially preferred, and vinyl isocyanate, allyl isocyanate, acryloyl isocyanate, styrene isocyanate, vinyl benzyl isocyanate, propargyl isocyanate, and (meth)acrylic anhydride. Other polymerizable groups can be introduced by methods known to those skilled in the art.

Any type of polymerization/crosslinking can be used. Examples include photopolymerization, redox polymerization, anionic polymerization, condensation reactions, addition reactions, and chain polymerization reactions.

Additional Monomers

In some embodiments, the proportion by weight of the amphiphilic segmented copolymer in the biomimetic membrane is in the range from 100 to 50%, in particular in the range from 100 to 80%, preferably in the range from 100 to 90%, based on the total polymeric product. The polymeric biomimetic membrane may be obtained by direct thermal or photochemical polymerization or crosslinking reaction of the amphiphilic segmented copolymer without the addition of comonomers in the presence of a suitable initiator. However, in some cases, it may be preferable to include a comonomer. Types of comonomers that may be desired include hydrophobic or hydrophilic comonomers, or cationic or anionic comonomers. It may also be desirable to include a comonomer that contains a specific functional group, such as a crosslinkable group, or a group that has a particular affinity for a molecule to be incorporated into or onto the membrane, as discussed below. Suitable hydrophobic and hydrophilic comonomers include those discussed above.

The comonomers can be included within the amphiphilic polymer network, or crosslinked as an interpenetrating or semi-interpenetrating network with the amphiphilic polymer. Crosslinking may be achieved with the addition of a comonomer and/or a crosslinking agent, for example, a polyunsaturated comonomer.

Crosslinking Agents

A polymer network can, if desired, be reinforced by addition of a crosslinking agent, for example, a polyunsaturated comonomer. A crosslinked biomimetic membrane including the product of the polymerization and crosslinking reaction of an amphiphilic segmented copolymer, can also be formed, if desired, with at least one vinylic comonomer and with at least one crosslinking agent. Crosslinking can be achieved by a number of different means, such as but not limited to, free radical crosslinking, redox crosslinking, and salt crosslinking.

Examples of suitable crosslinking agents include allyl methacrylate, lower alkylene glycol dimethacrylate, poly (lower alkylene) glycol dimethacrylate, lower alkylene dimethacrylate, divinyl ether, divinyl sulfone, di- and trivinylbenzene, trimethylolpropane trimethacrylate, pentaerythritol tetramethacrylate, bisphenol A dimethacrylate, methylenebis(meth)acrylamide, triallyl phthalate and diallylphthalate, alpha.-.omega.-bis(methacryloxyalkyl)-oligosiloxanes such as bis(methacryloxypropyl)tetramethyldisiloxane, and perfluoroalkyl- or perfluoroalkylether-bis-methacrylates.

The amount of crosslinking agent used is expressed in a proportion by weight based on the total polymer and is in the range from 20 to 0.05%, in particular in the range from 10 to 0.1%, preferably in the range from 5 to 0.1%.

Crosslinking Initiators

The biomimetic membranes are crosslinked in a manner known in the art from the corresponding monomers (the term monomer here also including an amphiphilic segmented copolymer) by a polymerization reaction customary to the person skilled in the art.

In the case of monomers that can be crosslinked with free radical crosslinking, a mixture of monomers is typically warmed with addition of a free-radical former. Examples of such free-radical formers are azoisobutyronitrile (AIBN), potassium peroxodisulfate, dibenzoyl peroxide, hydrogen peroxide, and sodium percarbonate. If, for example, the compounds are warmed, free radicals form with homolysis, and can then initiate polymerization.

A polymerization reaction may be carried out using a photoinitiator that can initiate free-radical polymerization and/or crosslinking. Examples of suitable photoinitiators include benzoin methyl ether, 1-hydroxycyclohexylphenyl ketone, and Darocure and Irgacure products, preferably Darocure 1173®. and Irgacure 2959®. Also suitable are reactive photoinitiators, which can be incorporated, for example, into a macromer, or can be used as a specific comonomer. Examples are described in European Patent No. EP 0 632 329. The photopolymerization can then be initiated by actinic radiation, for example light, in particular UV light having a suitable wavelength. The spectral requirements can, if necessary, be controlled appropriately by addition of suitable photo sensitizers.

The polymerizable regions may be polymerizable by photoinitiation by free radical generation, most preferably in the visible or long wavelength ultraviolet radiation Polymerizable regions are acrylates, diacrylates, oligoacrylates, dimethaciylates, oligomethoacrylates, or other biologically acceptable photopolymerizable groups. A preferred tertiary amine is triethanol amine.

Useful photoinitiators are those that can be used to initiate by free radical generation polymerization of the macromers without cytotoxicity and within a short time frame, minutes at most and most preferably seconds. Preferred dyes as initiators of choice for LWUV initiation are ethyl eosin, 2,2-dimethoxy-2-phenyl acetophenone, other acetophenone derivatives, and camphorquinone. In all cases, crosslinking and polymerization are initiated among copolymers by a light-activated free-radical polymerization initiator such as 2,2-dimethoxy-2-phenylacetophenone or a combination of ethyl eosin ($10^{-4}$-$10^2$ milliM) and triethanol amine (0.001 to 0.1 M), for example.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical that initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by long wavelength ultraviolet light or by laser light of about 514 nm, for example. Lasers may be used to polymerize any nanospheres from a photopolymerizable solution, due to the precise control that can be achieved with the lasers. It is thus possible to make nanospheres as described herein without inclusion of the amphiphilic polymers.

Initiation of polymerization is accomplished by irradiation with light at a wavelength of between about 200-700 nm, most preferably in the long wavelength ultraviolet range or visible range, 320 nm or higher, most preferably about 514 nm or 365 nm. The light-sensitive free-radical polymerization initiator may be a single compound (e.g. 2,2-dimethoxy-2-phenyl acetophenone) or a combination of a dye and a cocatalyst (e.g., ethyl eosis and triethanol amine).

Solvents

Polymerization/crosslinking can be carried out in the presence or absence of a solvent. Suitable solvents are all solvents which dissolve the monomers used, for example, water, alcohols such as lower alkanols like ethanol or methanol, carboxamides such as dimethylformamide, dipolar aprotic solvents such as dimethyl sulfoxide or methyl ethyl ketone, ketones such as acetone or cyclohexanone, hydrocarbons such as toluene, ethers such as THF, dimethoxyethane or dioxane, halogenated hydrocarbons such as trichloroethane, and mixtures of suitable solvents such as mixtures of water and an alcohol, for example, a water/ethanol or water/methanol mixture.

c. Preparation of Biomimetic Membranes

In some embodiments, the polypeptide(s) (e.g. aquaporins and/or hydrophobin) are been reconstituted in biomimetic membranes that are vesicles (e.g., polymer or lipid (e.g. liposomes, micelles, nanoparticles, microbubbles, etc. . . )) prepared by methods known in the art. In some embodiments, the vesicles are supported into a substrate. In some embodiments, the lipid vesicles are transformed into a supported lipid bilayer membranes using a method known in the art such as the Langmuir-Blodgett method. In some embodiments, the vesicles of the invention are coated with one or more hydrophobins as described herein.

In some embodiments, the biomimetic membranes can be formed from lipid or polymer solutions. In some embodiments, the lipid or polymer solutions can be prepared using suitable protocols known in the art.

In some embodiments, the polypeptide(s) (e.g. aquaporins and/or hydrophobin) are been reconstituted in biomimetic membranes that are lipid vesicles, and transformed into a supported lipid bilayer membranes using a method such as the Langmuir-Blodgett method. Intrinsic permeability of the membrane material must be secured. A material with low permeability can be used, however, it must at the same time be robust and able to incorporate the polypeptide(s) to constitute overall a stable and dense 2D filtering array. Various procedures are commonly used for preparing supported bilayers. A simple technique is the Langmuir-Blodgett method. A solution of lipid in a suitable organic solvent is spread on an aqueous sub phase in a Langmuir trough and the organic solvent is evaporated. A pair of movable barriers is used to compress the lipid film laterally to a desired surface pressure. Then the substrate is passed vertically through the film thereby transferring a one molecule thick lipid layer (monolayer) onto the substrate. A second monolayer can be transferred by passing the substrate through the film once more. A total of three monolayers have been transferred by the vertical (Langmuir-Blodgett) deposition method, however, a fourth layer may be transferred by using horizontal, the so called Langmuir-Schaeffer (LS), deposition for the last layer. The methods can be used with a variety of lipids, including those described herein. Native biological membranes often are asymmetric. Both LB and LS offer the possibility of preparing asymmetric bilayers. This is done by exchanging the lipid film on the sub phase between depositions.

Another way of preparing supported bilayers is the vesicle fusion method (A. A. Brian and H. M. McConnell. Allogenic stimulation of cytotoxic T cells by supported planar membranes. Proc. Natl. Acad. Sci. USA, 81:6159-6163, 1984). A solution of small unilamellar vesicles (SUVs) is applied onto the surface of a piece of hydrophilized silicon or freshly cleaved mica. When this sample is left at low temperature (4° C.) the vesicles fuse with the surface to make a continuous bilayer. Without being bound to any theory it has been hypothesized that the vesicles first adsorb to the surface of the substrate then fuse to make a flat, pancake-like structure and finally rupture and spread out resulting in a single bilayer on the surface (I. Reviakine and A. Brisson. Formation of supported phospholipid bilayers from unilamellar vesicles investigated by atomic force microscopy. Langmuir, 16:1806-1815, 2000). It has also been suggested that after fusion with the substrate only the part of the vesicle which is in direct contact with the substrate becomes the supported bilayer (Z. V. Leonenko, A. Carnini, and D. T. Cramb. Supported planar bilayer formation by vesicle fusion: the interaction of phospholipid vesicles with surfaces and the effect of gramicidin on bilayer properties using atomic force microscopy. Biochim. Biophys. Acta, 1509:131-147, 2000). With this mechanism the vesicle ruptures at the edges with the highest curvature and the top part of the bilayer may then migrate to the surface of the substrate to increase the size of the formed supported bilayer. It has been reported that bilayers are formed within minutes of applying the solution onto the substrate but this short incubation time may result in incomplete bilayers. Hours or overnight incubation have also been reported (E. Reimhult, F. Hook, and B. Kasemo. Intact vesicle adsorption and supported biomembrane formation from vesicles in solution: Influence of surface chemistry, vesicle size, temperature, and osmotic pressure. Langmuir, 19:1681-1691, 2003; H. A. Rinia, R. A. Kik, R. A. Demel, M. M. E. Snel, J. A. Killian, J. P. J. M. van der Eerden, and B. de Kruijff. Visualization of highly ordered striated domains induced by transmembrane peptides in supported phosphatidylcholine bilayers. Biochemistry, 39:5852-5858, 2000).

A third technique which can be used to prepare supported bilayers is spin-coating (E. Reimhult, F. Hook, and B. Kasemo. Intact vesicle adsorption and supported biomembrane formation from vesicles in solution: Influence of surface chemistry, vesicle size, temperature, and osmotic pressure. Langmuir, 19:1681-1691, 2003; A. C. Simonsen and L. A. Bagatolli. Structure of spin-coated lipid films and domain formation in supported membranes formed by hydration. Langmuir, 20:9720-9728, 2004). In spin-coating the lipid is dissolved in a suitable solvent and a droplet is placed on the substrate which is then rotated while the solvent evaporates and a lipid coating is produced. Depending on the concentration of the lipid solution the spin-coated film consist of one or more lipid bilayers. However, upon hydration the multiple layers have been shown to be unstable, and usually only one supported bilayer remains on the surface. This procedure is easy and fast and it has been exercised with low-melting lipids (POPC) as well as lipids with intermediate (DPPC) and very high transition temperature (ceramide). Useful lipids include, e.g., phospholipids and amphiphilic lipids.

In some embodiments, peptides and proteins are incorporated in the supported bilayers by using the vesicle fusion technique. Many membrane proteins may denature in organic solvents especially if they contain large domains exposed to the aqueous solution on either side of the membrane. In some embodiments, it is therefore preferred to insert the peptides or proteins in vesicles. Many peptides and proteins (e.g. aquaporins and hydrophobin) can be co-solubilized with lipid in the organic solvent prior to formation of vesicles and the peptide containing vesicles are then applied to the substrate. This has been done with a number of peptides, for example WALP (H. A. Rinia, R. A. Kik, R. A. Demel, M. M. E. Snel, J. A. Killian, J. P. J. M. van der Eerden, and B. de Kruijff. Visualization of highly ordered striated domains induced by transmembrane peptides in supported phosphatidylcholine bilayers. Biochemistry, 39:5852-5858, 2000), gramicidin (J. Mou, D. M. Czajkowsky, and Z. Shao. Gramicidin A aggregation in supported gel state phosphatidylcholine bilayers. Biochemistry, 35:3222-3226, 1996), clavanin A (E. J. M. van Kan, D. N. Ganchev, M. M. E. Snel, V. Chupin, A. van der Bent, and B. de Kruijff. The peptide entibiotic clavanin A interacts strongly and specifically with lipid bilayers. Biochemistry, 42:11366-11372, 2003) and Amyloid β Protein (H. Lin, R. Bhatia, and R. Lal. Amyloid beta-protein forms ion channels: implications for Alzheimer's disease pathophysiology. FASEB J., 15:2433-2444, 2001). In some embodiments, membrane proteins such as aquaporins are inserted into vesicles by other means. This can be done using the strategies for reconstitution of membrane proteins into vesicles as described for cytochrome c oxidase as a model protein in the introduction to chapter 4 on pages 41-45 of the herein incorporated thesis "Supported bilayers as models of biological membranes" by Danielle Keller, February 2005, MEMPHYS-center for biomembrane physics, Physics Department, University of Southern Denmark and Danish Polymer Centre, Riso National Laboratory, Denmark.

Multi layer stacking of the individual 2D-arrays are possible and may be desirable. The final dimensions of the stacked arrays will depend on overall robustness and on intrinsic permeability of the chosen membrane material/ membrane composition. Stacking might depart from a system where proteins trivially are embedded in a single, probably supported, lipid bilayer. A subsequent series of collapsing vesicles events on the supported bilayer could then provide multi layer devices, given that the vesicles prerequisite are reconstituted with an appropriate polypeptide(s) (e.g. aquaporin and/or hydrophobin). Incorporation of the stacked unit-device into a stabilizing membrane or stabilizing polymer matrix and subsequent stitching of these individual units would yield an overall mesh, eventually via self-assembly processes.

In some embodiments, the biomimetic membranes comprise block copolymer membranes simulating a natural environment. In some embodiments, the polypeptide(s) described herein (e.g. aquaporin and/or hydrophobin) are incorporated into the block copolymer membranes simulating a natural environment.

In some embodiments, a method of forming a biocompatible membrane for use with block copolymer-based membrane, is as follows: form a solution of block copolymer in solvent (BC solution). The solution can be a mixture of two or more block copolymers. The solution contains 1 to 90% w/v copolymer, or 2 to 20%, or 5 to 10%, such as 7%. Prepare a polypeptide (e.g. aquaporin) solution in the prepared BC solution, preferably by adding 1.0 to 50.0 mg/mL of the selected polypeptide, or 1.0 to 10.0 mg/mL. Drop a small volume (e.g., 4 microliter) polypeptide/BC solution onto each aperture or each of a subset of apertures, and allow to dry, thereby removing the solvent. Repeat this step as needed to cover all apertures.

The solvent is selected to be miscible with both the water component used in the process and the B component of the block copolymer. Appropriate solvents are believed to include methanol, ethanol, 2-propanol, 1-propanol, tetrahydrofuran, 1,4-dioxane, solvent mixtures that can include more apolar solvents such as dichloromethane so long as the mixture has the appropriate miscibility, and the like. (Solvent components that have any tendency to form protein-destructive contaminants such as peroxides can be appropriately purified and handled) Solvent typically comprises 100% v/v or more of the applied polypeptide/BC solution, preferably 20% or more, and usefully 30% or more.

The above-described method of introducing a polypeptide (s) to a solution containing non-aqueous solvent(s) in the presence of block copolymers serves to stabilize the function of active polypeptides. The non-aqueous components can comprise all of the solvent.

In some embodiments, the biomimetic membrane is composed of one or more vesicles having hydrophilic inner and outer layers and a middle hydrophobic layer. In some embodiments the one or more vesicles are composed of lipids, polymers and/or a combination thereof. In some embodiments, the vesicles can be crosslinked to provide additional stability. It should be understood that, when copolymers are used, the copolymers can be polymerized via end groups, crosslinked via internal crosslinkable groups, or a combination of end group and internal group polymerization/crosslinking can be used. In some embodiments, the invention provides lipid and/or copolymer vesicles supported by a substrate (e.g. microporous substrate). In some embodiments, the supported lipid and/or copolymer vesicles are coated with one or more hydrophobins as described herein.

The biomimetic membranes used in the invention can be prepared according to the teachings in PCT/DK2006/000278, U.S. Pat. No. 8,123,948, US publication number 2004/0049230, US publication number 2011/0020950, US publication number 2011/0046074, WO 2012/161662, and PCT/SG2012/000063.

In some embodiments, the biomimetic membrane may comprise a sandwich construction having at least two permeable support layers separated by at least one lipid bilayer or block copolymer comprising one or more functional polypepeptides (e.g. aquaporin water channels and/or hydrophobin). In some embodiments, the biomimetic membrane may comprise a sandwich construction having at least two permeable support layers separated by at least one or more vesicles (e.g. lipid or polymer) comprising one or more functional polypepeptides (e.g. aquaporin water channels and/or hydrophobin).

In some embodiments, the biomimetic membrane may consist of an amphiphilic biomimetic membrane, such as a membrane comprising lipids described herein, or a block copolymer. In some embodiments, the lipid bilayer(s) essentially consist(s) of amphiphilic lipids selected from the group consisting of phospholipids, phosphoglycerides, sphingolipids, and cardiolipin, as well as mixtures thereof, e.g. phospholipids such as 1,2-dipalmitoyl-sn-phosphatidylcholine (DPPC), or mixtures of phospholipids. Alternatively, the lipid bilayers may consist essentially of or contain polymerizable lipids.

In some embodiments, the biomimetic membrane may consist of polypeptides based thin film composite membranes. Lipid or polymer vesicles containing the functional polypeptides of the invention (e.g. aquaporin water channels and/or hydrophobin) are incorporated in an ultrathin selective layer, and are supported by a substrate (e.g. a microporous substrate). In some embodiments, thin film composite membrane is created on a surface of a porous substrate by interfacial polymerization of an aqueous solution of an (aromatic) amine having an added suspension of amphiphilic lipid/copolymer vesicles followed by addition of an acid chloride solution in an organic solvent to allow the amine and the acyl chloride to form a polyamide active TFC layer wherein. During the formation of thin polyamide film, the vesicles, which may be in the form of liposomes or polymersomes with or without incorporated protein (proteoliposomes or proteopolymersomes), become part of the active layer.

In some embodiments, the biomimetic membrane comprises reconstituted polypeptides (e.g. aquaporin water channels and/or hydrophobin) in lipid bilayers in contact with a porous support. Any suitable support layer that is compatible with the preparation of the biomimetic membranes is encompassed in the methods, compositions and apparatuses of the invention. In some embodiments, aquaporin based thin film composite membranes are provided. Amphiphilic lipid-AQP/HFBII and/or amphiphilic copolymer-AQP/HFBII vesicles can be incorporated with ultrathin selective layer, and then can be supported by a microporous substrate.

Examples of useful support materials with a hydrophilic surface for the preparation of biomimetic membranes according to the invention include but are not limited to, mica such as muscovite, mica tape, polysulfon, $AlO_2$, and polymeric materials having a hydrophilic surface, e.g. cellulose. The support materials are essentially planar which means that the support is preferably planar, but curvature of the support is allowable, such as needed when spirally wound membranes are manufactured. In this case the support material is preferably flexible, such as cellulose membranes.

In some embodiments, the porous support may comprise a material such as mica having an essentially planar structure with a hydrophilic surface and wherein micro or nano pores have been formed, e.g. by etching. Hence, in some embodiments, the permeable support layer comprises an essentially planar, hydrophilic layer comprising mica or mica tape having a layer thickness in the mm to μm scale and wherein nanopores having a diameter of less than approximately 50 nm (typically in the 10-40 nm range) have been formed (e.g. by etching such as by a track-etch technique). The mica is preferably muscovite.

The permeable support layers may also comprise a hydrophilized membrane surface, such as a membrane selected from the group consisting of silicone membranes, polysulfon, $AlO_2$, and polymers such as cellulose having a hydrophilic surface, wherein nanopores having a diameter of less than approximately 50 nm (typically in the 10-40 nm range) have been formed.

The biomimetic membrane comprising the polypeptide(s) described herein (e.g., aquaporin channels and/or hydrophobin) may be a bilayer resembling the natural constitution of biological cell membranes, or the biomimetic membrane may consist of multiple bilayers of fused deposited lipid vesicles. In some embodiments, the lipids are of amphiphilic nature, such as the phospholipids (or phosphoglycerides), sphingolipids and cardiolipin. When depositing the lipid layers on the porous substrate, the polypeptide(s) may preferably be deposited adjacent to or in the preexisting pores in the support material.

In some embodiments, the permeable or porous support used is prepared according to R. M. Webber, J. L. Anderson, M. S. John, Macromolecules 23 (1990), 1026-1034.

In some embodiments, the inventions provides for the reconstitution of polypeptide(s) (e.g., aquaporin water channels and/or hydrophobin) in a planar lipid bilayer assembled around a porous support membrane with a hydrophobic surface, such as Teflon® film, where lipid monolayers assemble on each side of the porous support membrane. In the pores of the porous support membrane lipid bilayers will assemble, where the polypeptide(s) can be reconstituted.

In some embodiments, the invention provides a biomimetic membrane comprising a sandwich construction having at least two lipid monolayers, which, when assembled into one bilayer, comprises functional polypeptides, said at least two lipid monolayers being separated by at least one permeable support layer. In some embodiments, the support layer comprises a hydrophobic perforated material which forms the contact surface with the lipid monolayers and wherein the lipid bilayer is formed in the perforations of the hydrophobic perforated material.

In some embodiments, the invention provides a biomimetic membrane comprising lipid and/or polymer, vesicles, comprising the functional polypeptides of the invention (e.g. aquaporin water channels and/or hydrophobin) supported in a substrate. In some embodiments, the invention provides a biomimetic membrane comprising lipid and/or polymer vesicles, comprising the functional polypeptides of the invention, incorporated into an ultrathin selective layer, and supported by a substrate a microporous substrate.

In some embodiments, the hydrophobic material has a degree of hydrophobicity corresponding to a contact angle of at least 100° C. between a droplet of deionized water and the hydrophobic material, where the contact angle measurement is performed at 20° C. and atmospheric pressure, but higher degrees of hydrophobicity are preferred, such as those corresponding to contact angles of at least 105° C., 110° C., 120° C. and 120° C. In some embodiments. The hydrophobic materials are parafilm or Teflon®.

The hydrophobic material is typically planar (but may be flexible and thus curved) and the perforations are typically evenly distributed and substantially all of substantially the same geometric shape in the intermediate plane between the 2 surfaces of the hydrophobic material.

The "intermediate plane" is defined as the plane consisting of points from which the perpendicular distance to either both of the 2 surfaces of the planar hydrophobic material is the same.

The size of the perforations in the hydrophobic material should merely ensure that stable membranes (e.g., lipid and/or polymers; monolayers or bilayers of amphiphilic lipids and/or polymers) can be formed in the perforations, so they may have sizes in the nm, μm or mm range. The membranes can be in the shape of vesicles (e.g. lipid and/or polymers).

In some embodiments, the hydrophobic material is perforated in such a way that the ratio between perforation are and non-perforated area of the material is maximized, since this provides a maximum area of lipid bilayer with polypeptides that form channels (e.g. aquaporins) to effect water transport. The pattern constituted by the perforations is thus of importance as is the distance between each perforation. An optimum pattern is a hexagonal arrangement of the perforations with a minimum "wall thickness" between each perforation in the pattern. However, at quadratic pattern may also prove sufficient.

In some embodiments, the biomimetic membrane used comprises an amphiphilic biomimetic membrane, such as a membrane comprising lipids described herein. Thus, the lipid bilayer(s) essentially consist(s) of amphiphilic lipids selected from the group consisting of phospholipids, phosphoglycerides, sphingolipids, and cardiolipin, as well as mixtures thereof, e.g. phospholipids such as 1,2-dipalmitoyl-sn-phosphatidylcholine (DPPC), or mixtures of phospholipids. The difference from the first aspect is primarily that the membrane only constitutes a bilayer in areas where the hydrophobic support is perforated, whereas the lipids are organized with their hydrophobic ends facing the hydrophobic support and the hydrophilic ends facing the aqueous environment.

In some embodiments, the biomimetic membranes comprise one or more aquaporin. Examples of aquaporins that can be used for the preparation of biomimetic membranes according to the invention included, but are not limited to: AQP1, TIP, PIP, NIP, and mixtures and hybrids thereof. The aquaporins of plant origin are especially desirable, since the risk of including contaminants, such as pathogenic viruses and prions, which can be harmful to humans is greatly reduced. In addition, the plant aquaporins are natural gene products of plants and can be overexpressed and produced in plants. In some embodiments, the aquaporin water channel is aquaporin Z (AqpZ), which is derived from *E. Coli*. In some embodiments, the aquaporin channels are modified.

In some embodiments, the aquaporin water channel is selected from the group consisting of aquaglyceroporins (GLpF), such as a GLPA channel, a GLPB1 channel, a GLPB2 channel, a GLPB3 channel, and a GLPY2 channel, and mixtures and hybrids thereof.

In some embodiments, the biomimetic membranes further comprise or more hydrophobins in combination with one or more aquaporins. In some embodiments, the hydrophobin is selected from the group consisting of: (a) HFBII (SEQ ID NO: 2; obtainable from the fungus *Trichoderma reesei*); (b) HFBI (SEQ ID NO: 4; obtainable from the fungus *Trichoderma reesei*); (c) SC3 (SEQ ID NO: 6; obtainable from the fungus *Schizophyllum commune*); (d) EAS (SEQ ID NO: 8; obtainable from the fungus *Neurospora crassa*); and (e) TT1 (SEQ ID NO: 10; obtainable from the fungus *Talaromyces thermophilus*); or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core to any thereof.

In some embodiments, the hydrophobin is "HFBII" (SEQ ID NO: 2; obtainable from *Trichoderma reesei*) or a protein having at least 70%, at least 75%, at least 80%, at least 85%, at least 90%, at least 91%, at least 92%, at least 93%, at least 94%, at least 95%, at least 96%, at least 97%, or at least 99% sequence identity in the hydrophobin core thereof.

In some embodiments, the biomimetic membranes used in the invention are enclosed in a stabilizing permeable or porous membrane which may be rigid or flexible and which may serve as protection of the water membrane as well as a pre-filter to exclude coarse particulate matter from the aqueous liquid to be purified. Alternatively or additionally, the biomimetic membrane of the invention may be deposited on a filter disk to create a water filter.

Biomimetic membranes can be formed against a solid material, such as by coating onto glass, carbon that is surface modified to increase hydrophobicity, or a polymer (such as polyvinyl acetate, PDMS, Kapton(R), a perfluorinated polymer, Teflon®, PVDF, PEEK, polyester, or UHMWPE, polypropylene or polysulfone). Polymers such as PDMS provide an excellent support that can be used to establish openings on which biocompatible membranes can be formed.

Useful porous materials for the preparation of biomimetic membranes according to the Mueller based lipid bilayer membranes (Mueller, D., Rudin, O., Tien, H. T. and W. C. Wescott. Reconstruction of cell membrane structure in virto and its transformation into an excitable system. Nature (Lond.) 194: 979-980, 1962) or the Montal decane based membranes (Montal, M., and P. Mueller. Formation of bimolecular membranes from monolayers and study of their properties. Proc. Natl. Acad. Sci. USA. 69:3561-3566, 1972) are, Teflon® films and other porous membrane materials with hydrophobic surface properties.

The invention also relates to the upscaling of the biomimetic membranes, where multiple holes are formed in a Teflon® partition film or another material with hydrophobic surface properties, and a lipid bilayer membrane or a block copolymer membrane comprising the polypeptide(s) are formed around the material.

Useful materials for the stabilizing membrane optionally used to enclose the biomimetic membranes described herein are micro-porous silicone membranes having a relatively small pore size and which solidifies at about room temperature or at a temperature below about 50° C.

c. Linking Carriers

In some embodiments, the biomimetic membranes comprise a linking carrier. The term linking carrier includes entities that serve to link agents, e.g., targeting agents, to the biomimetic membranes. In some embodiments, the linking carrier confers additional advantageous properties to the biomimetic membranes. Examples of these additional advantages include, but are not limited to: 1) multivalency, which is defined as the ability to attach multiple agents to the biomimetic membranes; and 2) improved stability.

In some embodiments, the linking carriers are biocompatible polymers (such as dextran) or macromolecular assemblies of biocompatible components. Examples of linking carriers include, but are not limited to, microbubbles, polymerized microbubbles, micelles, liposomes, other lipid vesicles, dendrimers, polyethylene glycol assemblies, capped polylysines, poly(hydroxybutyric acid), dextrans, and coated polymers.

The linking carrier can be coupled to an agent (e.g. stabilizing agent) by a variety of methods, depending on the specific chemistry involved. The coupling can be covalent or non-covalent. A variety of methods suitable for coupling of the targeting entity and the therapeutic entity to the linking carrier can be found in Hermanson, "Bioconjugate Techniques", Academic Press: New York, 1996; and in "Chemistry of Protein Conjugation and Cross-linking" by S. S. Wong, CRC *Press,* 1993. Specific coupling methods include, but are not limited to, the use of bifunctional linkers, carbodiimide condensation, disulfide bond formation, and use of a specific binding pair where one member of the pair is on the linking carrier and another member of the pair is on the therapeutic or targeting entity, e.g. a biotin-avidin interaction.

d. Other Stabilizing Entities

In some embodiments, the biomimetic membranes contain a stabilizing entity. As used herein, "stabilizing" refers to the ability to impart additional advantages to the biomimetic membranes, for example, physical stability, e.g., longer half-life, colloidal stability, and/or capacity for multivalency; that is, increased payload capacity due to numerous sites for attachment of targeting agents. Stabilizing entities include macromolecules or polymers, which may optionally contain chemical functionality for the association of the stabilizing entity to the surface of the biomimetic membrane, and/or for subsequent association of therapeutic agents and/or targeting agents. The polymer should be biocompatible with aqueous solutions. Polymers useful to stabilize the biomimetic membranes of the present invention may be of natural, semi-synthetic (modified natural) or synthetic origin. A number of stabilizing entities which may be employed in the present invention are available, including xanthan gum, acacia, agar, agarose, alginic acid, alginate, sodium alginate, carrageenan, gelatin, guar gum, tragacanth, locust bean, bassorin, karaya, gum arabic, pectin, casein, bentonite, unpurified bentonite, purified bentonite, bentonite magma, and colloidal bentonite.

Other natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrose, dextrin, glucose, polyglucose, polydextrose, pustulan, chitin, agarose, keratin, chondroitin, dermatan, hyaluronic acid, alginic acid, xanthin gum, starch and various other natural homopolyner or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Other suitable polymers include proteins, such as albumin, polyalginates, and polylactide-glycolide copolymers, cellulose, cellulose (microcrystalline), methylcellulose, hydroxyethylcellulose, hydroxypropylcellulose, hydroxypropylmethylcellulose, carboxymethylcellulose, and calcium carboxymethylcellulose.

Exemplary semi-synthetic polymers include carboxymethylcellulose, sodium carboxymethylcellulose, carboxymethylcellulose sodium 12, hydroxymethylcellulose, hydroxypropylmethylcellulose, methylcellulose, and methoxycellulose. Other semi-synthetic polymers suitable for use in the present invention include carboxydextran, aminodextran, dextran aldehyde, chitosan, and carboxymethyl chitosan.

Exemplary synthetic polymers include poly(ethylene imine) and derivatives, polyphosphazenes, hydroxyapatites, fluoroapatite polymers, polyethylenes (such as, for example, polyethylene glycol, the class of compounds referred to as Pluronics®, commercially available from BASF, (Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof, polysorbate, carbomer 934P, magnesium aluminum silicate, aluminum monostearate, polyethylene oxide, polyvinylalcohol, povidone, polyethylene glycol, and propylene glycol. Methods for the preparation of biomimetic membranes which employ polymers to stabilize biomimetic membranes compositions will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

In some embodiments, the stabilizing entity is dextran. In some embodiments, the stabilizing entity is a modified dextran, such as amino dextran. In some embodiments, the stabilizing entity is poly(ethylene imine) (PEI).

In some embodiments, the following polymers and their derivatives are used: poly(galacturonic acid), poly(L-glutamic acid), poly(L-glutamic acid-L-tyrosine), poly [R)-3-hydroxybutyric acid], poly(inosinic acid potassium salt), poly(L-lysine), poly(acrylic acid), poly(ethanolsulfonic acid sodium salt), poly(methylhydrosiloxane), polyvinyl alcohol), poly(vinylpolypyrrolidone), poly(vinylpyrrolidone), poly(glycolide), poly(lactide), poly(lactide-co-glycolide), and hyaluronic acid. In some embodiments, copolymers including a monomer having at least one reactive site, or multiple reactive sites, are used for the attachment of the copolymer to the biomimetic membrane or other molecules.

In some embodiments, the polymer may act as a hetero- or homobifunctional linking agent for the attachment of agents, proteins or chelators such as DTPA and its derivatives.

In some embodiments, the stabilizing entity is associated with the biomimetic membranes by covalent means. In another embodiment, the stabilizing entity is associated with the biomimetic membranes by non-covalent means. Covalent means for attaching the targeting entity with the biomimetic membranes are known in the art and described in the US publication 2010/0111840, incorporated by reference herein in its entirety.

Noncovalent means for attaching agents to the biomimetic membranes include but are not limited to attachment via ionic, hydrogen-bonding interactions, including those mediated by water molecules or other solvents, hydrophobic interactions, or any combination of these.

In some embodiments, the stabilizing agent forms a coating on the biomimetic membrane.

In some embodiments, the biomimetic membranes of the invention may also be linked to functional agents, such as poly(ethylene glycol) (PEG), that otherwise modify the biomimetic membrane properties, such as aggregation tendencies, binding by opsonizing proteins, uptake by cells, and stability.

e. Uses of Membranes

In some embodiments, the biomimetic membranes comprise functional molecules, such as channel forming molecules, e.g. certain peptides or peptide like molecules including amphotericin B, alamethicin, valinomycin, gramicidin A and their dimers, oligomers and analogues thereof; or transmembrane proteins, e.g. aquaporin water channels, Fas protein, DsbB, CFTR, alpha-haemolysin, VDAC, and OmpG.

In some embodiments, the present invention relates to biomimetic membranes comprising functional channel forming molecules. In some embodiments, the channel-forming molecule is selected among the aquaporin water channels to make it possible to obtain a biomimetic membrane useful in a filtration device for purification of a water source or a liquid, aqueous medium. In some embodiments, the biomimetic membranes further comprises one or more hydrophobins. Other useful applications include a biosensor or for high throughput screening of ligands.

In some embodiments, the invention provides membrane scaffold containing apertures and the formation of bilayer biomimetic membranes in said apertures In some embodiments, the biomimetic membranes of the invention are suitable for incorporation of biomolecules that are naturally membrane-bound, e.g. aquaporins, or for incorporation of artificial molecules. The biomimetic membranes comprising aquaporins are suitable for transporting water from one side of the membrane to the other side, e.g. when driven by a pressure gradient. The ability to transport water may be utilized in a filtration device for preparing essentially pure water. This facilitates processes such as water purification, desalinization, and molecular concentration through dialysis. Other embodiments of the biomimetic membranes are suitable as biosensors or for high throughput screening of transmembrane protein ligands. In some embodiments, the channel-forming molecules cover at least 1% of the membrane surface. In some embodiments, the membrane is covered with 1 to 10% of the channel-forming molecules.

In some embodiments, the invention relates in a further aspect to a filtration device for filtering essentially pure water comprising a biomimetic membrane comprising aquaporin water channels and one or more hydrophobins, as described above. The advantages of using the biomimetic membrane in said filtering device or other applications where upscale is an advantage is closely related to the possibility of up-scaling the functional membrane area by the manufacturing of large, flexible, and relatively thin sheets having a large multitude of discrete membrane units. In addition, the biomimetic membrane ensures that filtering ability is maintained even though one or more discrete membrane units have failed. This situation may especially apply to a filtration device having multi layer stacking of the individual biomimetic membranes or 2D-aperture-arrays.

In some embodiments, the present invention provides biomimetic membranes comprising one or more polypeptides (e.g. aquaporins and/or hydrophobin) used for pressure retarded osmosis. In some embodiments, the present invention provides the implementation of said membrane in a pressure-retarded osmosis (PRO) system used in the production of salinity power. In some embodiments, the present invention provides biomimetic membranes comprising aquaporins and/or hydrophobin used for PRO. The lipids membranes comprising one or more polypeptides (e.g. aquaporins and/or hydrophobin) can be produced using multiple different procedures known in the art, including those described herein.

In some embodiments, the invention includes the use of the membrane to extract excess water from aqueous substances or solutions, e.g. to obtain increased concentration of a desirable solute.

In some embodiments, proteins in the biomimetic membrane can be used to transport electrons/protons to enable the transduction of electrical and chemical power, and act as mechanical valves and sensors.

In some embodiments, the biomimetic membrane is used to provide a biosolar-powered material which comprise of a biomimetic membrane embedded with one or more energy converting proteins, e.g., bacteriorhodopsin and cytochrome oxydase, which will convert optical energy to electrical energy and deliver this energy to an external load. In some embodiments, the biosolar-powered material further comprises a fabric which consists of a thin fabric incorporating the lipid polymer membrane embedded with the one or more energy converting proteins as described in US publication no. 2004/0049230.

Other useful applications of said biomimetic membranes include biosensor applications, such as a transmembrane protein functioning as receptor or channel, labeled with a fluorophore to make a protein-based biosensor sensitive to ligands, solutes or small molecules. Said biosensors incorporated into biomimetic membranes can be used for ligand-receptor interactions used in high throughput screening assays for diagnostic or prognostic purposes prepared in 96-multi well plates, lab-on-a-chip devices or build into point-of-care measuring devices, or serve as quantitative measuring devices of solutes or small molecules such as heavy metal ions e.g. cadmium, copper, lead, etc., or antibiotics and other polluting agents for quantitative on-the-spot water analysis, or blood analysis of animals and humans.

In some embodiments of the present invention involves the use of biomimetic membranes for the classification, diagnosis, prognosis of a condition, determination of a condition stage, determination of response to treatment, monitoring and predicting outcome of a condition. Another embodiment of the invention involves the use of the biomimetic membranes described herein in monitoring and predicting outcome of a condition. Another embodiment of the invention involves the use of the biomimetic membranes described herein in drug screening, to determine which drugs may be useful in particular diseases. Another embodiment of the invention involves the use of the biomimetic membranes described herein for the treatment of a condition.

In some embodiments, the methods involve the administration of one or more biomimetic membranes for the treatment of one or more conditions. Combinations of agents can be used to treat one condition or multiple conditions or to modulate the side-effects of one or more agents in the combination.

The term "treating" and its grammatical equivalents as used herein includes achieving a therapeutic benefit and/or a prophylactic benefit. By therapeutic benefit is meant eradication or amelioration of the underlying condition being treated. Also, a therapeutic benefit is achieved with the eradication or amelioration of one or more of the physiological symptoms associated with the underlying condition such that an improvement is observed in the patient, notwithstanding that the patient may still be afflicted with the underlying condition. For prophylactic benefit, the compositions may be administered to a patient at risk of developing a particular disease, or to a patient reporting one or more of the physiological symptoms of a disease, even though a diagnosis of this disease may not have been made.

As used herein the term "diagnose" or "diagnosis" of a condition includes predicting or diagnosing the condition, determining predisposition to the condition, monitoring treatment of the condition, diagnosing a therapeutic response of the disease, and prognosis of the condition, condition progression, and response to particular treatment of the condition.

Methods

In some embodiments, the present invention provides methods for stabilizing a membrane protein, a membrane, and/or a membrane comprising a membrane protein using one or more hydrophobins. In some embodiments, the present invention provides methods for stabilizing a biomimetic membrane using one or more hydrophobins. In some embodiments, the present invention provides methods for stabilizing membrane protein using one or more hydrophobins. In some embodiments, the present invention provides methods for stabilizing a biomimetic membrane containing a membrane protein using one or more hydrophobins.

In some embodiments, the methods of the invention comprise adding one or more hydrophobins to a membrane protein to stabilize the membrane protein. In some embodiments, the membrane protein is an isolated and/or purified membrane protein. In some embodiments, the one or more hydrophobins are added to the membrane protein in an amount sufficient to increase the stability of the membrane protein. In some embodiments, the one or more hydrophobins are added to the membrane protein in an amount sufficient to increase the thermal stability of the membrane protein.

In some embodiments, the methods of the invention for stabilizing a membrane protein comprise adding one or more hydrophobins to a membrane protein to disperse the membrane protein. Thus, in some embodiments, the membrane protein molecules are held in dispersion in a medium. In some embodiments, the membrane protein is an isolated and/or purified membrane protein. In some embodiments, the one or more hydrophobins are added to the membrane protein in an amount sufficient to disperse the membrane protein. The invention provides stable dispersions of the membrane proteins. The dispersed membrane protein can then be used in the formation of biomimetic membranes.

In some embodiments, the methods of the invention comprise adding one or more hydrophobins to a biomimetic membrane to stabilize the biomimetic membrane. In some embodiments, the one or more hydrophobins are added to the biomimetic membrane in an amount sufficient to increase the stability of the biomimetic membrane protein. In some embodiments, the one or more hydrophobins are added to the biomimetic membrane in an amount sufficient to increase the thermal stability of the biomimetic membrane.

In some embodiments, the methods of the invention comprise adding one or more hydrophobins to a biomimetic membrane containing a membrane protein to stabilize the biomimetic membrane and/or the membrane protein. In some embodiments, the one or more hydrophobins are added to the biomimetic membrane containing a membrane protein in an amount sufficient to increase the stability of the biomimetic membrane protein and/or the membrane protein. In some embodiments, the one or more hydrophobins are added to the biomimetic membrane containing the membrane protein in an amount sufficient to increase the thermal stability of the biomimetic membrane and/or the membrane protein. In some embodiments, the hydrophobin concentration is between 0.01 mM-1 M. In some embodiments, the hydrophobin concentration is between 0.01 mM-0.05 mM. In some embodiments, the hydrophobin concentration is between 0.01 mM-20 mM. In some embodiments, the hydrophobin concentration is between 0.1 mM-0.5 M. In some embodiments, the hydrophobin concentration is between 0.1 mM-200 mM. In some embodiments, the hydrophobin concentration is between 0.1 mM-100 mM. In some embodiments, the hydrophobin concentration is between 0.1 mM-100 mM. In some embodiments, the hydrophobin concentration is between 0.1 mM-50 mM. In some embodiments, the hydrophobin concentration is between 0.1 mM-20 mM. In some embodiments, the hydrophobin concentration is between 0.1 mM-10 mM. In some embodiments, the hydrophobin concentration is between 0.1 mM-5 mM. In some embodiments, the hydrophobin concentration is between 0.1 mM-1 mM. In some embodiments, the hydrophobin is present in a concentration of 0.1 $\mu$M-50 mM. In some embodiments, the hydrophobin is present in a concentration of 0.1-20% by weight of the total weight of the composition.

In some embodiments, the methods of the invention for stabilizing a biomimetic membrane comprise adding one or more hydrophobins as an emulsifier to facilitate the biomimetic membrane formation. In some embodiments, the biomimetic membrane is a lipid or polymer vesicle (e.g. liposome or polymerosome). In some embodiments, the methods of the invention for stabilizing a biomimetic membrane comprise adding one or more hydrophobins as an emulsifier to facilitate lipid/polymer vesicle formation and to modulate the lipid/polymer vesicle size distribution.

In some embodiments, the methods of the invention comprise adding one or more hydrophobins to disperse a membrane protein, to emulsify lipid/polymer vesicle (e.g. liposome or polymerosome) formation, and to form a continuous coating on said lipid/polymer vesicles.

In some embodiments, the methods of stabilizing a membrane protein comprise the following steps: (a) providing an isolated membrane protein; (b) adding the isolated membrane protein to an aqueous solution; and (c) adding one or more hydrophobins as described herein. The steps (b) and (c) in the method above can be performed simultaneously or sequentially.

In some embodiments, the methods comprise the following steps: (a) providing an isolated membrane protein and (b) drying the membrane protein on a surface in the presence of one or more hydrophobins.

The surface can be any surface that does not react with the membrane protein and/or the one or more hydrophobins. Exemplary surfaces include, but are not limited to, glass slides, plastic slides, a multi-well plate and the like. As used herein, drying is meant to include the removal of water or dehydration of the membrane protein. Drying can be accomplished by methods well known in the art such as lyophilization and/or flash freezing in liquid nitrogen.

In some embodiments, the methods of stabilizing a biomimetic membrane comprise the following steps: (a) providing the biomimetic membrane; and (b) adding one or more hydrophobins as described herein to the biomimetic membrane.

In some embodiments, the methods of stabilizing a biomimetic membrane comprise the following steps: (a) providing the components (e.g. lipid and/or polymers) for the formation of the biomimetic membrane, (b) adding one or more hydrophobins as described herein to the components, and (c) forming the biomimetic membrane. The steps (a) and (b) in the method above can be performed simultaneously or sequentially. Thus, the invention provides methods for forming the biomimetic membrane in the presence of one or more hydrophobins as described herein.

In some embodiments, the methods of stabilizing a biomimetic membrane containing a membrane protein comprise the following steps: (a) providing a membrane protein; (b) adding one or more hydrophobins, as described herein, to the membrane protein; and (c) adding the one or more hydrophobins and the membrane protein to a biomimetic membrane. In some embodiments, the membrane protein, the one or more hydrophobins and the components that form the biomimetic membrane (e.g. lipid and/or polymer) are added simultaneously.

In some embodiments, the methods of stabilizing a biomimetic membrane containing a membrane protein comprise the following steps: (a) providing a biomimetic membrane containing the membrane protein; and (b) adding one or more hydrophobins, as described herein, to the biomimetic membrane.

In some embodiments, the biomimetic membrane is a vesicle.

In some embodiments, the invention provides methods of stabilizing a biomimetic membrane containing one or more aquaporin water channels. In some embodiments, the methods comprise adding the one or more aquaporin water channels and one or more hydrophobins to a lipid membrane film hydrations step during a lipid vesicle formations using any suitable method known in the art, including the ones described herein. In some embodiments, the methods comprise the steps of: (a) forming aquaporin-lipid vesicles, and (b) adding one or more hydrophobins to the lipid vesicles. In some embodiments, the methods comprise (a) forming aquaporin-lipid vesicles, (b) depositing the vesicles in an air/water interface and, (c) adding one or more hydrophobins. In some embodiments, the methods comprise forming aquaporin/hydrophobin lipid vesicles.

In some embodiments, the methods comprise adding the one or more aquaporin water channels and one or more hydrophobins to a lipid vesicle formation step using any suitable method known in the art, including the ones described herein.

In some embodiments, the methods comprise adding the one or more aquaporin water channels and one or more hydrophobins to a polymer vesicle formation step using any suitable method known in the art, including the ones described herein. In some embodiments, the methods comprise the steps of: (a) forming aquaporin-polymer vesicles, and (b) adding one or more hydrophobins to the polymer vesicles. In some embodiments, the methods comprise (a) forming aquaporin-polymer vesicles, (b) depositing the vesicles in an air/water interface and, (c) adding one or more hydrophobins. In some embodiments, the methods comprise forming aquaporin/hydrophobin polymer vesicles.

In some embodiments, the one or more hydrophobins and the one or more aquaporin water channels are incorporated into the lipid/polymer vesicles during formation of the vesicle, by including it in the lipid/polymer solution. The one or more hydrophobins and the one or more aquaporin water channels can also or alternatively be incorporated into the vesicle after the vesicle has been formed. In some embodiments, the one or more hydrophobins and the one or more aquaporin water channels are incorporated into the lipid/polymer vesicles before or after the membrane is polymerized and/or crosslinked.

In some embodiments, the one or more hydrophobins is added to the biomimetic membrane, the membrane protein and/or a biomimetic membrane containing the membrane protein at a concentration that is based on the critical aggregation concentration (CAC) of the one or more hydrophobins. The term "critical aggregation concentration" or "CAC" is the concentration above which the hydrophobins or other surfactants aggregate or form regular shaped structures, such as micelles, nanotubes or nanovessicles. The CAC of surfactants can be determined experimentally using known dynamic light scattering methods. A minimal amount of sample can be used in this method. Each CAC determination takes a few hours, therefore it is possible to determine the CAC for a large number of peptide detergents in a few weeks. It is known that the lower the CAC, the more hydrophobic the detergents and the stronger the aggregation in water.

In some embodiments, the one or more hydrophobins are added to the biomimetic membrane, the membrane protein and/or a biomimetic membrane containing the membrane protein at a concentration from about 1 times the CAC of the one or more hydrophobins (1×CAC) to a concentration that is about 30 times the CAC of the one or more hydrophobins (30×CAC). In some embodiments, the one or more hydrophobins are added to the biomimetic membrane, the membrane protein and/or a biomimetic membrane containing the membrane protein at a concentration which is at least 1.5 times the CAC of the one or more hydrophobins (1.5×CAC). In some embodiments, the one or more hydrophobins are added at a concentration that is at least 2 times the CAC of the one or more hydrophobins (2×CAC). In some embodiments, the one or more hydrophobins are added at a concentration that is at least 5 times the CAC of the one or more hydrophobins (5×CAC). In some embodiments, the one or more hydrophobins are added at a concentration that is at least 10 times the CAC of the one or more hydrophobins (10×CAC). In some embodiments, the one or more hydrophobins are added at a concentration that is at least 12 times the CAC of the one or more hydrophobins (12×CAC). In some embodiments, the one or more hydrophobins are added at a concentration that is at least 15 times the CAC of the one or more hydrophobins (15×CAC). In some embodiments, the one or more hydrophobins are added at a concentration that is at least 20 times the CAC of the one or more hydrophobins (20×CAC).

In some embodiments, the one or more hydrophobins are added to the biomimetic membrane, the membrane protein and/or a biomimetic membrane containing the membrane protein on or in a dry surface. In some embodiments, the one or more hydrophobins are added to the biomimetic membrane, the membrane protein and/or a biomimetic membrane containing the membrane protein in an aqueous medium. In some embodiments, the aqueous medium is an aqueous solution. In a further embodiment, the one or more hydrophobins are added to the biomimetic membrane, the membrane protein and/or a biomimetic membrane containing the membrane protein in an ionic solution. In some embodiments, the method comprises the addition of a single type of hydrophobin. In some embodiments, the method comprises the addition of at least two different hydrophobins.

In some embodiments, a surfactant peptide and/or a non-peptide surfactant can be added to the biomimetic membrane, the membrane protein and/or a biomimetic membrane containing the membrane protein. A surfactant is a compound that is amphiphilic or that contains both hydrophobic groups (their "tails") and hydrophilic groups (their "heads"). Surfactants are soluble in both organic solvents and water. There are generally two types of surfactants, ionic and non-ionic surfactants. Ionic surfactants are surfactants that have a net charge at their heads. Non-ionic surfactants are surfactants that have no net charge at their heads. Examples of non-peptide surfactants include, but are not limited to polyoxyalkylene sorbitan fatty acid esters, sorbitan fatty acid esters, alkylene glycol fatty acid esters, polyoxyalkylene fatty acid esters, fatty acid esters, polyoxyalkylene fatty acid ethers, $C_{16}C_{24}$ fatty acids, fatty acid mono-, di- or poly-glycerides, polyoxyalkylene alkyl phenols, alkyl phenyl ethers, polyoxyethylene polyoxypropylene block copolymers, fatty amine oxides, fatty acid alkanolamides, alkyl cellulose, carboxyalkyl cellulose and polyoxyalkylene castor oil derivatives. Ionic surfactants include, but are not limited to, alkyl sulfates, olefin sulfates, ether sulfates, monoglyceride sulfates, alkyl sulfonates, aryl sulfonates, olefin sulfonates, alkyl sulfosuccinates, aryl sulfosuccinates, including sodium lauryl sulfate, dioctyl sodium sulfosuccinate and dioctyl sodium sulfonate), benzalkonium salts, polyoxyalkylene alkylamines, alkylamines, alkanolamine fatty acid esters, quaternary ammonium fatty acid esters, dialkyl ammonium salts, alkyl pyridinium salts including stemylamine and triethanolamine oleate, benzethonium chloride. Non-limiting examples of non-peptide surfactant are lauryldimethyamine oxide (LDAO), n-dodecyldimethyamine N-oxide (NDAO), Octyldimethyamine N-oxide (ODAO), undecyldimethyamine N-oxide (UDAO), Octyl-.beta.-D-glucose (beta-OG), Decyl-beta-D-glucose (beta-DG), Nonyl-beta-D-glucose (beta-NG), Dodecyl-beta-D-maltoside (DDM), Octyanoylsucrose (OS), Octyl-beta-D-galactoside (beta-OGal) and Dodecyl phosphocholine (DPC). In some embodiments, the non-peptide surfactant used in the method of the invention is a non-ionic surfactant. In a further embodiment, the non-ionic surfactant is selected from the group consisting of n-dodecyl-B-D-maltoside and octyl-D-glucoside. In some embodiments, the non-peptide surfactant is added in an amount between about 2 and about 200 times the CAC of the non-peptide surfactant.

In some embodiments, addition of one or more hydrophobins provides at least about a 1.2-fold increase in stability of a biomimetic membrane, a membrane protein and/or a biomimetic membrane containing the membrane protein compared to the stability in the absence of the one or more hydrophobins. In another embodiment, addition of one or more hydrophobins provides at least about 1.5, at least about 1.7, at least about 2.0, at least about 2.2, at least about 2.3 or at least about 2.5-fold increase in stability a biomimetic membrane, a membrane protein and/or a biomimetic membrane containing the membrane protein compared to the stability in the absence of the one or more hydrophobins.

In some embodiments, addition of one or more hydrophobins provides a decrease in the equilibrium surface tension at a biomimetic membrane (e.g. a biomimetic membrane containing one or more membrane proteins) below 50 mN/m. In some embodiments, such a reduction in the equilibrium surface tension at a biomimetic membrane may be achieved using one or more hydrophobins at a concentration of between 0.01-100 mM, 0.01-50 mM or 0.01-20 mM. In some embodiments, the hydrophobin is present in a concentration of 0.1 µM-50 mM. In some embodiments, the hydrophobin is present in a concentration of 0.1-20% by weight of the total weight of the composition. In some embodiments such a reduction in the equilibrium surface tension at a biomimetic membrane may be achieved at a temperature ranging from 0-90° C.

In some embodiments, the one or more hydrophobins may cause the surface shear elasticity at a biomimetic membrane (e.g. a biomimetic membrane containing one or more membrane proteins) to increase to 30-35 mN/m, 40-50 mN/m, or higher. In some embodiments, the one or more hydrophobins may cause the surface shear elasticity at a biomimetic membrane (e.g. a biomimetic membrane containing one or more membrane proteins) to increase to 0.3-0.6 N/m, or higher. In some embodiments, such surface shear elasticity at a biomimetic membrane may be achieved using one or more hydrophobins at a concentration of between 0.01-100 mM, 0.01-50 mM or 0.01-20 mM. In some embodiments, the hydrophobin is present in a concentration of 0.1 µM-50 mM. In some embodiments, the hydrophobin is present in a concentration of 0.1-20% by weight of the total weight of the composition. In some embodiments, such surface shear elasticity at a biomimetic membrane may be achieved at a temperature ranging from 0-90° C.

Kits

The present invention also encompasses kits for stabilizing membrane proteins and/or biomimetic membranes. The kit comprises a composition comprising a membrane protein and a composition comprising one or more hydrophobins as described herein. Kits according to the invention may further comprise a composition comprising a peptide surfactant and/or non-peptide surfactant.

In some embodiments, the kit comprises one or more components for the formation of a biomimetic membrane. In some embodiments, the kit comprises one or more biomimetic membranes.

The kit may further comprise one or more other components for a particular application (e.g. water filtering device).

Host Cell

The term "host cell"—in relation to the present invention includes any cell that comprises either a nucleotide sequence or an expression vector as described herein and which is used in the recombinant production of a protein having the specific properties as defined herein.

Thus, a further embodiment of the present invention provides host cells transformed or transfected with a nucleotide sequence that expresses the protein(s) of the present invention. The cells will be chosen to be compatible with the said vector and may for example be prokaryotic (for example bacterial), fungal, yeast or plant cells. Preferably, the host cells are not human cells.

Examples of suitable bacterial host organisms are gram positive or gram negative bacterial species.

Depending on the nature of the nucleotide sequence encoding the protein of the present invention, and/or the desirability for further processing of the expressed protein, eukaryotic hosts such as yeasts or other fungi may be preferred. However, some proteins are either poorly secreted from the yeast cell, or in some cases are not processed properly (e.g., hyper-glycosylation in yeast).

The use of suitable host cells—such as yeast, fungal and plant host cells—may provide for post-translational modifications (e.g., myristoylation, glycosylation, truncation, lipidation and tyrosine, serine or threonine phosphorylation, or N-terminal acetylation as may be needed to confer optimal biological activity on recombinant expression products of the present invention.

The host cell may be a protease deficient or protease minus strain.

The genotype of the host cell may be modified to improve expression.

Examples of host cell modifications include protease deficiency, supplementation of rare tRNAs, and modification of the reductive potential in the cytoplasm to enhance disulphide bond formation.

For example, the host cell *E. coli* may overexpress rare tRNAs to improve expression of heterologous proteins as exemplified/described in Kane (*Curr Opin Biotechnol* (1995), 6, 494-500 "Effects of rare codon clusters on high-level expression of heterologous proteins in *E. coli*"). The host cell may be deficient in a number of reducing enzymes thus favoring formation of stable disulphide bonds as exemplified/described in Bessette (*Proc Natl Acad Sci USA* (1999), 96, 13703-13708 "Efficient folding of proteins with multiple disulphide bonds in the *Escherichia coli* cytoplasm").

Isolated

In one aspect, the polypeptide(s) for use in the present invention may be in an isolated form. The terms "polypeptide", "protein", "peptide" and "amino acid sequence" are used herein interchangeably.

The term "isolated" means that the sequence or protein is at least substantially free from at least one other component with which the sequence or protein is naturally associated in nature and as found in nature.

Purified

In one aspect, the polypeptide(s) for use in the present invention may be used in a purified form.

The term "purified" means that the sequence is in a relatively pure state—e.g., at least about 51% pure, or at least about 75%, or at least about 80%, or at least about 90% pure, or at least about 95% pure or at least about 98% pure.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labeled oligonucleotide probes may be synthesized and used to identify polypeptide-encoding clones from the genomic library prepared from the organism. Alternatively, a labeled oligonucleotide probe containing sequences homologous to another known polypeptide gene could be used to identify polypeptide-encoding clones. In the latter case, hybridization and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g., the phosphoroamidite method described by Beucage S. L. et al. (1981) Tetrahedron Letters 22, 1859-1869, or the method described by Matthes et al. (1984) EMBO J. 3, 801-805. In the phosphoroamidite method, oligonucleotides are synthesized, e.g., in an automatic DNA synthesizer, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al. (Science (1988) 239, 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In some embodiments, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment.

However, the amino acid sequence encompassed by scope the present invention can be isolated and/or purified post expression of a nucleotide sequence in its native organism. In some embodiments, however, the amino acid sequence encompassed by scope of the present invention may be expressed by a nucleotide sequence in its native organism but wherein the nucleotide sequence is not under the control of the promoter with which it is naturally associated within that organism.

In some embodiments, the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e., recombinant DNA). However, in an alternative embodiment of the invention, the nucleotide sequence could be synthesized, in whole or in part, using chemical methods well known in the art (see Caruthers M H et al. (1980) Nuc Acids Res Symp Ser 215-23 and Horn T et al. (1980) Nuc Acids Res Symp Ser 225-232).

Molecular Evolution

Once a polypeptide-encoding nucleotide sequence has been isolated, or a putative polypeptide-encoding nucleotide sequence has been identified, it may be desirable to modify the selected nucleotide sequence, for example it may be desirable to mutate the sequence in order to prepare a polypeptide in accordance with the present invention.

Mutations may be introduced using synthetic oligonucleotides. These oligonucleotides contain nucleotide sequences flanking the desired mutation sites.

A suitable method is disclosed in Morinaga et al. (Biotechnology (1984) 2, 646-649). Another method of introducing mutations into polypeptide-encoding nucleotide sequences is described in Nelson and Long (Analytical Biochemistry (1989), 180, 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimizing PCR based mutagenesis, which can also be combined with the use of mutagenic DNA analogues such as those described in EP 0 866 796. Error prone PCR technologies are suitable for the production of variants of polypeptides with preferred characteristics.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of polypeptides with preferred characteristics. Suitable methods for performing 'shuffling' can be found in EP 0 752 008, EP 1 138 763, EP 1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo-mediated recombination methods (see, e.g., WO 00/58517, U.S. Pat. Nos. 6,344,328, 6,361, 974), for example, molecular evolution can be performed where the variant produced retains very low homology to known proteins. Such variants thereby obtained may have significant structural analogy to known proteins, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the polypeptides of the present invention which have preferred characteristics without any prior knowledge of protein structure or function, and allows the production of non-predictable but beneficial mutations or variants. There are numerous examples of the application of molecular evolution in the art for the optimization or alteration of protein activity, such examples include, but are not limited to one or more of the following: optimized expression and/or activity in a host cell or in vitro, increased or decreased enzymatic activity, altered substrate and/or product specificity, increased or decreased structural stability, altered activity/specificity in preferred environmental conditions, e.g., temperature, pH, substrate.

As will be apparent to a person skilled in the art, using molecular evolution tools a polypeptide may be altered to improve the functionality of the polypeptide Alternatively, the variant polypeptide may have increased thermostability.

Amino Acid Sequences

The present invention also encompasses the use of amino acid sequences encoded by a nucleotide sequence which encodes a polypeptide for use in any one of the methods and/or uses of the present invention.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen. 135 µl of water and 5 µg of endoproteinase Lys-C in 5 µl of water may be added to the above reaction mixture and the digestion may be carried out at 37° C. under nitrogen for 24 hours. The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Life Technologies, California, USA).

Sequence Identity or Sequence Homology

Here, the term "homologue" means an entity having a certain homology with the subject amino acid sequences and the subject nucleotide sequences. Here, the term "homology" can be equated with "identity".

In some embodiments, the homologous amino acid sequence and/or nucleotide sequence provide and/or encode a polypeptide which retains the desire characteristic(s) and/or enhances the desire characteristic(s) of the polypeptide.

In the present context, a homologous sequence is taken to include an amino acid sequence which may be at least 50%, 55%, 60%, 70%, 71%, 72%, 73%, 74%, 75%, 80%, 85%, 90%, 91%, 92%, 93%, 94%, 95%, 96%, 97%, 98%, or 99% identical, preferably at least 95%, 96%, 97%, 98%, or 99% identical to the subject sequence. Typically, the homologues will comprise the same active sites etc. as the subject amino acid sequence. Although homology can also be considered in terms of similarity (i.e., amino acid residues having similar chemical properties/functions), in the context of the present invention it is preferred to express homology in terms of sequence identity.

In the present context, a homologous sequence is taken to include a nucleotide sequence which may be at least 75, 85 or 90%, 91%, 92%, 93%, 94%, 95%, 96%, 97%, 98%, or 99% identical, preferably at least 95%, 96%, 97%, 98%, or 99% identical to a nucleotide sequence encoding a polypeptide of the present invention (the subject sequence). In some embodiments, the homologues will comprise the same sequences that code for the active sites as the subject sequence. Although homology can also be considered in terms of similarity (e.g., amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e., one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximize local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimized alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of other software that can perform sequence comparisons include, but are not limited to, the BLAST package (see Ausubel et al. 1999 Short Protocols in Molecular Biology, 4$^{th}$ Ed—Chapter 18), and FASTA (Altschul et al. 1990 *J. Mol. Biol.* 403-410). Both BLAST and FASTA are available for offline and online searching (see Ausubel et al. 1999, pages 7-58 to 7-60). However, for some applications, it is preferred to use the Vector NTI program. A new tool, called BLAST 2 Sequences is also available for comparing protein and nucleotide sequence (see *FEMS Microbiol Lett* 1999 174: 247-50; *FEMS Microbiol Lett* 1999 177: 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI ADVANCE™ 10 package.

Alternatively, percentage homologies may be calculated using the multiple alignment feature in Vector NTI ADVANCE™ 10 (Invitrogen Corp.), based on an algorithm, analogous to CLUSTAL (Higgins D G & Sharp P M (1988), *Gene* 73, 237-244).

Once the software has produced an optimal alignment, it is possible to calculate % homology, preferably % sequence identity. The software typically does this as part of the sequence comparison and generates a numerical result.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

Should Gap Penalties be used when determining sequence identity, then preferably the default parameters for the program are used for pairwise alignment. For example, the following parameters are the current default parameters for pairwise alignment for BLAST 2:

| FOR BLAST2 | DNA | PROTEIN |
|---|---|---|
| EXPECT THRESHOLD | 10 | 10 |
| WORD SIZE | 11 | 3 |

| FOR BLAST2 | DNA | PROTEIN |
|---|---|---|
| SCORING PARAMETERS | | |
| Match/Mismatch Scores | 2, −3 | n/a |
| Matrix | n/a | BLOSUM62 |
| Gap Costs | Existence: 5 | Existence: 11 |
| | Extension: 2 | Extension: 1 |

In some embodiments, the sequence identity for the nucleotide sequences and/or amino acid sequences may be determined using BLAST2 (blastn) with the scoring parameters set as defined above.

In some embodiments, the degree of identity is based on the number of sequence elements which are the same. The degree of identity in accordance with the present invention for amino acid sequences may be suitably determined by means of computer programs known in the art such as Vector NTI ADVANCE™ 11 (Invitrogen Corp.). For pairwise alignment the scoring parameters used are preferably BLOSUM62 with Gap existence penalty of 11 and Gap extension penalty of 1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids, preferably over at least 100 contiguous amino acids.

Suitably, the degree of identity with regard to an amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) that may occur, e.g., like-for-like substitution such as basic for basic, acidic for acidic, polar for polar etc. Non-homologous substitution may also occur, e.g., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine.

Replacements may also be made by non-natural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89, 9367-9371 and Horwell D C, *Trends Biotechnol.* (1995) 13, 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g., rat, mouse, bovine and primate cells), may be obtained and such homologues and fragments thereof in general will be capable of selectively hybridizing to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterized sequences. This may be useful where for example silent codon sequence changes are required to optimize codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g., a PCR primer, a primer for an alternative amplification reaction, a probe e.g., labeled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any suitable means available to those of skill in the art. They may also be cloned by standard techniques.

In some embodiments, primers will be produced by synthetic means, involving a stepwise manufacture of the desired nucleic acid sequence one nucleotide at a time. Techniques for accomplishing these automated techniques are readily available in the art.

In some embodiments, longer polynucleotides will generally be produced using recombinant means, for example using a PCR (polymerase chain reaction) cloning techniques. This will involve making a pair of primers (e.g., of about 15 to 30 nucleotides) flanking a region of the target sequence which it is desired to clone, bringing the primers into contact with mRNA or cDNA obtained from an animal or human cell, performing a polymerase chain reaction under conditions which bring about amplification of the desired region, isolating the amplified fragment (e.g., by purifying the reaction mixture on an agarose gel) and recovering the amplified DNA. The primers may be designed to contain suitable restriction enzyme recognition sites so that the amplified DNA can be cloned into a suitable cloning vector.

Hybridization

The present invention also encompasses the use of sequences that are complementary to the sequences of the present invention or sequences that are capable of hybridizing either to the sequences of the present invention or to sequences that are complementary thereto.

The term "hybridization" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridizing to the sequences that are complementary to the subject sequences discussed herein, or any derivative, fragment or derivative thereof.

The present invention also encompasses sequences that are complementary to sequences that are capable of hybridizing to the nucleotide sequences discussed herein.

Hybridization conditions are based on the melting temperature (Tm) of the nucleotide binding complex, as taught in Berger and Kimmel (1987, Guide to Molecular Cloning Techniques, *Methods in Enzymology*, Vol. 152, Academic Press, San Diego Calif.), and confer a defined "stringency" as explained below.

Maximum stringency typically occurs at about Tm–5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related polynucleotide sequences.

In some embodiments, the present invention encompasses the use of sequences that are complementary to sequences that are capable of hybridizing under high stringency conditions or intermediate stringency conditions to nucleotide sequences encoding polypeptides having the specific properties as defined herein.

In some embodiments, the present invention encompasses the use of sequences that are complementary to sequences that are capable of hybridizing under high stringency conditions (e.g., 65° C. and 0.1×SSC {1×SSC=0.15 M NaCl, 0.015 M Na-citrate pH 7.0}) to nucleotide sequences encoding polypeptides having the specific properties as defined herein.

The present invention also relates to the use of nucleotide sequences that can hybridize to the nucleotide sequences discussed herein (including complementary sequences of those discussed herein).

The present invention also relates to the use of nucleotide sequences that are complementary to sequences that can hybridize to the nucleotide sequences discussed herein (including complementary sequences of those discussed herein).

Also included within the scope of the present invention is the use of polynucleotide sequences that are capable of hybridizing to the nucleotide sequences discussed herein under conditions of intermediate to maximal stringency.

In some embodiments, the present invention covers the use of nucleotide sequences that can hybridize to the nucleotide sequences discussed herein, or the complement thereof, under stringent conditions (e.g., 50° C. and 0.2×SSC).

In some embodiments, the present invention covers the use of nucleotide sequences that can hybridize to the nucleotide sequences discussed herein, or the complement thereof, under high stringency conditions (e.g., 65° C. and 0.1×SSC).

Biologically Active

Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

Recombinant

In some embodiments, the sequence for use in the present invention is a recombinant sequence—i.e., a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T Maniatis, 1989, *Molecular Cloning: A Laboratory Manual*, Second Edition, Books 1-3, Cold Spring Harbor Laboratory Press.

Synthetic

In s the sequence for use in the present invention is a synthetic sequence—i.e., a sequence that has been prepared by in vitro chemical or enzymatic synthesis. It includes, but is not limited to, sequences made with optimal codon usage for host organisms—such as the methylotrophic yeasts *Pichia* and *Hansenula*.

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

In some embodiments, the expression vector is incorporated into the genome of a suitable host organism. The term "incorporated" preferably covers stable incorporation into the genome.

The nucleotide sequence encoding a polypeptide for use in the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g., a plasmid, cosmid, or phage vector will often depend on the host cell into which it is to be introduced.

The vectors for use in the present invention may contain one or more selectable marker genes such as a gene which confers antibiotic resistance e.g., ampicillin, kanamycin, chloramphenicol or tetracycline resistance. Alternatively, the selection may be accomplished by co-transformation (as described in WO 91/17243).

Vectors may be used in vitro, for example for the production of RNA or used to transfect, transform, transduce or infect a host cell.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some embodiments, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e., the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promote" is used in the normal sense of the art, e.g. an RNA polymerase binding site.

Enhanced expression of the nucleotide sequence encoding the enzyme of the present invention may also be achieved by the selection of heterologous regulatory regions, e.g., promoter, secretion leader and terminator regions.

Preferably, the nucleotide sequence according to the present invention is operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"-includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Organism

The term "organism" in relation to the present invention includes any organism that could comprise a nucleotide sequence according to the present invention or a nucleotide sequence encoding for a polypeptide having the specific properties as defined herein and/or products obtained therefrom.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

Suitable organisms include a prokaryote, fungus yeast or a plant.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a promoter not associated with a sequence encoding a hydrophobin or a membrane protein.

Transformation of Host Cells/Organism

The host organism can be a prokaryotic or a eukaryotic organism.

Examples of suitable prokaryotic hosts include bacteria such as *E. coli* and *Bacillus licheniformis*.

Teachings on the transformation of prokaryotic hosts are well documented in the art, for example see Sambrook et al. (Molecular Cloning: A Laboratory Manual, 2nd edition, 1989, Cold Spring Harbor Laboratory Press). If a prokaryotic host is used then the nucleotide sequence may need to be suitably modified before transformation, e.g., such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023. In one embodiment, *T. reesei* is the host organism.

Another host organism can be a plant. A review of the general techniques used for transforming plants may be found in articles by Potrykus (*Annu Rev Plant Physiol Plant Mol Biol* (1991) 42:205-225) and Christou (Agro-Food-Industry Hi-Tech Mar./Apr. 1994 17-27). Further teachings on plant transformation may be found in EP-A-0449375.

General teachings on the transformation of fungi, yeasts and plants are presented in following sections.

a. Transformed Fungus

A host organism may be a fungus—such as a filamentous fungus. Examples of suitable such hosts include any member belonging to the genera *Fusarium, Thermomyces, Acremonium, Aspergillus, Penicillium, Mucor, Neurospora, Trichoderma* and the like. In one embodiment, *Trichoderma* is the host organism, preferably *T. reesei*.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus:* 50 years on. Progress in industrial microbiology vol 29. Elsevier Amsterdam 1994. pp. 641-666).

Gene expression in filamentous fungi has been reviewed in Punt et al. *Trends Biotechnol.* (2002); 20(5):200-6, Archer & Peberdy *Crit. Rev. Biotechnol.* (1997) 17:273-306.

b. Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997); 8:554-60.

In this regard, yeast—such as the species *Saccharomyces cerevisi* or *Pichia pastoris* or *Hansenula polymorpha* (see FEMS *Microbiol Rev* (2000 24:45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J. Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al. (1983, *J Bacteriology* 153, 163-168).

The transformed yeast cells may be selected using various selective markers—such as auxotrophic markers dominant antibiotic resistance markers.

A suitable yeast host organism can be selected from the biotechnologically relevant yeasts species such as, but not limited to, yeast species selected from *Pichia* spp., *Hansenula* spp., *Kluyveromyces, Yarrowinia* spp., *Saccharomyces* spp., including *S. cerevisiae*, or *Schizosaccharomyce* spp., including *Schizosaccharomyce pombe*.

A strain of the methylotrophic yeast species *Pichia pastoris* may be used as the host organism.

In one embodiment, the host organism may be a *Hansenula* species, such as *H. polymorpha* (as described in WO 01/39544).

c. Transformed Plants/Plant Cells

A host organism suitable for the present invention may be a plant. A review of the general techniques may be found in articles by Potrykus (*Annu Rev Plant Physiol Plant Mol Biol* (1991) 42:205-225) and Christou (Agro-Food-Industry Hi-Tech Mar./Apr. 1994 17-27), or in WO 01/16308. The transgenic plant may produce enhanced levels of phytosterol esters and phytostanol esters, for example.

Culturing and Production

Host cells transformed with the nucleotide sequence of the present invention may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the enzyme.

The protein produced by a recombinant cell may be displayed on the surface of the cell.

The polypeptide may be secreted from the host cells and may conveniently be recovered from the culture medium using well-known procedures.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of secretion leader sequences not associated with a nucleotide sequence encoding a lipid acyltransferase in nature are those originating from the fungal amyloglucosidase (AG) gene (glaA—both 18 and 24 amino acid versions e.g., from *Aspergillus*), the a-factor gene (yeasts e.g., *Saccharomyces, Kluyveromyces* and *Hansenula*) or the α-amylase gene (*Bacillus*).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J., USA), Promega (Madison, Wis., USA), and US Biochemical Corp (Cleveland, Ohio, USA) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Fusion Proteins

A polypeptide for use in the present invention may be produced as a fusion protein, for example to aid in extraction and purification thereof. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6:501-6.

The amino acid sequence of a polypeptide having the specific properties as defined herein may be ligated to a non-native sequence to encode a fusion protein. For example, for screening of peptide libraries for agents capable of affecting the substance activity, it may be useful to encode a chimeric substance expressing a non-native epitope that is recognized by a commercially available antibody.

Additional Proteins

The biomimetic membranes described herein may also be used in conjunction with one or more additional proteins of interest (POIs) or nucleotide sequences of interest (NOIs).

Non-limiting examples of POIs include: proteins or enzymes involved in starch metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, α galactosidases, β galactosidases, α glucanases, glucan lysases, endo-β-glucanases, glucoamylases, glucose oxidases, α glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, hexose oxidase (D-hexose: O2-oxidoreductase, EC 1.1.3.5) or combinations thereof. The NOI may even be an antisense sequence for any of those sequences.

The POI may even be a fusion protein, for example to aid in extraction and purification.

The POI may even be fused to a secretion sequence.

EXAMPLES

The present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure.

Example 1

Materials and Methods

Sodium dodecyl sulfate (SDS), 1,2-Dioleoyl-sn-glycero-3-phosphoethanolamine (DOPE), L-α-Phosphatidylcholine (SoyPC), Tris-Base buffer (Sigma-Aldrich), and Hydrophobin (HFBII)

Micelles Formation:

SDS micelles were formed in 5 mM Tris buffer, 150 mM NaCl pH 7. An appropriate amount of SDS was dissolved in the buffer for getting a final concentration of 0.035M. The samples were shaken in a Vortex for 1 min. to ensure a final homogeneous solution.

Micelles-Protein Samples:

SDS micelles-HFBII mixtures were formed in 5 mM Tris buffer, 150 mM NaCl, pH 7. at a protein-detergent molar ratio of 1:07 (molar ratio) The optimal HFBII: SDS ratio was selected according to the data published by Zhang et al. (Zhang et al. 2011 *Adsorption Behavior of Hydrophobin and Hydrophobin/Surfactant Mixtures at the Solid-Solution Interface. Langmuir* 27:10464-74; Zhang et al. 2011. *Self-Assembly of Hydrophobin and Hydrophobin/Surfactant Mixtures in Aqueous Solution. Langmuir* 27:10514-22; Zhang et al. 2011. *Adsorption Behavior of Hydrophobin and Hydrophobin/Surfactant Mixtures at the Air-Water Interface. Langmuir* 27:113616-23). When SDS-HFBII are mixed in solution although soft manual mixing was applied to avoid the development of big amounts of foam, the mixture evolved into a gelatinous mixture which avoids any further manipulation of the sample. Alternatively the mixtures where performed in situ in the surface tension equipment.

In situ procedure: The different components of the mixture were added in consecutives steps to the air/water interface. First the correct volume of SDS micelles and afterwards the expected HFBII volume for achieving the expected 1:0.7 (molar ratio). HFBII addition step indicated with arrows in the FIG. 3.

Liposomes-Small Unilamellar Vesicles (SUV) Formation: DOPE:SoyPC 7:3 (mol ratio) vesicles were formed in 5 mM Tris buffer, 150 mM NaCl, pH 7. Stock solutions of the phospholipids were prepared in chloroform:Methanol (2:1, v/v). An appropriate amount of the stock solution was deposited in an assay tube. The organic volume was evaporated under N2 flux and later over-night (o/n) in a desiccator for ensuring the organic solvent removal. Afterwards the lipid film was hydrated for 1 h at constant temperature (45° C.) with the appropriate amount of buffer for reaching the desired final concentration. In addition, occasional vortexing was applied to avoid material deposition.

SUV (<50 nm) was obtained using a Branson 250/450 tip sonifier at 360 W/cm2 during three cycles of 30 s at intervals of 30 s to avoid sample heating.

Liposomes-Protein Samples: Lipid-HFBII samples were formed in 5 mM Tris buffer, 150 mM NaCl, pH 7. The same procedure explained above for the SUV formation was followed, with the exception that HFBII was added together with the buffer in the hydration process to get a final lipid concentration in the mixture of 1 mg/mL. The final HFBII-Lipid molar ratio was 1:07 following the ratio used with the SDS micelles. The mixing, incubation and sonication steps were the same.

Tensiometer K100:

Interfacial surface tension of the samples was registered vs. time. Samples volumes of 10 or 20 µL were deposited on the 35 mL buffer surface at a controlled temperature of 25° C.

Results and Discussion

Figure 3:
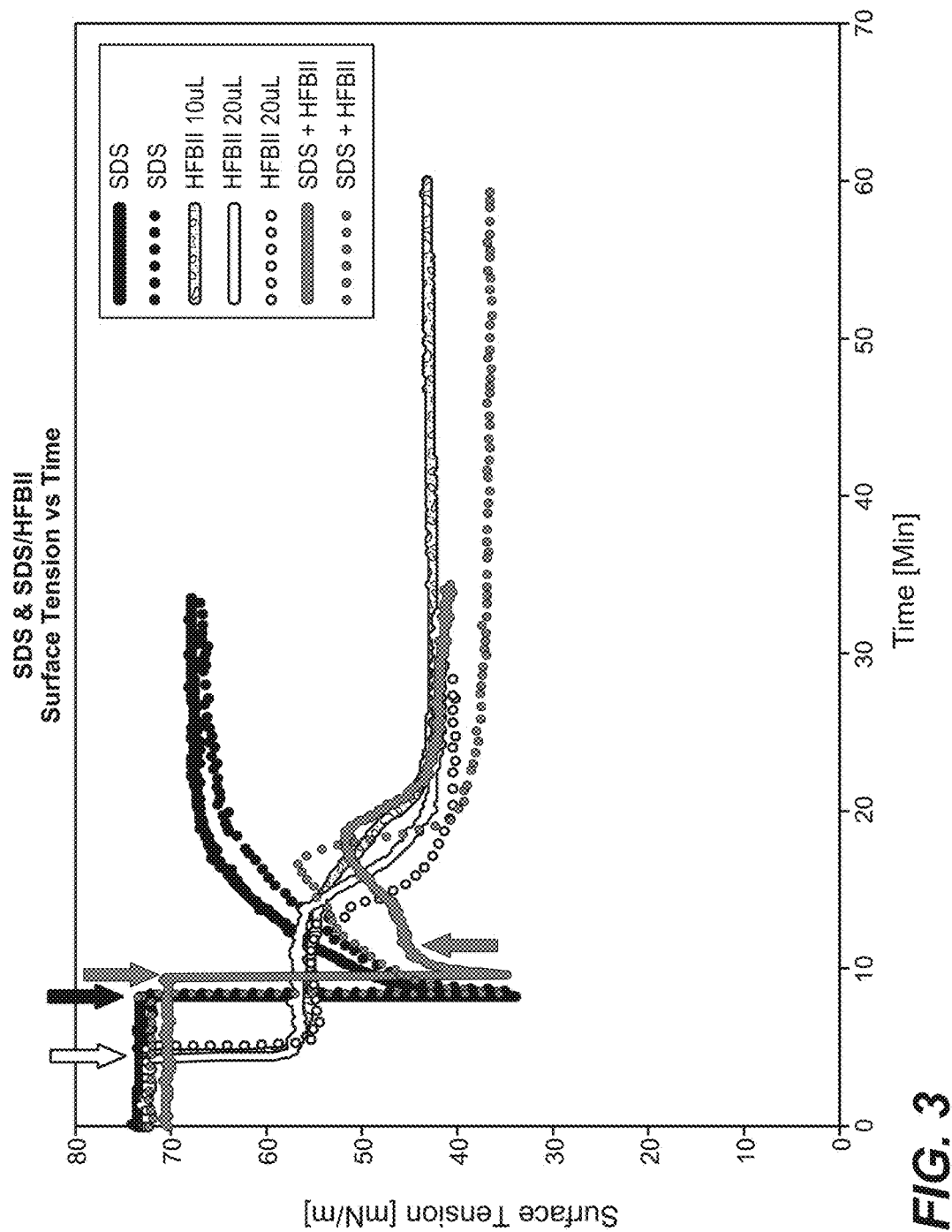
FIG. 3 depicts a graph showing surface tension vs. time of SDS and SDS-HFBII samples. The arrows show when the samples were dropped on the surface.
Figure 4:
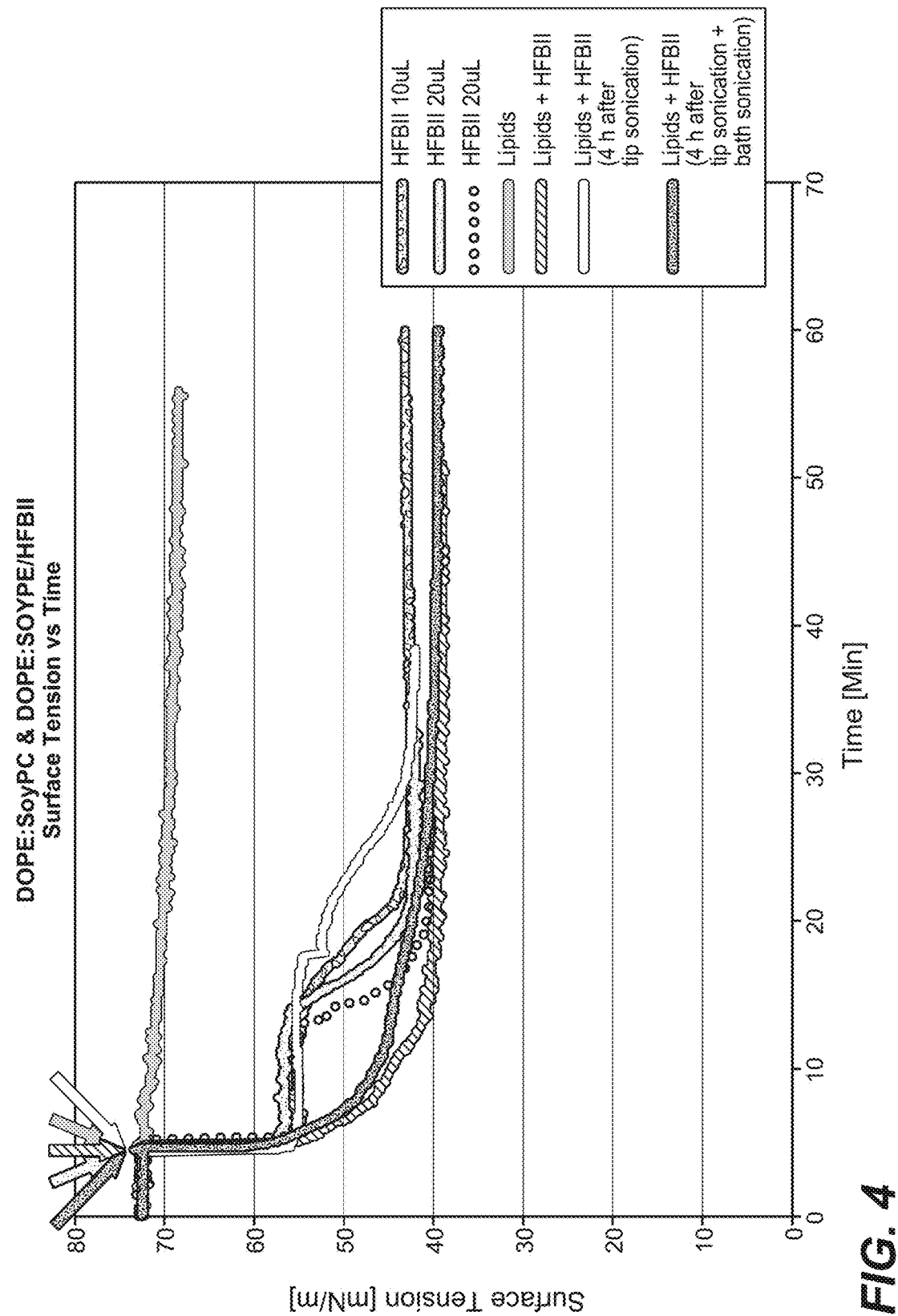
FIG. 4 depicts a graph showing surface tension vs. time of Lipids SUV and Lipids-HFBII SUV. The arrows show when the samples were dropped on the surface.

FIG. 1 depicts a graph showing all the surface tension curves vs. time. For facilitating the comparison and the discussion the curves have been split in two different graphics. FIG. 3 depicts a graph in which data related to SDS and SDS/HFBII has been plotted. FIG. 4 depicts a graph in which data related to Liposomes and Liposomes/HFBII mixtures have been plotted.

To our knowledge there is no exiting data on HFB-liposomes that can be used as a reference. However SDS-HFB has been already very well characterized by Zhang et al. (Zhang et al. 2011 *Adsorption Behavior of Hydrophobin and Hydrophobin/Surfactant Mixtures at the Solid-Solution Interface. Langmuir* 27:10464-74; Zhang et al. 2011. *Self-Assembly of Hydrophobin and Hydrophobin/Surfactant Mixtures in Aqueous Solution. Langmuir* 27:10514-22; Zhang et al. 2011. *Adsorption Behavior of Hydrophobin and Hydrophobin/Surfactant Mixtures at the Air-Water Interface. Langmuir* 27:113616-23). Adsorption Behavior of Hydrophobin and Hydrophobin/Surfactant Mixtures at the Solid-Solution Interface. Langmuir 27:10464-74; Zhang et al (2011). Self-Assembly of Hydrophobin and Hydrophobin/Surfactant Mixtures in Aqueous Solution. Langmuir 27:10514-22; Zhang et al (2011). Therefore, SDS-HFB mixtures have been added as reference data. According to those references the HFBII-SDS molar ratio of 1:0.7 is the optimal one for obtaining the maximum adsorption of the mixture into an air-water interface. Otherwise it would be a competition between SDS and HFBII and the interface would be mainly occupied by HFBII.

Figure 2:
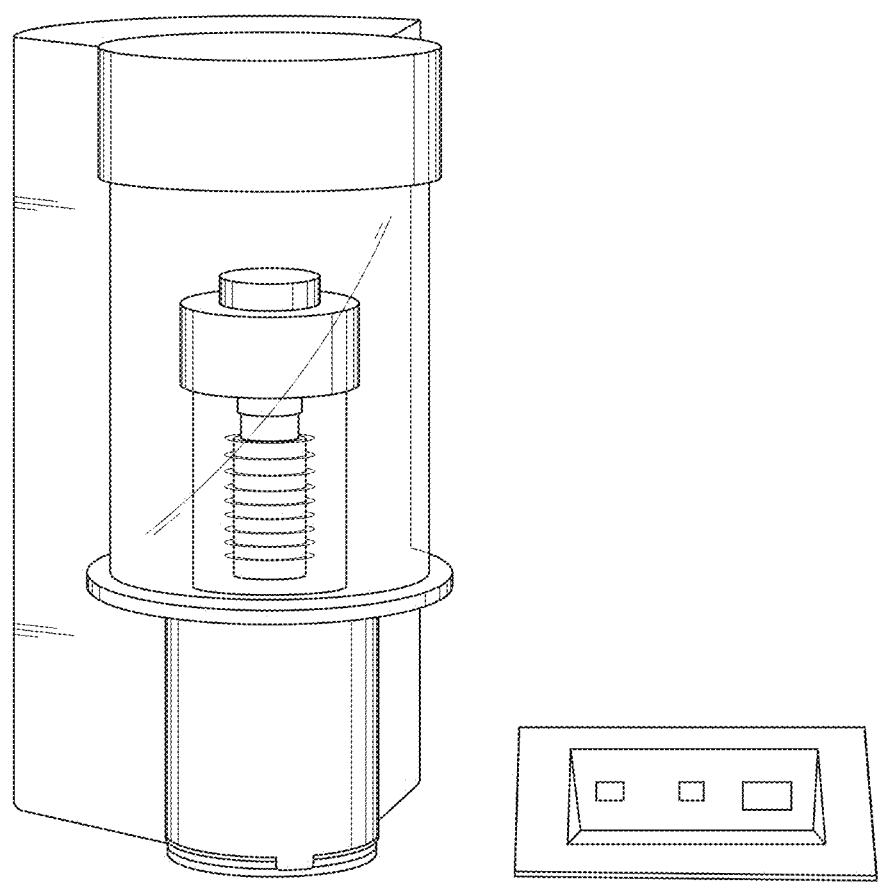
FIG. 2 shows a KRÜS Tensiometer K100.

The minimum volume allowed (35 mL) in the Tensiomiter K100 cell (FIG. 2) have been used in these experiments. A spreading set up was followed instead of following the adsorption set up. In the adsorption set up the sample would be a) injected from the bottom of the Tensiometer cell orb) premixed with the buffer before starting the surface tension registration. In the spreading setup the sample is dropped on the top of the buffer. The surface tension of the buffer is registered from the t=0 and it is confirmed that tensioactive molecules are not present in the solution. The sample is then dropped on the surface. If the mixture is tensioactive the surface tension will drop. In the spreading set up it is possible to work with very small volumes, μL, of samples not necessarily very concentrated as soon as they are containing tensoactive molecules.

FIG. 3 shows the surface tension curves of SDS, HFBII and SDS/HFBII samples. 10 μL of the SDS stock solution was dropped on the surface. Due to the deposition the surface tension is dropping intensively, but once the SDS molecules are stably spread on air/water interface the surface the surface tension values are very close to the pure buffer. This indicates that SDS molecules at that concentration are not showing a high tensioactivity.

10 or 20 μL from the HFBII stock solution were deposited on the buffer surface. It seems that HFBII spreading is happening in two well differentiated phases. It is probable that the first phase are reflecting the HFBII reorganization on the surface and once the molecule are covering the full surface then the maximum tensoactive value is reached for the HFBII layer formed on the surface.

Due to the limitation of working with premixed SDS/HFBII samples the molecules were added in two different steps. 10 μL from the SDS stock solution was added to the samples and immediately followed by the addition of 10 μL from the HFBII stock solution. The curves registered from these samples are having a complex profile. The first intense drop on the surface tension is due to the SDS addition and this is slowed by the addition of the HFBII. The spreading of the HFBII is showing a different spreading kinetic than when is not facing SDS in the surface. Duplicates of these samples are not completely equal and the most probable reason is small differences in the way HFBII facing the SDS surface. But the HFBII presence reverts without any doubt tensioactivity lost shown by the pure SDS samples. The mixture is reaching the same tensoactive values than HFBII alone.

FIG. 4 shows results with liposomes and HFBII-liposomes samples. The phospholipid liposomes have shown the expected low surface tension profile. In presence of the HFBII the surface tension dropped to typical values observed on tensioactive phospholipid-protein membranes mixtures. Interestingly, if the sample is tested right after preparation, the sample showed the expected phospholipid-protein mixture profile. However, if the same sample is tested after being kept at room temperature without any agitation during 4 h, the curve showed a biphasic behavior very similar to the one observed on HFBII alone. This suggests that HFBII is leading the sample profile. However, if the same sample is sonicated in a water bath for one minute, the profile is back to the one observed on the freshly prepared sample showing the same surface tension stable profile. This would indicate that while in-solution interactions between HFBII and the phopholipids is not completely stable (and that is changing with the passing of time), this is a reversible process that is not limiting the stability properties of HFBII on phospholipids membranes, i.e. the resulting interfacial interaction remains highly stable.

These results indicate that HFBII can stabilize phospholipids membranes.

Example 2

AqpZ-HFBII Mixtures

Materials:

AqpZ: 20 mg/mL stock solution containing 20 mM Tris, 300 mM NaCl, 300 mM Imidazole, 10% glycerol, 0.3% Surfactant, pH 8.0

HFBII: 8.5% stock solution containing 0.13% potassium sorbate, pH 3.5

Procedure:

4 solutions containing AqpZ and HFBII mixtures were prepared with different AqpZ and HFBII concentrations in 10 mM PBS buffer (pH=7.6) (Samples 1-4). The samples were dialyzed (cutoff=1 kDa) against 10 mM PBS buffer for 72 hours.

The surfactant was removed via dialysis which exposes the hydrophibc surfaces of AqpZ to be accessed by HFBII.

For comparison, 4 solutions containing only AqpZ or HFBII were also prepared (Control 1-4) and subject to the same dialysis process.

| | AqpZ | | |
|---|---|---|---|
| HFB | 1000 ppm | 100 ppm | 0 ppm |
| 1000 ppm | Sample 1 | Sample 2 | Control 3 |
| 100 ppm | Sample 3 | Sample 4 | Control 4 |
| 0 ppm | Control 1 | Control 2 | |

Characterization:

The mixtures were examined with dynamic light scattering (DLS) using a Melvern nano Zetasizer (Malvern Instruments Ltd, Worcestershire, UK). A disposable cuvette was first cleaned with nitrogen gas to remove dust. Then 400 μl of the sample was placed in the cuvette. The cuvette was inserted into the Zetasizer. DTS (Nano) software (Malvern Instruments Ltd) was used to determine the particle size.

Results & Discussions:

The objective of this experiment is to examine the interaction between AqpZ and HFBII proteins. Such interaction may be utilized to stabilize AqpZ dispersion, immobilize AqpZ on substrates and in addition create complex functional systems.

Figure 15A:
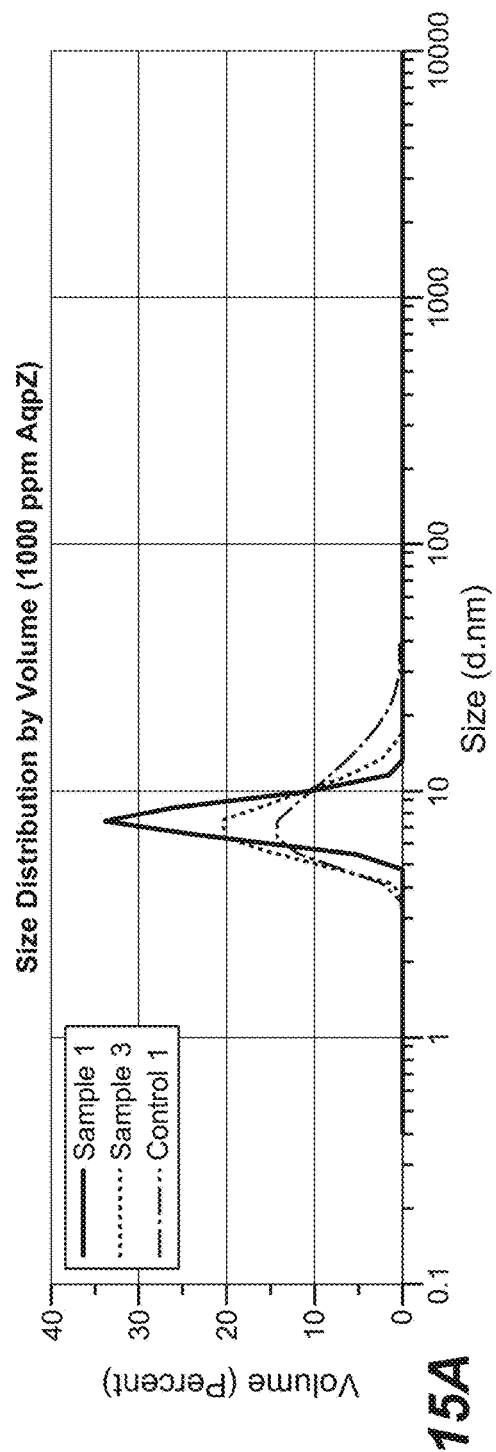
FIG. 15A depicts a graph showing the volume vs particle size distribution of solutions containing 1000 ppm of AqpZ and HBFII at concentrations of 1000 ppm (Sample 1), 100 ppm (Sample 3) and 0 (Control 1).
Figure 15B:
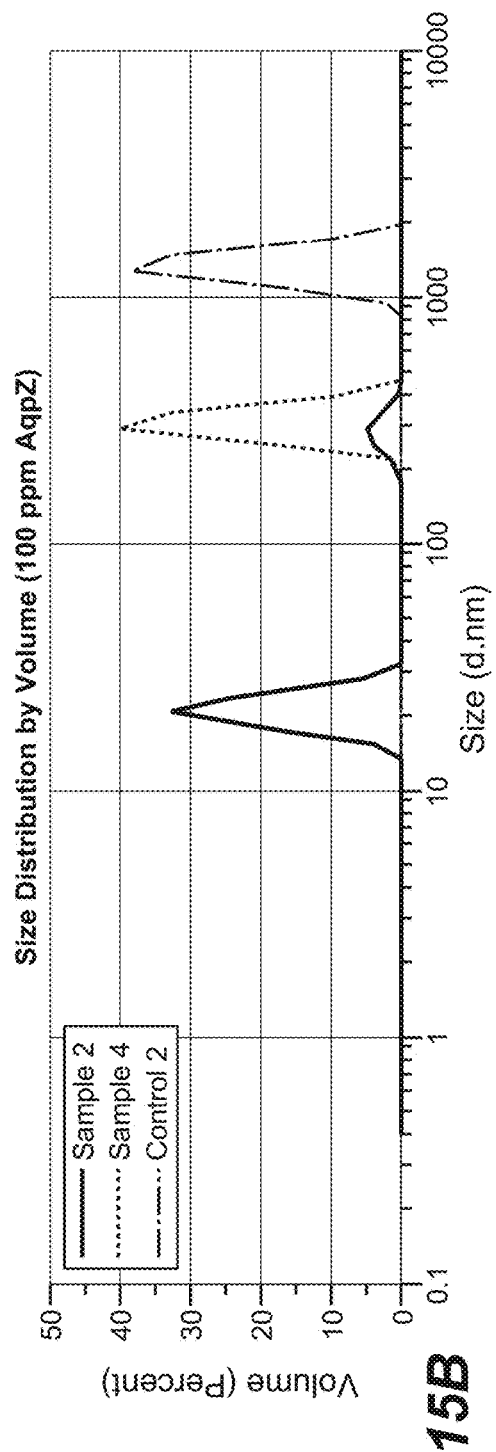
FIG. 15B depicts a graph showing the volume vs particle size distribution of solutions containing 100 ppm of AqpZ and HBFII at concentrations of 1000 ppm (Sample 2), 100 ppm (Sample 4) and 0 (Control 2).

Herein we investigated 4 mixtures at different AqpZ and HFBII concentrations (Samples 1-4) using DLS and results are summarized below and in FIGS. 15A and 15B.

All samples after 72 hour dialysis remained stable and homogeneous. The control sample 1 with 1000 ppm AqpZ showed a broad particle size distribution centered at 9 nm. Especially, the long tail at the left side of the curve suggests the presence of large aggregated structures. In comparison, samples with the same AqpZ concentration and additional 1000 ppm or 1000 ppm HFBII (Samples 1 and 3) showed the same mean particle size but narrower size distribution, indicating HFBII may have assisted the dispersion of AqpZ in solution. It is worth mentioning that HFBII also forms particles of 4~10 nm (data not shown).

At 100 ppm AqpZ concentration, the effect of HFBII to help disperse AqpZ is more prominent. While 100 ppm AqpZ formed aggregates >1 μm, stead decrease in average particle size was clearly observed with the addition of 100 ppm and 1000 ppm HFBII. (Samples 2 and 4) Especially at HFBII/AqpZ ratio of 10 (Sample 4), two orders of magnitude increase in structural size was registered. Those structures cannot be attributed to HFBII only which has an average particle size of 4~10 nm (data not shown). Therefore, it is possible that AqpZ/HFBII complexes have been formed under those conditions.

The reason pure AqpZ dispersion is more stable at 1000 ppm than 100 ppm is probably because of the residue surfactant.

These results suggest the presence of interaction between AqpZ and HFBII protein, perhaps in multiple modes as a function of their concentrations. Such interaction can be utilized to disperse and stabilize AqpZ in solution.

Example 3

Surface Modification of Block Copolymer Membranes by HFBII

Materials: $PMOXA_{15}$-$PDMS_{67}$-$PMOXA_{15}$ was acquired from Sigma-Aldrich. HFBII: 8.5% stock solution containing 0.13% potassium sorbate, pH 3.5.

Procedure:

$PMOXA_{15}$-$PDMS_{67}$-$PMOXA_{15}$ was dissolved in chloroform with rigorous agitation and left still at room temperature to reach homogeneity. Block copolymer membranes were prepared by casting ~0.2 mL chloroform solution onto triple DI water washed glass slide (1 in.×3 in.) and dried in air for 72 hrs. The resulting membrane was further dried in a vacuum oven at 0.3 mbar at room temperature for 60 min to remove remaining chloroform. For HFB surface modification, the glass slide with polymer membrane was soaked in 1000 ppm HFB solution for 30 min, followed by washing with DI water and dried in vacuum oven at 0.3 mbar for another 60 min. For comparison, another piece of the same membrane sample was soaked in water for the same duration and subject to the same drying procedure.

Characterization:

A ramé-hart standard Goniometer (ramé-hart Instrument Co., Netcong, N.J., United States) was used for WCA determinations. The substrate was placed in the Goniometer and leveled. A water drop was placed onto the surface using a syringe. The software DROPimage Advanced (ramé-hart Instrument Co.) was used to measure the water contact angles, by defining the bottom of the droplet and profiling the drop. The left and right contact angles of the drop were averaged. This method was repeated in different locations on the substrate surface until the contact angles of five water drops were determined and averaged.

Figure 16:
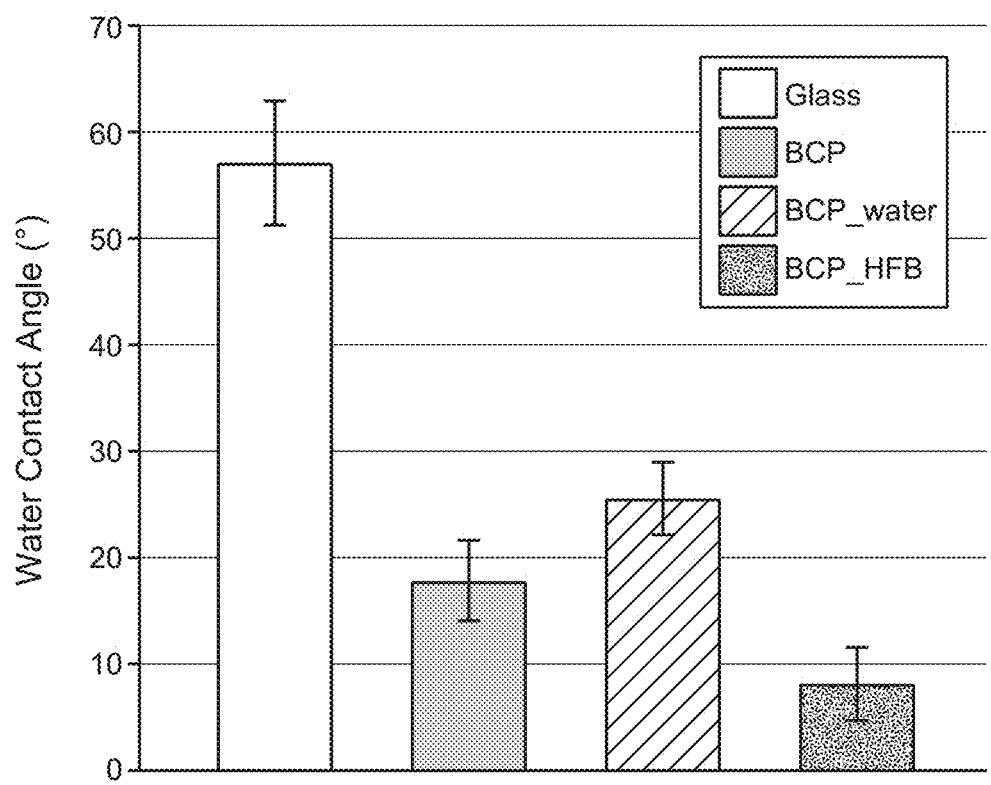
FIG. 16 depicts a graph summarizing the water contact angle results for glass substrate, BCP coated glass, BCP coated glass after HFB modification, and a control sample of BCP coated glass soaked in water.

Results & Discussions:

FIG. 16 summarizes the water contact angle results for glass substrate, BCP coated glass, BCP coated glass after HFB modification, and a control sample of BCP coated glass soaked in water. While the BCP film has significantly lower water contact angle (18±4°) compared to glass substrate (57±6°), treatment with HFB further reduced the water contact angle to 8±3°. In comparison, BCP film treated with water showed slightly increased water contact angle (26±3°), indicating the BCP film may be partially dissolved by water due to insufficient cross-linking.

The results suggest the presence of HFB coating on the $MOXA_{2000}$-$DMS_{4000}$-$MOXA_{2000}$ film and it may help stabilize block copolymer film/membrane, either in planar or vesicle forms. (Reference: S-layer protein stabilization of block copolymer membrane (Desalination by biomimetic aquaporin membranes: Review of status and prospects. Desalination 308:34-40; Tang et al (2013))

Example 4

AqpZ/HFBII Proteoliposomes Preparation

AqpZ Expression and Purification

Both wild type AqpZ and an inactive mutant AqpZR189A (i.e., a mutant with low water permeability) can be expressed and used in the present example. The inactive mutant can be used as a negative control to the AqpZ wild type. Genomic DNA from *E. coli* DH5a can be employed as a source for amplifying the AqpZ gene, using gene specific primers with the addition of 6-Histag sequence at the N-terminus. The amplified AqpZ is digested with the enzyme Ndel and BamH I and then ligated to the similarly digested pEt3a vector DNA. The positive clones are verified by PCR-screening. Then the authenticity of the constructs is confirmed by DNA sequencing (1st-base). ForAqpZR189A, the arginine residue at position 189 is replaced with alanine to the pET3a/AqpZ using the Quikchange™ site-directed mutagenesis (SDM) kit. The mutagenesis constructs is confirmed by DNA sequencing (1st-base).

Expression and purification of both AqpZ wild type and AqpZ R189A is performed according to methods known in the art. The purified ApqZ wild type and AqpZR189A are stocked in buffer (20 mM TrispH8.0, 300 mM NaCl, 300 mM Imidazole, 2 mM b-mercaptoethanol, 10% glycerol, containing 30 mM n-octyl b-DGlucopyranoside) and kept frozen at 80° C. Protein concentration is determined by UV absorbance at 280 nm using a Nanodrop 1000 spectrophotometer (ThermoScientific, Massachusetts, USA, AqpZ extinction coefficient=35,090$M^{-1}$ $cm^{-1}$, molecular weight=24,524 g/mol).

AqpZ and HFBII Incorporation

Lipid vesicles (i.e., liposomes) are prepared by the film rehydration method. Briefly, a thin lipid film is formed by drying a 10 mg DOPC lipid dissolved in 0.5 ml chloroform solution under nitrogen headspace. The DOPC film is kept in a vacuum desiccators for at least 2 h, before a 1 ml phosphate buffered saline (PBS) buffer solution (pH7.4) is added to rehydrate the film followed by 3cycles of freeze-thaw treatment. The resulting solution, containing unilamellar liposomes, is extruded through a 200 nm pore size polycarbonate filter 21 times (Avestin extruder, Avestin, Canada) to obtain liposomes with uniform size distribution.

Proteoliposomes are prepared using the dialysis method by incorporating AqpZs (both wild type and the inactive mutant) and HFBII at different concentrations (0.01-20 mM) into the DOPC liposomes. Briefly, a 10 mg/ml DOPC liposome suspension containing 1% detergent OG and an AqpZ/HFBII solution are mixed at a protein to lipid molar ratio of 1:200 for AqpZ, and different concentrations between a 0.1-20 mM is then removed from the proteoliposome solution by dialyzing against a PBS buffer solution for 3 days.

Membrane Substrate Preparation

Microporous membrane substrates are formed by the phase inversion method. Briefly, the polymer dope (16 wt % PS, 77 wt % NMP, 5 wt % PEG, and 2 wt % LiCl) is stirred at 70° C., degassed, and cooled down to room temperature (23° C.). A 15 ml sample of dope is cast on a clean glass plate with a thickness of 200 mm using an Elcometer 4340 Motorized Film Applicator (Elcometer Asia Pte Ltd.). The glass plate with the nascent film is smoothly immersed into a coagulant bath (tap water at room temperature) to form the PS substrate.

Membrane Rejection Layer Preparation

The synthesis procedures for forming the membrane rejection layer is depicted in Y. Zhao et al., (*Synthesis of robust and high-performance based biomimetic membranes by interfacial polymerization-membrane . . . , Journal ofMembrane Science* (2012), http://dx.doi.org/10.1016/j.memsci.2012.08.039), where Diaminobenzene (MPD) and Trimesoly Chloride (TMC) are used as monomers to form a salt-rejection polyamide layer via inter-facial polymerization whereas AqpZ/HFBII containing proteoliposomes are added to create preferential water paths in the rejection layer. The PS substrate is first soaked in a MPD aqueous solution containing 1% MPD, 0.1% SDS, and 10 mg/ml proteoliposomes (either AqpZ wild type/HFBII or AqpZ R189A/HFBII) for 10 min. The soaked substrate is held horizontally at room temperature for 30 min, and the excess aqueous solution is removed by compressed nitrogen gas. The TMC solution (0.1% in n-Hexane) is then gently poured on to the substrate surface to react with the residue MPD to form the rejection layer. The resulting membranes are kept in flowing tap water overnight to remove excess monomers and are stored in Milli-Q water. Additional membranes without the inclusion of proteoliposomes (i.e., conventional TFC polyamide membranes) are also prepared for comparison purposes.

Liposome and Proteoliposome Characterization

The sizes of liposomes and proteoliposomes are determined using a NanoZetasizer (NanoZS, Malvern Instruments Limited, UK). Their water permeability is characterized by an SX20 Stopped-Flow Spectrometer (Applied Photophysics, UK). The fluorescence kinetic mode is chosen for the stopped-flow test, with a light source of 500 nm wavelength. Rapid mixing of vesicle solution and draw solution (sucrose) is driven by 8 atm pressurized nitrogen gas with a dead time of 500 ms. The vesicle volume reduction as a result of water transport out of the vesicles under the osmolarity gradient is monitored, and used for water permeability(Pf) calculation:

$$P_f = k/(S/V_0 V_w \Delta osm)$$

where S/V0 is the surface area to initial volume ratio of the vesicle, Vw is the partial molar volume of water (18 cm3/mol), and Δosm is the difference in osmolarity between the intravesicular and extra vesicular aqueous solutions. The rate constant k is determined by curve fitting of the stopped-flow results with single order exponential. The k values are the averages obtained from 5 to 10 independent stopped flow measurements.

Membrane Characterization

Microscopic Characterization. Membranes are dried in a vacuum desiccators for 24 h before microscopic characterization.

Atomic force micrographs (AFM) are captured by a Park Systems XE-100 AFM (USA). Samples, sputter-coated with a thin film of gold, are also imaged by an FE-SEM (Field-emission scanning electron microscopy, JSM-7600F, JEOL, Japan).

Membrane Separation Properties. Separation properties of the synthesized biomimetic membranes are characterized in a standard cross flow reverse osmosis set up. Briefly, a membrane coupon with an active surface area of 42 cm$^2$ is mounted in the test cell (CF42 Membrane Cell, Sterlitech). The feed solution (10 mM NaCl at 2070.5 1 C) is pumped at a constant cross flow velocity of 20 cm/s. A diamond-shaped feed spacer is used to minimize concentration polarization Membranes are compacted for 2 h at the desired testing pressure before sample collection for water flux and rejection measurements. Membrane permeate flux(Jv) is determined using the gravimetric method, and NaCl rejection(R) is obtained based on conductivity measurements (Ultrameter II, Myron L Company, Carlsbad, Calif.) of the permeate and feed water. The water permeability(A) and NaCl permeability(B) are calculated by the following equations, respectively $$A = J_V/(\Delta P - \Delta \pi)$$

$$B = (1/R - 1)J_V$$

where ΔP is the applied pressure and Δπ is the osmotic pressure difference across the membrane.

Example 5

Liposome and Proteoliposome Preparation

Lipid vesicles are prepared by the film rehydration method. Briefly, A 10 mg lipid dissolved in 0.5 ml chloroform is dried under nitrogen gas to form a thin lipid film. In some experiments, a predetermined amount of cholesterol can be is kept in a vacuum desiccator for at least 2 hours. A 1 ml phosphate buffered saline (PBS) buffer solution (pH 7.4) is used to rehydrate the lipid film, followed by 3 cycles of freeze thaw treatment. The resulting solution contains unilamellar lipid vesicles with wide size distribution. Liposomes with uniform size are obtained by extruding the solution through a 200 nm pore size polycarbonate filter for 21 times using an extruder. Proteoliposomes are prepared by incorporating AqpZ and HFBII into liposome by dialysis. Briefly, an AqpZ/HFBII solution is mixed with a second solution containing 10 mg/ml lipid vesicles and 1% detergent OG at a lipid to protein ratio of 200:1, followed by incubating at room temperature for 1 hr. Dialysis tubing (Spectrum laboratories, USA, with MWCO 12-14 KDa) is used to remove OG from the proteoliposome solution by dialyzing it against a PBS buffer solution at pH 7.4 for 3 days. During this period, the dialysis PBS buffer solution is changed once every day. After the 3-day dialysis, AqpZ (wild type or R189A) and HFBII should be successfully reconstituted into lipid vesicles.

Preparation of a Biomimetic Membrane Having Incorporated Lipid-AqpZ/HFBII Vesicles A commercial UF membrane (MWCO, 50,000 Dalton) is used as substrate, 50 ml aqueous amine solution 1.5 wt. % MPD containing 0.08 mg/g DOPC-AqpZ/HFBII vesicles is spread onto the surface of the UF membrane substrate, and kept the substrate wet with aqueous solution for 15 min. After that, the aqueous amine solution is removed from the surface and the substrate is standed vertically in the air for 10 min, followed by blowing the surface to remove any possible aggregated vesicles onto the surface with compressed nitrogen gas at 2 bar for 1 min. Then the substrate continues to stand vertically to dry for another 20 min. Subsequently, a 0.1 w/v % TMC solution is poured on the skin layer of the saturated substrate and reacted for 1 min. The resultant membrane is stored in Milli-Q water till to use. The resulting membrane is fixed in a testing cell. Feed solution (500 ppm NaCl) is pumped at 200 psi from the feed tank, flowed against the active layer of membrane and is then returned to the tank. Permeate is collected and the weight is measured and concentration of solute is determined by conductivity measurement in order to calculate flux and rejection.

Example 6

Polymersome Preparation $PMOXA_{15}$-$PDMS_{67}$-$PMOXA_{15}$ is dissolved in chloroform with rigorous agitation and left still at room temperature to the homogeneous mixing together. The concentration in the solution should be from 1.0 to 20.0 w/v. % (8-12 w/v. %). Then, the chloroform is evaporated under nitrogen purge in a rotary vapor evaporator. The copolymer is further dried in a vacuum oven at 0.3 mbar at room temperature overnight to remove the trace amount of remaining solvent. After that, 1 ml of PBS solution is added to the dried block copolymer and the mixture is again subject to rigorous agitation for a pre-determined duration. The diameter of polymersome vesicle is obtained by TEM image. The diameter of the polymersome vesicle could vary from 200 nm to 350 nm Preparation of Polymersome-AqpZ/HFBII Vesicles The process of preparation of polymersome-AqpZ/HFBII vesicles is the same as lipid vesicles as described in the Examples above, but the polymer to AqpZ/HFBII ratio is changed to 20:1-500:1. Vesicles using different ratios within this range are spread into UF membranes are tested as described below.

Preparation of a Composite Membrane Having Incorporated Copolymer Vesicles

The composition of reactive monomer solution in two phase and the process of interfacial polymerization are similar to Example 3, except, 0.08 mg/g (PMOXA$_{15}$-PDMS$_{67}$-PMOXA-$_{15}$) polymersome vesicles with or without AqpZ/HFBII are dissolved in the aqueous amine solution. Reverse osmosis testing is done as in Example 3.

Example 7

Encapsulation of Proteins and Reconstitution of Channel Proteins in PMOXA-PDMS-PMOXA Triblock Copolymer Vesicles For the reconstitution experiments, the well-characterized bacterial porin OmpF can be used. A porin stock solution (13.3 mg mL.sup.-1 in 1 wt % octyl-polyoxyethylene, 100 mM NaCl, and 2.5 mM Hepes, pH 7.4) is mixed with different concentration of HFBII stock solution (8.5% stock solution containing 0.13% potassium sorbate, pH 3.5) and 17 wt % solution of Poly (2-methyloxazoline)-block-poly (dimethylsiloxane)-block-poly(2-methyloxazoline) (PMOXA-PDMS-PMOXA) triblock copolymer in ethanol to a final molar ratio of 1:1000 (porin:polymer). For encapsulation of the enzyme beta-lactamase in the interior of the vesicle, the solution is slowly added to an aqueous beta-lactamase solution (0.024 mg/ml in 10 mM Hepes, 100 mM NaCl, pH 7.4) to a final copolymer concentration of 1 wt %. The resulting dispersion is extruded through Nucleopore filters, pore width 200 nm, which should result in a monodisperse collection of vesicles having an average diameter of 250 nm$^3$.

The vesicles can be polymerized by irradiating the vesicle dispersion for 2 minutes with uv light.

10 µl of a 1 mM ampicillin solution (in 10 mM Hepes, 100 mM NaCl, pH 7.4) is added to the nanocapsule dispersion and the mixture is incubated for 30 minutes. Starch iodine reagent is prepared by mixing 5 ml of a 8 mM iodine, 320 mM potassium iodide solution with 20 ml 1M sodium wolframate in 2 M acetic acid and then adding 5 ml of 2 wt % soluble starch which had been dissolved in 1 M acetic acid by boiling gently for 3 minutes. Subsequently, 0.5 ml of the starch-iodine reagent is added to the vesicle mixture and the absorbance of the starch-iodine complex was at 623 nm is measured as a function of time.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A composition comprising a stabilized biomimetic membrane comprising a membrane protein and a Class II hydrophobin, wherein said stabilized biomimetic membrane is formed after adding said Class II hydrophobin to a biomimetic membrane forming solution, wherein the Class II hydrophobin is added at a concentration of 0.1 μM-50 mM.

2. The composition of claim 1, wherein said membrane protein is an aquaporin.

3. The composition of claim 2, wherein said aquaporin is AQPZ.

4. The composition of claim 2, wherein the aquaporin is of plant origin.

5. The composition according to claim 2, wherein the aquaporin is selected from the group consisting of a Tonoplast Intrinsic Protein, a Plasma Membrane Intrinsic Protein, and a Nodulin-26 like Intrinsic Protein aquaporin, and mixtures and hybrids thereof.

6. The composition according to claim 2, wherein the aquaporin is an aquaglyceroporin (GLpF).

7. The composition according to claim 6, wherein said GLpF is selected from the group consisting of a GLPA channel, a GLPB1 channel, a GLPB2 channel, a GLPB3 channel, and a GLPY2 channel, and mixtures and hybrids thereof.

8. The composition according to claim 1, wherein the Class II hydrophobin has the general formula:

(Y1)$n$-B1-(X1)$a$-B2-3-(X3)$c$-B4-(X4)$d$-B5-(X5)$e$-B6-7-(X7)$g$-B8(Y2)$m$ wherein:

m and n are independently 0 to 200;

B1, B2, B3, B4, B5, B6, B7 and B8 are each independently amino acids selected from Cys, Leu, Ala, Ser, Thr, Met or Gly, at least 6 of the residues B1 through B8 being Cys;

a is 6 to 12;

c is 8 to 16;

d is 2 to 20;

e is 4 to 12; and g is 5 to 15.

9. The composition according to claim 8, wherein the Class II hydrophobin has the general formula:

(Y1)$n$-B1-(X1)$a$-B2-B3-(X3)$c$-B4-(X4)$d$-B5-(X5)$e$-B6-B7-(X7)$g$-B8-(Y2)$m$ wherein:

m and n are independently 0 to 10;

B1, B2, B3, B4, B5, B6, B7 and B8 are each independently amino acids selected from Cys, Leu or Ser, at least 7 of the residues B1 through B8 being Cys;

a is 7 to 11;

c is 11;

d is 4 to 18;

e is 6 to 10; and g is 7 to 10.

10. The composition according to claim 8 or claim 9, wherein all 8 of the residues B1 through B8 are Cys.

11. The composition according to claim 10, wherein the group (X3)c comprises the sequence motif ZZXZ, wherein Z is an aliphatic amino acid; and X is any amino acid.

* * * * *